US009186411B2

(12) United States Patent
Hiraishi et al.

(10) Patent No.: US 9,186,411 B2
(45) Date of Patent: Nov. 17, 2015

(54) PHARMACEUTICAL COMPOSITION

(75) Inventors: Yasuhiro Hiraishi, Osaka (JP); Muneo Nonomura, Osaka (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 380 days.

(21) Appl. No.: 13/056,593

(22) PCT Filed: Jul. 27, 2009

(86) PCT No.: PCT/JP2009/063708
§ 371 (c)(1),
(2), (4) Date: Jan. 28, 2011

(87) PCT Pub. No.: WO2010/013823
PCT Pub. Date: Feb. 4, 2010

(65) Prior Publication Data
US 2011/0124687 A1 May 26, 2011

(30) Foreign Application Priority Data
Jul. 28, 2008 (JP) ................................. 2008-194219

(51) Int. Cl.
*A61K 31/4427* (2006.01)
*C07D 207/30* (2006.01)
*A61K 47/12* (2006.01)
*A61K 9/20* (2006.01)
*A61K 9/28* (2006.01)
*A61K 47/02* (2006.01)
*A61K 47/10* (2006.01)

(52) U.S. Cl.
CPC ............... *A61K 47/12* (2013.01); *A61K 9/2013* (2013.01); *A61K 9/2018* (2013.01); *A61K 9/2853* (2013.01); *A61K 9/2866* (2013.01); *A61K 31/4427* (2013.01); *A61K 47/02* (2013.01); *A61K 47/10* (2013.01)

(58) Field of Classification Search
USPC ......................................... 514/378; 546/276.4
See application file for complete search history.

(56) References Cited

U.S. PATENT DOCUMENTS

| 6,086,919 | A | 7/2000 | Bauer et al. | |
|---|---|---|---|---|
| 6,165,507 | A | 12/2000 | Chariot et al. | |
| 6,479,529 | B1 * | 11/2002 | Lang ............................. | 514/378 |
| 7,977,488 | B2 * | 7/2011 | Kajino et al. ............ | 546/276.4 |
| 2003/0045724 | A1 | 3/2003 | Fujishima et al. | |
| 2004/0092582 | A1 | 5/2004 | Kawano et al. | |
| 2004/0224020 | A1 * | 11/2004 | Schoenhard .................. | 424/471 |
| 2005/0037070 | A1 | 2/2005 | Hall et al. | |
| 2005/0038077 | A1 | 2/2005 | Kohlrausch | |
| 2005/0202089 | A1 | 9/2005 | Chariot et al. | |
| 2008/0139639 | A1 | 6/2008 | Kajino et al. | |
| 2009/0104264 | A1 | 4/2009 | Bando et al. | |

FOREIGN PATENT DOCUMENTS

| DE | 10337697 A1 | 3/2005 |
|---|---|---|
| EP | 0901787 A1 | 3/1999 |
| EP | 1382338 A1 | 1/2004 |
| EP | 1419775 A1 | 5/2004 |
| EP | 1437130 A1 | 7/2004 |
| EP | 1803709 A1 | 7/2007 |
| EP | 2062579 A1 | 5/2009 |
| JP | 3044333 A | 2/1991 |
| JP | H09-504806 A | 5/1997 |
| JP | 11-147819 | 6/1999 |
| JP | 2000-515535 A | 11/2000 |
| JP | 2005263788 A1 | 9/2005 |
| JP | 2006-001912 A | 1/2006 |
| JP | 2007056018 A | 3/2007 |
| JP | 2007-182451 A | 7/2007 |
| WO | PCT/US94/08200 | 2/1995 |
| WO | PCT/CA97/00393 | 12/1997 |
| WO | WO-98/05320 A1 | 2/1998 |
| WO | WO99/34782 A1 | 7/1999 |
| WO | WO03/074076 A2 | 9/2003 |
| WO | PCT/JP2003/06596 | 12/2003 |
| WO | WO2004089342 A2 | 10/2004 |
| WO | WO/2005/094812 | 10/2005 |
| WO | WO2006036024 | 4/2006 |
| WO | WO2006037766 A1 | 4/2006 |
| WO | WO/2007/023931 | 3/2007 |

(Continued)

OTHER PUBLICATIONS

JECFA ("Mannitol", http://www.fao.org/ag/agn/jecfa-additives/specs/Monograph1/Additive-275.pdf, 1996).*
PKa Table (2005, http://evans.harvard.edu/pdf/evans_pka_table.pdf).*
Havorka et al., J. Pharm. Sci., 2001, 90, 253-269.*
Wang et al. Stabilization of a polypeptide in non-aqueous solvents; International Journal of Pharmaceutics; vol. 351, Issues 1-2, Mar. 3, 2008, pp. 1-7.
PCT International Search Report PCT/JP2009/063708; Feb. 24, 2010.

(Continued)

Primary Examiner — Misook Yu
Assistant Examiner — Kauser M Akhoon
(74) Attorney, Agent, or Firm — Mintz Levin Cohn Ferris Glovsky and Popeo, P.C.; David G. Conlin; Joohee Lee

(57) ABSTRACT

The present invention provides a pharmaceutical composition or a solid preparation containing a stabilized pharmaceutically active ingredient and a stabilizing method thereof.

According to the present invention, a pharmaceutical composition can be stabilized by containing a nonpeptidic pharmaceutically active ingredient having a primary or secondary amino group, an excipient and an acidic compound. In addition, a solid preparation containing a pharmaceutically active ingredient, titanium oxide, a plasticizer and a chain organic acid can enhance the stability of the pharmaceutically active ingredient during light irradiation.

7 Claims, No Drawings

(56) References Cited

FOREIGN PATENT DOCUMENTS

| WO | WO2007/026916 A1 | 3/2007 |
|---|---|---|
| WO | PCT/JP2007/067706 | 3/2008 |
| WO | WO2008108380 A2 | 9/2008 |
| WO | WO2009041447 A1 | 4/2009 |
| WO | WO2009041705 A9 | 4/2009 |
| WO | PCT/JP2008/071168 | 5/2009 |

OTHER PUBLICATIONS

Kiyono, M.;(2000) "Titanium Oxide" property and applied technique; *Property and Application of Titanium Oxide* (published by Gihodo-shuppan Japan) pp. 175-182.

Manabu Kiyono, Titanium Oxide, Physicality and Applied Technology, Jun. 25, 1991 1st impession of the 1st edition; Jun. 20, 2003 5th ipression of the 1st edition, pp. 1-13.

Office Action issued in JP 2011-504079, mailed Nov. 20, 2012, and its English translation.

Kenneth C. Waterman, Roger C. Adami, Karen M. Alsante, Jinyang Hong, Margaret S. Landis, Franco Lombardo, Christopher J. Roberts; Stabilization of Pharmaceuticals to Oxidative Degradation; Pharmaceutical Development and Technology Jan. 2002, vol. 7, No. 1: 1-32.

Japanese Office Action 2011-504079; mailed Nov. 20, 2012.

Japanese Office Action, mailed on Nov. 12, 2013 in corresponding Japanese Patent Application No. 10-507659.

Office Action from the corresponding Colombian Patent Application No. 11-23140-A-1 mailed Oct. 16, 2013.

Ruotsalainen "Studies of Aqueous Film Coating of Tablets Performed in a Side-Vented Pan Coater", Academic Dissertation. Pharmaceutical Technology Division Department of Pharmacy University of Helsinki, Finland, presented on Jun. 27, 2003.

Office Action issued in corresponding Columbian Application Ser. No. 11023140, Nov. 25, 2014, 9 pages.

\* cited by examiner

PHARMACEUTICAL COMPOSITION

This application is a National Stage of PCT/JP2009/063708, filed on Jul. 27, 2009, which claims priority to Japanese Patent Application No. 2008-194219, filed on Jul. 28, 2008. The entire contents of these application are incorporated herein by reference.

TECHNICAL FIELD OF THE INVENTION

The present invention relates to a stabilized pharmaceutical composition comprising a nonpeptidic pharmaceutically active ingredient having a primary or secondary amino group, an excipient and an acidic compound, and a stabilizing method thereof.

Furthermore, the present invention relates to a solid preparation improved in the stability during light irradiation, which comprises a pharmaceutically active ingredient, titanium oxide, a plasticizer and a chain organic acid, and a stabilizing method thereof.

BACKGROUND OF THE INVENTION

The "nonpeptidic pharmaceutically active ingredient having a primary or secondary amino group" is widely used as a pharmaceutically active ingredient for various diseases. For example, patent document 1 describes a compound represented by the following formula and a salt thereof as agents for the treatment or prophylaxis of peptic ulcer, gastritis, erosive esophagitis and the like.

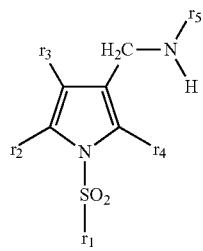

wherein $r_1$ is a monocyclic nitrogen-containing heterocyclic group optionally condensed with a benzene ring or a heterocycle, the monocyclic nitrogen-containing heterocyclic group optionally condensed with a benzene ring or a heterocycle optionally has substituent(s), $r_2$ is an optionally substituted $C_{6-14}$ aryl group, an optionally substituted thienyl group or an optionally substituted pyridyl group, $r_3$ and $r_4$ are each a hydrogen atom, or one of $r_3$ and $r_4$ is a hydrogen atom, and the other is an optionally substituted lower alkyl group, an acyl group, a halogen atom, a cyano group or a nitro group, and $r_5$ is an alkyl group.

Patent document 2 describes a proton pump inhibitor (PPI) comprising a compound represented by the following formula or a salt thereof, or a prodrug thereof as an agent for the treatment or prophylaxis of peptic ulcer, gastritis, erosive esophagitis and the like.

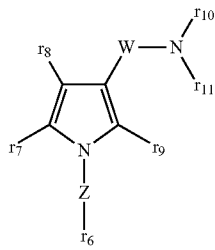

wherein Z and W are the same or different and each is a bond or a spacer having 1 to 20 atoms in the main chain, $r_6$ is an optionally substituted hydrocarbon group or an optionally substituted heterocyclic group, $r_7$, $r_8$ and $r_9$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $r_{10}$ and $r_{11}$ are the same or different and each is a hydrogen atom or an optionally substituted hydrocarbon group.

Patent document 3 describes N-(1-octyl-5-carboxymethyl-4,6-dimethylindolin-7-yl)-2,2-dimethylpropaneamide (the following formula) or a pharmacologically acceptable salt thereof as an active ingredient of a stabilized pharmaceutical composition containing an indoline compound.

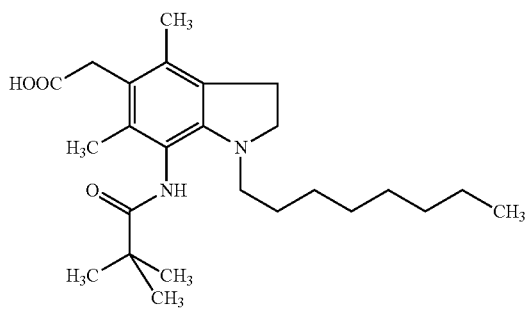 [SMILES: CCCCCCCCN1CCc2c(C)c(CC(=O)O)c(C)c(NC(=O)C(C)(C)C)c21]

Patent document 4 describes, as an improved preparation for oral use of a compound, a pharmaceutical composition for oral administration, which comprises at least a) ethyl 3-[(2-{[4-(hexyloxycarbonylamino-imino-methyl)-phenylamino]-methyl}-1-methyl-1H-benzoimidazole-5-carbonyl)-pyridin-2-yl-amino]-propionate represented by the following formula or one of the pharmaceutically acceptable salts thereof and b) one or more pharmaceutically acceptable organic acids having water-solubility higher than 1 g/250 ml at 20° C.

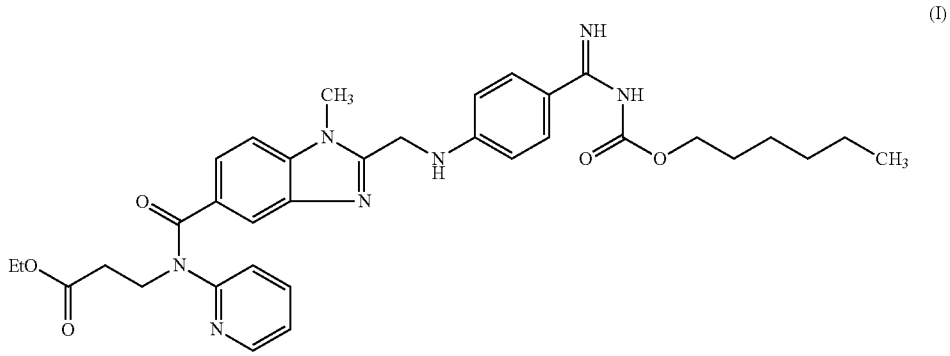 [SMILES: CCCCCCOC(=O)NC(=N)c1ccc(NCc2nc3cc(C(=O)N(CCC(=O)OCC)c4ccccn4)ccc3n2C)cc1]

On the other hand, regarding a stabilizer of a pharmaceutically active ingredient in a pharmaceutical composition, patent document 5 discloses an aqueous pharmaceutical solution comprising an aqueous solution containing an organic acid salt of a polymyxin antibiotic and carboxylic acid (organic acid, as a stabilizer).

In addition, non-patent document 1 describes, for stabilization of peptide (P66) in a nonaqueous solvent, acidification of peptide by addition of HCl, TFA, $H_3PO_4$ and the like.

Beside the above, patent document 6 describes a pharmaceutical composition comprising a proton pump antagonist (acid pump antagonist, APA) and one or more basic excipients to stabilize APA, and patent document 7 describes a sustained-release pharmaceutical composition comprising reversible PPI, wherein APA is stabilized with one or more basic excipients (carbonate, magnesium salt etc.).

Patent document 8 discloses a stabilized pharmaceutical preparation coated with a coating agent containing a) a light shielding agent capable of generating free radical by UV light, and b) a free radical scavenger. In addition, as the light shielding agent capable of generating free radical by UV light, metal oxides such as titanium oxide and the like are described, and as the free radical scavenger, for example, organic acids such as benzoic acid and the like are described.

In addition, non-patent document 2 describes the principles of photocatalytic reaction of titanium oxide, and explains the Honda Fujiyama effect that various substances adsorbed to a photocatalytic surface are oxidized and reduced when titanium oxide, which is one kind of the photocatalysts, is exposed to a light having a wavelength of 380 nm or below.

CITATION LIST

Patent Literature patent document 1: WO 2007/026916
patent document 2: WO 2006/036024
patent document 3: JP-A-2005-263788
patent document 4: JP-A-2007-056018
patent document 5: JP-A-3-44333 (JP-B-2844351)
patent document 6: WO 2004/089342
patent document 7: WO 2006/037766
patent document 8: JP-A-11-147819

Non Patent Literature non-patent document 1: International Journal of Pharmaceutics (Volume 351, Issues 1-2, 3 Mar. 2008, Pages 1-7), "Stabilization of a polypeptide in non-aqueous solvents"

non-patent document 2: titanium oxide (property and applied technique): Manabu Kiyono, GIHODO SHUPPAN Co., Ltd.

SUMMARY OF THE INVENTION

Problems to be Solved by the Invention

An object of the present invention is to provide a stabilized pharmaceutical composition for use of a nonpeptidic pharmaceutically active ingredient having a primary or secondary amino group as an active ingredient of a pharmaceutical composition and a stabilizing method thereof.

A further object of the present invention is to provide a solid preparation improved in the stability of a pharmaceutically active ingredient during light irradiation, for use of a pharmaceutically active ingredient as a solid active ingredient of a pharmaceutical composition, and a stabilizing method thereof.

Means of Solving the Problems

The present inventors have conducted intensive studies of stabilization of a pharmaceutical composition and found that the stability of a pharmaceutical composition (pharmaceutically active ingredient) can be further increased by adding an acidic compound (e.g., particular organic acid) to a pharmaceutical composition comprising a nonpeptidic pharmaceutically active ingredient having a primary or secondary amino group, which resulted in the completion of a first invention of the present invention. In addition, they have conducted intensive studies of photostabilization of a pharmaceutical composition and found that the stability of a pharmaceutically active ingredient during light irradiation can be improved by adding titanium oxide and a chain organic acid to a solid preparation comprising the pharmaceutically active ingredient, which resulted in the completion of a second invention.

Accordingly, the first invention of the present invention relates to

[1] a stabilized pharmaceutical composition comprising a nonpeptidic pharmaceutically active ingredient having a primary or secondary amino group, an excipient and an acidic compound,

[2] the pharmaceutical composition of the above-mentioned [1], wherein the acidic compound is an organic acid or a salt thereof,

[3] the pharmaceutical composition of the above-mentioned [2], wherein the nonpeptidic pharmaceutically active ingredient has a pKa value higher than that of the organic acid or a salt thereof,

[4] the pharmaceutical composition of the above-mentioned [1], wherein the nonpeptidic pharmaceutically active ingredient is an organic acid salt,

[5] the pharmaceutical composition of the above-mentioned [1], wherein the excipient has pH 4.5 or above when dissolved or dispersed in water,

[6] the pharmaceutical composition of the above-mentioned [1], wherein the excipient is any one kind or more selected from the group consisting of mannitol, croscarmellose sodium, hydroxypropylcellulose, hydroxypropylmethylcellulose, polyethylene glycol, polyvinylpyrrolidone, crystalline cellulose, lactose, sucrose, starch, cornstarch, titanium oxide ($TiO_2$) and light anhydrous silicic acid,

[7] the pharmaceutical composition of the above-mentioned [1], wherein the nonpeptidic pharmaceutically active ingredient is a salt with an unsaturated carboxylic acid,

[8] the pharmaceutical composition of the above-mentioned [2], wherein the organic acid is any one kind or more selected from the group consisting of adipic acid, ascorbic acid, benzoic acid, oleic acid, succinic acid, acetic acid, tartaric acid, sorbic acid, fumaric acid, lactic acid, maleic acid, malonic acid, citric acid and malic acid,

[9] the pharmaceutical composition of the above-mentioned [1], wherein the nonpeptidic pharmaceutically active ingredient is a compound represented by the formula $$R^a - N - H$$
$$\phantom{R^a - N -}|$$
$$\phantom{R^a - N -}R^b$$

wherein $R^a$ is an organic residue, $R^b$ is a hydrogen atom or a hydrocarbon group optionally having substituent(s), or a salt thereof,

[10] the pharmaceutical composition of the above-mentioned [1], wherein the nonpeptidic pharmaceutically active ingredient is a compound represented by the formula

[structure showing pyrrole with substituents $R^2$, $R^3$, $R^4$, $R^5$, X, Y, $R^1$]

wherein X and Y are the same or different and each is a bond or a spacer having 1 to 20 atoms in the main chain, $R^1$ is an optionally substituted hydrocarbon group or an optionally substituted heterocyclic group, $R^2$, $R^3$ and $R^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $R^5$ is a hydrogen atom or an optionally substituted hydrocarbon group,
or a salt thereof,

[11] the pharmaceutical composition of the above-mentioned [1], wherein the nonpeptidic pharmaceutically active ingredient is 1-{5-(2-fluorophenyl)-1-[(6-methylpyridin-3-yl)sulfonyl]-1H-pyrrol-3-yl}-N-methylmethanamine or a salt thereof, 1-[4-fluoro-5-phenyl-1-(pyridin-3-ylsulfonyl)-1H-pyrrol-3-yl]-N-methylmethanamine or a salt thereof, N-methyl-1-[5-(4-methyl-3-thienyl)-1-(pyridin-3-ylsulfonyl)-1H-pyrrol-3-yl]methanamine or a salt thereof, 1-[(5-(2-fluorophenyl)-1-(pyridin-3-ylsulfonyl)-1H-pyrrol-3-yl]-N-methylmethanamine or a salt thereof, N-methyl-1-[5-(2-methylphenyl)-1-(pyridin-3-ylsulfonyl)-1H-pyrrol-3-yl]methanamine or a salt thereof, or 1-[4-fluoro-5-(2-fluoropyridin-3-yl)-1-(pyridin-3-ylsulfonyl)-1H-pyrrol-3-yl]-N-methylmethanamine or a salt thereof,

[12] the pharmaceutical composition of the above-mentioned [1], which is a solid preparation, and

[13] a method of stabilizing a pharmaceutical composition comprising a nonpeptidic pharmaceutically active ingredient having a primary or secondary amino group and an excipient, comprising adding an acidic compound to the pharmaceutical composition.

In addition, the second invention of the present invention relates to

[14] a solid preparation improved in the stability during light irradiation, comprising a pharmaceutically active ingredient, titanium oxide, a plasticizer and a chain organic acid,

[15] the solid preparation of the above-mentioned [14], wherein the plasticizer is represented by the formula $$HOCH_2(CH_2OCH_2)_nCH_2OH$$

(n=an integer of 2-870),

[16] the solid preparation of the above-mentioned [14], wherein the plasticizer is polyethylene glycol (PEG),

[17] the solid preparation of the above-mentioned [14], wherein the chain organic acid has pH 6.0 or below when dissolved or dispersed in water,

[18] the solid preparation of the above-mentioned [14], wherein the chain organic acid has an acid dissociation constant (pKa) of a proton complex of 4.0 or below when dissolved or dispersed in water,

[19] the solid preparation of the above-mentioned [14], wherein the chain organic acid is any one kind or more selected from the group consisting of adipic acid, oleic acid, succinic acid, acetic acid, tartaric acid, sorbic acid, fumaric acid, lactic acid, maleic acid, malonic acid, citric acid and malic acid,

[20] the solid preparation of the above-mentioned [14], wherein the content (%) of the chain organic acid is 0.01-50 wt %,

[21] the solid preparation of the above-mentioned [14], wherein the pharmaceutically active ingredient is a compound represented by the formula

[structure showing pyrrole with substituents $R^2$, $R^3$, $R^4$, $R^5$, X, Y, $R^1$]

wherein X and Y are the same or different and each is a bond or a spacer having 1 to 20 atoms in the main chain, $R^1$ is an optionally substituted hydrocarbon group or an optionally substituted heterocyclic group, $R^2$, $R^3$ and $R^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $R^5$ is a hydrogen atom or an optionally substituted hydrocarbon group,
or a salt thereof,

[22] the solid preparation of the above-mentioned [14], wherein the pharmaceutically active ingredient is 1-{5-(2-fluorophenyl)-1-[(6-methylpyridin-3-yl)sulfonyl]-1H-pyrrol-3-yl}-N-methylmethanamine or a salt thereof, 1-[4-fluoro-5-phenyl-1-(pyridin-3-ylsulfonyl)-1H-pyrrol-3-yl]-N-methylmethanamine or a salt thereof, N-methyl-1-[5-(4-methyl-3-thienyl)-1-(pyridin-3-ylsulfonyl)-1H-pyrrol-3-yl]methanamine or a salt thereof, 1-[5-(2-fluorophenyl)-1-(pyridin-3-ylsulfonyl)-1H-pyrrol-3-yl]-N-methylmethanamine or a salt thereof, N-methyl-1-[5-(2-methylphenyl)-1-(pyridin-3-ylsulfonyl)-1H-pyrrol-3-yl]methanamine or a salt thereof, or 1-[4-fluoro-5-(2-fluoropyridin-3-yl)-1-(pyridin-3-ylsulfonyl)-1H-pyrrol-3-yl]-N-methylmethanamine or a salt thereof, and

[23] a method of stabilizing a solid preparation comprising a pharmaceutically active ingredient, titanium oxide and a plasticizer during light irradiation, comprising adding a chain organic acid to the solid preparation.

Effect of the Invention

According to the first invention of the present invention, a stabilized pharmaceutical composition comprising a nonpeptidic pharmaceutically active ingredient having a primary or secondary amino group is provided. To be specific, since development of a decomposed product of the pharmaceutically active ingredient (nonpeptidic one having a primary or secondary amino group) in the pharmaceutical composition is suppressed, a more stable pharmaceutical composition is provided. According to the present invention, moreover, since development of a decomposed product of the pharmaceutically active ingredient is suppressed regardless of being in a closed bottle/open bottle, a pharmaceutical composition also superior in the preservation stability can be provided.

In addition, according to the second invention of the present invention, a solid preparation improved in the stability of a pharmaceutically active ingredient to light irradiation is provided. To be specific, a solid preparation stable to light irradiation can be provided by, when the pharmaceutically active ingredient contained in the solid preparation is exposed to light, shielding the light and suppressing an increase in a decomposed product.

DETAILED DESCRIPTION OF THE INVENTION

Firstly, the first invention of the present invention is explained in detail by referring to specific embodiments.

The pharmaceutical composition relating to the first invention of the present invention is characterized by addition of an acidic compound (third component) to a pharmaceutical composition containing a nonpeptidic pharmaceutically active ingredient having a primary or secondary amino group (first component) and an excipient (second component). That is, the composition contains at least a nonpeptidic pharmaceutically active ingredient having a primary or secondary amino group, an excipient and an acidic compound.

[1. Nonpeptidic Pharmaceutically Active Ingredient Having a Primary or Secondary Amino Group (First Component)]

Examples of the first component, "nonpeptidic pharmaceutically active ingredient having a primary or secondary amino group", in the pharmaceutical composition of the present invention include a compound represented by the following formula or a salt thereof. The compound represented by the formula (A1) and a salt thereof do not include a compound having an amide group and a salt thereof.

(A1)

wherein $R^a$ is an organic residue, and $R^b$ is a hydrogen atom or a hydrocarbon group optionally having substituent(s).

In the formula (A1), the "organic residue" for $R^a$ is a monovalent group having 1 to 700 carbon atoms, and may contain, besides a carbon atom, a hydrogen atom, a nitrogen atom, an oxygen atom, a sulfur atom, a halogen atom (e.g., fluorine atom, chlorine atom, bromine atom, iodine atom etc.) and the like. The "organic residue" is a hydrocarbon group optionally having substituent(s). Here, examples of the "hydrocarbon group optionally having substituent(s)" include those similar to the "optionally substituted hydrocarbon group" for the below-mentioned $R^{40}$. When the hydrocarbon group has two or more substituents, they may form a ring.

Examples of the "hydrocarbon group optionally having substituent(s)" for $R^b$ in the formula (A1) include those similar to the "optionally substituted hydrocarbon group" for $R^5$ in a compound represented by the following (A2) to be described in detail in the following.

In the nonpeptidic pharmaceutically active ingredient having a primary or secondary amino group, which is represented by the formula (A1), the more preferred are, for example, a compound represented by the following formula (A1') and a salt thereof.

(A1')

wherein $R^C$ is an organic residue, and Y is a bond or a spacer having 1 to 20 atoms in the main chain.

In the above-mentioned formula (A1'), the "organic residue" for $R^c$ is as defined above.

In the above-mentioned formula (A1'), examples of the "spacer having 1 to 20 atoms in the main chain" for Y include those similar to Y in a compound represented by the following (A2).

Preferable examples of the above-mentioned nonpeptidic pharmaceutically active ingredients having a primary or secondary amino group include a compound disclosed in WO 2006/036024 represented by the following formula (A2) and a salt thereof.

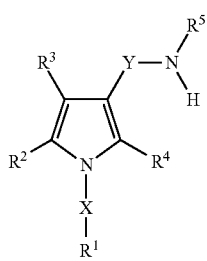

(A2)

wherein X and Y are the same or different and each is a bond or a spacer having 1 to 20 atoms in the main chain, $R^1$ is an optionally substituted hydrocarbon group or an optionally substituted heterocyclic group, $R^2$, $R^3$ and $R^4$ are the same or different and each is a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, and $R^5$ is a hydrogen atom or an optionally substituted hydrocarbon group.

In the formula (A2), the "spacer having 1 to 20 atoms in the main chain" for X or Y means a divalent group having 1 to 20 contiguous atoms in the main chain. Here, the "number of atoms in the main chain" is counted such that the number of atoms in the main chain becomes minimum.

As the "spacer having 1 to 20 atoms in the main chain", for example, a divalent group that can be formed with 1 to 5 (preferably 1 to 3) contiguous groups selected from
—O—;
—S—;
—CO—;
—SO—;
—SO$_2$—;
—NR$^{40}$— (wherein $R^{40}$ is a hydrogen atom, an optionally substituted hydrocarbon group, an optionally substituted (e.g., halogenated) $C_{1-6}$ alkyl-carbonyl, or an optionally substituted (e.g., halogenated) $C_{1-6}$ alkylsulfonyl); and a divalent $C_{1-6}$ aliphatic hydrocarbon group optionally having substituent(s)
and the like can be mentioned.

As the "hydrocarbon group" of the "optionally substituted hydrocarbon group" for $R^{40}$, for example, a chain or cyclic hydrocarbon group (e.g., alkyl, alkenyl, alkynyl, cycloalkyl, aryl, aralkyl etc.) can be mentioned. Of these, a chain or cyclic hydrocarbon group having 1 to 16 carbon atoms and the like are preferable.

As the "alkyl", for example, $C_{1-6}$ alkyl (e.g., methyl, ethyl, propyl, isopropyl, butyl, isobutyl, sec-butyl, tert-butyl, pentyl, hexyl etc.) and the like can be mentioned.

As the "alkenyl", for example, $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like can be mentioned.

As the "alkynyl", for example, $C_{2-6}$ alkynyl (e.g., ethynyl, propargyl, 1-butynyl, 2-butynyl, 3-butynyl, 1-hexynyl etc.) and the like can be mentioned.

As the "cycloalkyl", for example, $C_{3-7}$ cycloalkyl (e.g., cyclopropyl, cyclobutyl, cyclopentyl, cyclohexyl, cycloheptyl etc.) and the like can be mentioned.

As the "aryl", for example, $C_{6-14}$ aryl (e.g., phenyl, 1-naphthyl, 2-naphthyl, 2-biphenylyl, 3-biphenylyl, 4-biphenylyl, 2-anthryl etc.) and the like can be mentioned.

As the "aralkyl", for example, $C_{7-16}$ aralkyl (e.g., phenyl-$C_{1-6}$ alkyl, naphthyl-$C_{1-6}$ alkyl or diphenyl-$C_{1-4}$ alkyl etc. such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like can be mentioned.

When the above-mentioned hydrocarbon group is an alkyl, an alkenyl or an alkynyl, the hydrocarbon group is optionally substituted by 1 to 3 substituents selected from (1) a halogen atom (e.g., a fluorine atom, a chlorine atom, a bromine atom, an iodine atom etc.), (2) nitro, (3) cyano, (4) hydroxy, (5) $C_{1-6}$ alkoxy optionally having 1 to 3 halogen atoms (e.g., a fluorine atom, a chlorine atom, a bromine atom, an iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., a fluorine atom, a chlorine atom, a bromine atom, an iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), and (49) $C_{3-7}$ cycloalkyl (e.g., cyclopropyl, cyclobutyl, cyclopentyl, cyclohexyl, cycloheptyl etc.) (hereinafter to be referred to as substituent group A) and the like. The substituent may have 1 to 4 substituents at substitutable position. Examples of such substituent include those similar to substituents in substituent group A.

When the above-mentioned hydrocarbon group is a cycloalkyl, an aryl or an aralkyl, the hydrocarbon group is optionally substituted by 1 to 5 (preferably 1 to 3) substituents selected from (1) a halogen atom (e.g., a fluorine atom, a chlorine atom, a bromine atom, an iodine atom etc.), (2) nitro, (3) cyano, (4) hydroxy, (5) $C_{1-6}$ alkoxy optionally having 1 to 3 halogen atoms (e.g., a fluorine atom, a chlorine atom, a bromine atom, an iodine atom) (e.g., methoxy, ethoxy, propoxy, isopropoxy, butoxy, isobutoxy, sec-butoxy, pentyloxy, hexyloxy, fluoromethoxy etc.), (6) $C_{6-19}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., a fluorine atom, a chlorine atom, a bromine atom, an iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl optionally having 1 to 3 halogen atoms (e.g., a fluorine atom, a chlorine atom, a bromine atom, an iodine atom) (e.g., methylsulfonyl, ethylsulfonyl, trifluoromethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., a fluorine atom, a chlorine atom, a bromine atom, an iodine atom) or hydroxy groups, (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., a fluorine atom, a chlorine atom, a bromine atom, an iodine atom), (52) a $C_{2-6}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), and (54) a 5 to 10-membered heterocyclyl-carbonyl containing, besides carbon atom, one or two kinds of 1 to 4 hetero atoms selected from a nitrogen atom, a sulfur atom and an oxygen atom (e.g., 4-morpholinocarbonyl etc.) (hereinafter to be referred to as substituent group B) and the like.

In the present specification, the substituent of the "optionally substituted hydrocarbon group" does not include an oxo group.

As the "optionally halogenated $C_{1-6}$ alkyl-carbonyl" for $R^{40}$, for example, $C_{1-6}$ alkyl-carbonyl optionally having 1 to 5, preferably 1 to 3 halogen atoms (e.g., a fluorine atom, a chlorine atom, a bromine atom, an iodine atom and the like) at substitutable positions and the like can be mentioned. Specific examples include, for example, acetyl, monochloroacetyl, trifluoroacetyl, trichloroacetyl, propanoyl, butanoyl, pentanoyl, hexanoyl and the like.

As the "optionally halogenated $C_{1-6}$ alkylsulfonyl" for $R^{40}$, for example, $C_{1-6}$ alkylsulfonyl optionally having 1 to 5, preferably 1 to 3 halogen atoms (e.g., a fluorine atom, a chlorine atom, a bromine atom, an iodine atom and the like) at substitutable positions and the like can be mentioned. Specific examples include, for example, methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, sec-butylsulfonyl, tert-butylsulfonyl, pentylsulfonyl, hexylsulfonyl and the like.

As the "divalent $C_{1-6}$ aliphatic hydrocarbon group" of the aforementioned "divalent $C_{1-6}$ aliphatic hydrocarbon group optionally having substituent(s)", an alkylene group, an alkenylene group, an alkynylene group can be mentioned, for example,
(1) a $C_{1-6}$ alkylene (e.g., —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$(CH(CH_3))_2$—, —$(CH_2)_2C(CH_3)_2$—, —$(CH_2)_3C(CH_3)_2$— and the like);
(2) a $C_{2-6}$ alkenylene (e.g., —CH=CH—, —$CH_2$—CH=CH—, —CH=CH—$CH_2$—, —CH=CH—$CH_2$—$CH_2$—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— and the like);
(3) a $C_{2-6}$ alkynylene (e.g., —C≡C—, —$CH_2$—C≡C—, —$CH_2$—C≡C—$CH_2$—$CH_2$— and the like) and the like can be mentioned.

As the "substituent" of the "divalent $C_{1-6}$ aliphatic hydrocarbon group optionally having substituent(s)", for example, those similar to the substituents of the alkyl, alkenyl or alkynyl exemplified as the aforementioned "optionally substituted hydrocarbon group" for $R^{40}$, can be mentioned, particularly, halogen atom (e.g., a fluorine atom, a chlorine atom, a bromine atom, an iodine atom), hydroxy and the like are preferable. The number of the substituents is, for example, 1 to 5, preferably 1 to 3.

As preferable examples of the "spacer having 1 to 20 atoms in the main chain"
(1) an optionally substituted alkylene group:
specifically, a $C_{1-20}$ alkylene (e.g., —$CH_2$—, —$(CH_2)_2$—, —$(CH_2)_3$—, —CH(OH)—$(CH_2)_2$—, —$(CH_2)_4$—, —$(CH_2)_5$—, $(CH_2)_6$—, —$CHCH_3$—, —$C(CH_3)_2$—, —$CH(CF_3)$—, —$(CH(CH_3))_2$—, —$(CF_2)_2$—, —$(CH_2)_2C(CH_3)_2$—, —$(CH_2)_3C(CH_3)_2$—, —$(CH_2)_7$—, —$(CH_2)_8$—, —$(CH_2)_9$—, —$(CH_2)_{10}$—, —$(CH_2)_{11}$—, —$(CH_2)_{12}$—, —$(CH_2)_{13}$—, —$(CH_2)_{14}$—, —$(CH_2)_{15}$—, —$(CH_2)_{16}$—, —$(CH_2)_{17}$—, —$(CH_2)_{18}$—, —$(CH_2)_{19}$—, —$(CH_2)_{20}$— and the like) optionally having 1 to 3 substituents (preferably, halogen atom, hydroxy and the like); (2) an optionally substituted alkenylene group:
specifically, a $C_{2-20}$ alkenylene (e.g., —CH=CH—, —$CH_2$—CH=CH—, —CH=CH—$CH_2$—, —CH=CH—$CH_2$—$CH_2$—, —$CH_2$—CF=CH—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— and the like) optionally having 1 to 3 substituents (preferably, halogen atom, hydroxy and the like);
(3) an optionally substituted alkynylene group:
specifically, a $C_{2-20}$ alkynylene (e.g., —C≡C—, —$CH_2$—C≡C—, —$CH_2$—C≡C—$CH_2$—$CH_2$— and the like) optionally having 1 to 3 substituents (preferably, halogen atom, hydroxy and the like); (4) —$(CH_2)_{w1a}O(CH_2)_{w2a}$—, —$(CH_2)_{w1a}S(CH_2)_{w2a}$—, —$(CH_2)_{w1a}CO(CH_2)_{w2a}$—, —$(CH_2)_{w1a}SO(CH_2)_{w2a}$—, —$(CH_2)_{w1a}SO_2(CH_2)_{w2a}$—, —$(CH_2)_{w1a}NR^{40}(CH_2)_{w2a}$—; (5) —$(CH_2)_{w3a}CO$—, —$(CH_2)_{w3a}CONR^{40}(CH_2)_{w4a}$—, —$(CH_2)_{w3a}NR^{40}CO$ $(CH_2)_{w4a}$—, —$(CH_2)_{w3a}SO_2NR^{40}(CH_2)_{w4a}$—, —$(CH_2)_{w3a}NR^{40}SO_2(CH_2)_{w4a}$—, —$(CH_2)_{w3a}COO(CH_2)_{w4a}$—; (6) —$(CH_2)_{w5a}NR^{40}CONR^{40b}(CH_2)_{w6a}$—;
wherein $R^{40}$ is as defined above; $R^{40b}$ is as defined as $R^{40}$; w1a and w2a are each an integer of 0 to 19, and w1a+w2a is 0 to 19; w3a and w4a are each an integer of 0 to 18, and w3a+w4a is 0 to 18; w5a and w6a are each an integer of 0 to 17, and w5a+w6a is 0 to 17,
and the like can be mentioned.

As the aforementioned "spacer having 1 to 20 atoms in the main chain", the following "spacer having 1 to 8 atoms in the main chain" is preferable.
(1) a $C_{1-8}$ alkylene optionally having 1 to 3 substituents (preferably, halogen atom, hydroxy and the like) (e.g., —$CH_2$—, —$(CH_2)_2$—, —$(CH_2)_3$—, —CH(OH)—$(CH_2)_2$—, $(CH_2)_4$—, $(CH_2)_5$—, $(CH_2)_6$—, —$CHCH_3$—, —$C(CH_3)_2$—, —$CH(CF_3)$—, —$(CH(CH_3))$ $(CF_2)_2$—, —$(CH_2)_2C(CH_3)_2$—, —$(CH_2)_3C(CH_3)_2$— and the like); (2) a $C_{2-8}$ alkenylene optionally having 1 to 3 substituents (preferably, halogen atom, hydroxy and the like) (e.g., —CH=CH—, —$CH_2$—CH=CH—, —CH=CH—$CH_2$—, —CH=CH—$CH_2$—$CH_2$—, —$CH_2$—CF=CH—, —$C(CH_3)_2$—CH=CH—, —$CH_2$—CH=CH—$CH_2$—, —$CH_2$—$CH_2$—CH=CH—, —CH=CH—CH=CH—, —CH=CH—$CH_2$—$CH_2$—$CH_2$— and the like); (3) a $C_{2-8}$ alkynylene (e.g., —C≡C—, —$CH_2$—C≡C—, —$CH_2$—C≡C—$CH_2$—$CH_2$— and the like) optionally having 1 to 3 substituents (preferably, halogen atom, hydroxy and the like);
(4) —$(CH_2)_{w1}O(CH_2)_{w2}$—, —$(CH_2)_{w1}S(CH_2)_{w2}$—, —$(CH_2)_{w1}CO(CH_2)_{w2}$—, —$(CH_2)_{w1}SO(CH_2)_{w2}$—, —$(CH_2)_{w1}SO_2(CH_2)_{w2}$—, —$(CH_2)_{w1}NR^{40}(CH_2)_{w2}$—; (5) —$(CH_2)_{w3}CO$—, —$(CH_2)_{w3}CONR^{40}(CH_2)_{w4}$—, —$(CH_2)_{w3}NR^{40}CO(CH_2)_{w4}$—, —$(CH_2)_{w3}SO_2NR^{40}$ $(CH_2)_{w4}$—, —$(CH_2)_{w3}NR^{40}SO_2CH_2)_{w4}$—, —$(CH_2)_{w3}CO$ $(CH_2)_{w4}$—; (6) —$(CH_2)_{w5}NR^{40}CONR^{40b}(CH_2)_{w6}$—;
wherein $R^{40}$ is as defined above; $R^{40b}$ is as defined as $R^{40}$; w1 and w2 are each an integer of 0 to 5, and w1+w2 is 0 to 7; w3 and w4 are each an integer of 0 to 4, and w3+w4 is 0 to 6; w5 and w6 are each an integer of 0 to 3, and w5+w6 is 0 to 5, and the like can be mentioned.

The "spacer having 1 to 20 atoms in the main chain" is preferably the following (1) to (6).
(1) —$SO_2$—; (2) —$SO_2$—N($R^7$)— wherein $R^7$ is a hydrogen atom or an optionally substituted hydrocarbon group, and as the "optionally substituted hydrocarbon group" for $R^7$, those similar to the aforementioned "optionally substituted hydrocarbon group" for $R^{40}$ can be mentioned; (3) —N($R^8$)—$SO_2$— wherein $R^8$ is a hydrogen atom or an optionally substituted hydrocarbon group, and as the "optionally substituted hydrocarbon group" for $R^8$, those similar to the aforementioned "optionally substituted hydrocarbon group" for $R^{40}$ can be mentioned; (4) —N($R^9$)— wherein $R^9$ is a hydrogen atom or an optionally substituted hydrocarbon group, and as the "optionally substituted hydrocarbon group" for $R^9$, those similar to the aforementioned "optionally substituted hydrocarbon group" for $R^{40}$ can be mentioned; (5) —O—; (6) an optionally substituted alkylene group, preferably a $C_{1-8}$ alkylene optionally having 1 to 3 substituents (preferably, halogen atom, hydroxy and the like) (e.g., —$CH_2$—, —$(CH_2)_2$—, —$(CH_2)_3$—, —CH(OH)—$(CH_2)_2$—, —$(CH_2)_4$—, —$(CH_2)_5$—, —$(CH_2)_6$—, —$CHCH_3$—, —$C(CH_3)_2$—, —$CH(CF_3)$—, —$(CH(CH_3))_2$—, —$(CF_2)_2$—, —$(CH_2)_2C(CH_3)_2$—, —$(CH_2)_3C(CH_3)_2$— and the like).

In the formula (A2), X is preferably —SO$_2$—, —SO$_2$—N(R$^7$)— (wherein R$^7$ is as defined above), —N(R$^8$)—SO$_2$— (wherein R$^8$ is as defined above), —N(R$^9$)— (wherein R$^9$ is as defined above) or —O—, particularly preferably —SO$_2$—.

Y is preferably a bond or a C$_{1-8}$ alkylene (e.g., —CH$_2$—, —(CH$_2$)$_2$—, —(CH$_2$)$_3$—, —(CH$_2$)$_4$—, —(CH$_2$)$_5$—, —(CH$_2$)$_6$—, —CHCH$_3$—, —C(CH$_3$)$_2$—, —(CH(CH$_3$))$_2$—, —(CH$_2$)$_2$C(CH$_3$)$_2$—, —(CH$_2$)$_3$C(CH$_3$)$_2$— and the like).

In the aforementioned formula (A2), R$^1$ is an optionally substituted hydrocarbon group or an optionally substituted heterocyclic group.

As the "optionally substituted hydrocarbon group", those similar to the aforementioned "optionally substituted hydrocarbon group" for R$^{40}$ can be mentioned.

As the "heterocyclic group" of the "optionally substituted heterocyclic group", for example, a 3 to 8-membered heterocyclic group (preferably 5- or 6-membered heterocyclic group) containing 1 to 4 hetero atoms selected from a nitrogen atom (optionally oxidized), an oxygen atom, a sulfur atom (optionally mono- or di-oxidized) and the like; or a group formed by condensing a 3 to 8-membered heterocyclic group (preferably 5- or 6-membered heterocyclic group) containing 1 to 4 hetero atoms selected from a nitrogen atom (optionally oxidized), an oxygen atom, a sulfur atom (optionally mono- or di-oxidized) and the like, and a benzene ring or a 3 to 8-membered heterocyclic group (preferably 5- or 6-membered heterocyclic group) containing 1 to 4 hetero atoms selected from a nitrogen atom (option ally oxidized), an oxygen atom, a sulfur atom (optionally mono- or di-oxidized) and the like, preferably a group formed by condensing the 5- or 6-membered heterocyclic group and a 5- or 6-membered ring containing 1 to 4 hetero atoms selected from a nitrogen atom (optionally oxidized), an oxygen atom, a sulfur atom (optionally mono- or di-oxidized) and the like, can be mentioned.

To be specific, aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5 imidazolyl), triazolyl (e.g., 1,2,3-triazol-1-, 4- or -5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein the sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein the nitrogen atom is oxidized (e.g., 2-, 3- or 4-pyridyl-N-oxide), pyridazinyl (e.g., 3- or 4-pyridazinyl), pyridazinyl wherein one or both of the nitrogen atom is oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atoms is(are) oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indol-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein the sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl, 2,3-dihydro-1-benzofuranyl, 2,1,3-benzothiadiazolyl, 2,3-dihydro-1,4-benzodioxin-5- or -6-yl, 1,3-benzothiazol-6-yl, 1,1-dioxido-2,3-dihydro-1-benzothien-6-yl, 1-benzothienyl and the like can be used.

Examples of the "substituent" of the heterocyclic group include those similar to the substituents selected from the above-mentioned substituent group B. The number of the substituents is, for example, 1 to 5, preferably 1 to 3.

R$^1$ is preferably an optionally substituted alkyl group, an optionally substituted aryl group, an optionally substituted aralkyl group, an optionally substituted thienyl group or an optionally substituted pyridyl group, more preferably an optionally substituted alkyl group, an optionally substituted aryl group, an optionally substituted aralkyl group or an optionally substituted pyridyl group, particularly preferably an optionally substituted aryl group or an optionally substituted pyridyl group.

To be specific, R$^1$ is preferably [1] C$_{1-6}$ alkyl (e.g., methyl, ethyl, propyl, isopropyl, butyl, isobutyl, sec-butyl, tert-butyl, pentyl, hexyl etc.), [2] a C$_{6-14}$ aryl group (e.g., phenyl etc.) optionally substituted by 1 to 5 (preferably 1 to 3) substituents selected from (i) halogen (e.g., fluorine, chlorine, bromine, iodine), (ii) hydroxy, (iii) cyano, (iv) C$_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) C$_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine) and (vi) phenyl, or [3] an (unsubstituted) thienyl group or [4] an (unsubstituted) pyridyl group, particularly preferably a C$_{6-14}$ aryl group (e.g., phenyl etc.) optionally substituted by 1 to 5 (preferably 1 to 3) substituents selected from halogen, hydroxy and C$_{1-6}$ alkyl or an (unsubstituted) pyridyl group.

In the aforementioned formula (A2), R$^2$, R$^3$ and R$^4$ are the same or different and each is a hydrogen atom or an optionally substituted hydrocarbon group, an optionally substituted thienyl group, an optionally substituted benzo[b]thienyl group, an optionally substituted furyl group, an optionally substituted pyridyl group, an optionally substituted pyrazolyl group, an optionally substituted pyrimidinyl group, an acyl group, a halogen atom, a cyano group or a nitro group, preferably, a hydrogen atom or an optionally substituted hydrocarbon group, an optionally substituted thienyl group, an optionally substituted benzo[b]thienyl group, an optionally substituted furyl group, an optionally substituted pyridyl group, an acyl group, a halogen atom, a cyano group or a nitro group.

As the "optionally substituted hydrocarbon group" for R$^2$, R$^3$ or R$^4$, those similar to the aforementioned "optionally substituted hydrocarbon group" for R$^{40}$ can be mentioned.

As the "thienyl group" of the "optionally substituted thienyl group" for R$^2$, R$^3$ or R$^4$, 2- or 3-thienyl can be mentioned.

Examples of the "substituent" of the thienyl group include those similar to the substituents selected from the above-mentioned substituent group B. The number of the substituents is 1 to 3.

As the "benzo[b]thienyl group" of the "optionally substituted benzo[b]thienyl group" for R$^2$, R$^3$ or R$^4$, 2- or 3-benzo[b]thienyl can be mentioned.

Examples of the "substituent" of the benzo[b]thienyl group include those similar to the substituents selected from the above-mentioned substituent group B. The number of the substituents is, for example, 1 to 5, preferably 1 to 3.

As the "furyl group" of the "optionally substituted furyl group" for $R^2$, $R^3$ or $R^4$, 2- or 3-furyl can be mentioned.

Examples of the "substituent" of the furyl group include those similar to the substituents selected from the above-mentioned substituent group B. The number of the substituents is 1 to 3.

As the "pyridyl group" of the "optionally substituted pyridyl group" for $R^2$, $R^3$ or $R^4$, 2-, 3- or 4-pyridyl can be mentioned.

Examples of the "substituent" of the pyridyl group include those similar to the substituents selected from the above-mentioned substituent group B. The number of the substituents is 1 to 3.

As the "pyrazolyl group" of the "optionally substituted pyrazolyl group" for $R^2$, $R^3$ or $R^4$, 3- or 4-pyrazolyl can be mentioned.

Examples of the "substituent" of the pyrazolyl group include those similar to the substituents selected from the above-mentioned substituent group B. The number of the substituents is 1 to 3.

As the "pyrimidinyl group" of the "optionally substituted pyrimidinyl group" for $R^2$, $R^3$ or $R^4$, 2-, 4- or 5-pyrimidinyl can be mentioned.

Examples of the "substituent" of the pyrimidinyl group include those similar to the substituents selected from the above-mentioned substituent group B. The number of the substituents is 1 to 3.

As the "acyl group" for $R^2$, $R^3$ or $R^4$, an acyl group having 1 to 20 carbon atoms, which is derived from an organic carboxylic acid can be mentioned. For example, $C_{1-7}$ alkanoyl groups (e.g., formyl; $C_{1-6}$ alkyl-carbonyl such as acetyl, propionyl, butyryl, isobutyryl, pentanoyl, hexanoyl, heptanoyl and the like; etc.), $C_{6-14}$ aryl-carbonyl groups (e.g., benzoyl, naphthalenecarbonyl etc.), $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), $C_{6-14}$ aryloxy-carbonyl groups (e.g., phenoxycarbonyl group), $C_{7-19}$ aralkyl-carbonyl groups (e.g., phenyl-$C_{1-4}$ alkylcarbonyl such as benzylcarbonyl, phenethylcarbonyl, phenylpropylcarbonyl and the like, naphthyl-$C_{1-4}$ alkylcarbonyl such as benzhydrylcarbonyl, naphthylethylcarbonyl and the like, etc.), $C_{7-19}$ aralkyloxy-carbonyl groups (e.g., phenyl-$C_{1-4}$ alkyloxycarbonyl such as benzyloxycarbonyl and the like, etc.), 5- or 6-membered heterocyclyl-carbonyl group or condensed heterocyclyl-carbonyl groups thereof (e.g., pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein nitrogen atom is oxidized such as 2-, 3- or 4-pyridyl-N-oxidocarbonyl and the like; pyridazinylcarbonyl such as 3- or 4-pyridazinylcarbonyl and the like; pyridazinylcarbonyl wherein one or both nitrogen atoms are oxidized, such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both nitrogen atoms are oxidized, such as 2-, 4-, 5- or 6-pyrimidinyl-N-oxidocarbonyl and the like; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl (e.g., 1,5-naphthyridin-2- or 3-ylcarbonyl) such as 1,5-, 1,6-, 1,7-, 1,8-, 2,6- or 2,7-naphthyridinylcarbonyl and the like; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); a 5- or 6-membered heterocyclyl-carbonyl group (e.g., 5- or 6-membered heterocyclyl-carbonyl group containing 1 to 4 hetero atoms such as nitrogen atom (optionally oxidized), oxygen atom, sulfur atom (optionally mono or dioxidized) and the like, such as chromenylcarbonyl (e.g., 2H-chromen-2- or 3-ylcarbonyl etc.) and the like), a 5- or 6-membered heterocyclyl-acetyl group (e.g., 5- or 6-membered heterocyclyl-acetyl group containing 1 to 4 hetero atoms such as nitrogen atom (optionally oxidized), oxygen atom, sulfur atom (optionally mono or dioxidized) and the like, such as 2-pyrrolylacetyl, 3-imidazolylacetyl, 5-isoxazolylacetyl and the like, and the like) can be used.

As regards the substituent of acyl group, for example, when the above-mentioned acyl group is an alkanoyl group or alkoxy-carbonyl group, the acyl group is optionally substituted by 1 to 3 selected from alkylthio groups (e.g., $C_{1-4}$ alkylthio such as methylthio, ethylthio, n-propylthio, isopropylthio and the like, and the like), halogen (e.g., fluorine, chlorine, bromine, iodine), alkoxy groups (e.g., $C_{1-6}$ alkoxy such as methoxy, ethoxy, n-propoxy, tert-butoxy, n-hexyloxy and the like, and the like), a nitro group, alkoxy-carbonyl groups (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), alkylamino group (e.g., mono- or di-($n_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino and the like, and the like), alkoxyimino groups (e.g., $C_{1-6}$ alkoxyimino such as methoxyimino, ethoxyimino, n-propoxyimino, tert-butoxyimino, n-hexyloxy-imino and the like, and the like) and hydroxyimino.

When the above-mentioned acyl group is an aryl-carbonyl group, an aryloxy-carbonyl group, an aralkyl-carbonyl group, an aralkyloxycarbonyl group, a 5- or 6-membered heterocyclyl-carbonyl group or a 5- or 6-membered heterocyclyl-acetyl group, the acyl group is optionally substituted by 1 to 5 (preferably 1 to 3) selected from alkyl groups (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), alkenyl groups (e.g., $C_{2-6}$ alkenyl such as allyl, isopropenyl, isobutenyl, 1-methylallyl, 2-pentenyl, 2-hexenyl and the like, and the like), alkynyl groups (e.g., $C_{2-6}$ alkynyl such as propargyl, 2-butynyl, 3-butynyl, 3-pentynyl, 3-hexynyl and the like, and the like), alkoxy groups (e.g., $C_{1-6}$ alkoxy such as methoxy, ethoxy, n-propoxy, tert-butoxy, n-hexyloxy and the like, and the like), acyl groups [e.g., $C_{1-7}$ alkanoyl such as formyl, acetyl, propionyl, butyryl, isobutyryl, pentanoyl, hexanoyl, heptanoyl and the like; $C_{6-14}$ aryl-carbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, halogen (e.g., fluorine, chlorine, bromine, iodine), and alkylthio groups ($C_{1-4}$ alkylthio such as methylthio, ethylthio, n-propylthio, isobutylthio and the like, and the like).

As the "halogen atom" for $R^2$, $R^3$ or $R^4$, fluorine atom, chlorine atom, bromine atom and iodine atom can be mentioned.

$R^2$ is preferably a hydrogen atom, an optionally substituted hydrocarbon group, an optionally substituted thienyl group, an optionally substituted benzo[b]thienyl group, an optionally substituted furyl group, an optionally substituted pyridyl group, an optionally substituted pyrazolyl group or an optionally substituted pyrimidinyl group, more preferably a hydrogen atom, an optionally substituted hydrocarbon group, an optionally substituted thienyl group, an optionally substituted benzo[b]thienyl group, an optionally substituted furyl group or an optionally substituted pyridyl group, further more preferably a hydrogen atom, an optionally substituted hydrocarbon group or an optionally substituted pyridyl group, particularly preferably a hydrogen atom, an optionally substituted aryl group or an optionally substituted pyridyl group.

To be specific, $R^2$ is preferably

[1] a hydrogen atom, [2] $C_{6-14}$ aryl group (e.g., phenyl group) optionally substituted by 1 to 5 (preferably 1 to 3) substituents selected from (i) a halogen atom (e.g., a fluorine atom, a chlorine atom, a bromine atom, an iodine atom), (ii) cyano, (iii) amino optionally substituted by 1 or 2 selected from $C_{1-6}$ alkyl (e.g., methyl, ethyl etc.) and acetyl, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) phenoxy, (vii) $C_{1-6}$ alkylthio (e.g., methylthio, ethylthio etc.) optionally substituted by 1 to 5 (preferably 1 to 3) halogens (e.g., fluorine, chlorine, bromine, iodine), (viii) acetyl and (ix) aminocarbonyl, or [3] thienyl group, benzo[b]thienyl group, furyl group, pyridyl group, pyrazolyl group or pyrimidinyl group, each of which is optionally substituted by 1 to 3 substituents selected from halogen (e.g., fluorine, chlorine, bromine, iodine), $C_{1-6}$ alkoxy (e.g., methoxy, ethoxy etc.) and $C_{1-6}$ alkyl (e.g., methyl, ethyl, n-propyl, isobutyl etc.) (preferably 1 to 3 $C_{1-6}$ alkoxy) [preferably thienyl group, benzo[b]thienyl group, furyl group or pyridyl group, each of which is optionally substituted by 1 to 3 $C_{1-6}$ alkoxy], particularly preferably [1] (i) a hydrogen atom or (ii) a $C_{6-19}$ aryl group (e.g., phenyl group) optionally substituted by 1 to 5 (preferably 1 to 3) halogens atoms (e.g., a fluorine atom, a chlorine atom, a bromine atom, an iodine atom) or [2] a pyridyl group optionally substituted by 1 to 3 halogen atoms (e.g., a fluorine atom, a chlorine atom, a bromine atom, an iodine atom).

$R^3$ and $R^4$ are preferably the same or different and each is a hydrogen atom or an optionally substituted hydrocarbon group, an acyl group, a halogen atom, a cyano group or a nitro group.

Of these, a hydrogen atom, a $C_{1-6}$ alkyl group (e.g., methyl, ethyl, n-propyl, isobutyl etc.), a $C_{6-14}$ aryl group (e.g., phenyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group and a nitro group are preferable, particularly, a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., a fluorine atom, a chlorine atom, a bromine atom, an iodine atom), a cyano group and a nitro group are preferable.

In the aforementioned formula (A2), $R^5$ is a hydrogen atom or an optionally substituted hydrocarbon group.

Examples of the "optionally substituted hydrocarbon group" for $R^5$ include those similar to the "optionally substituted hydrocarbon group" for the aforementioned $R^{40}$.

As $R^5$, particularly, a $C_{1-6}$ alkyl group (e.g., methyl, ethyl, n-propyl, isobutyl etc.) is preferable.

When the compound represented by the above-mentioned formula (A2) has isomers such as optical isomer, stereoisomer, positional isomer, rotational isomer and the like, and any isomers and mixtures are encompassed in the compound (A2). For example, when compound (A2) has an optical isomer, an optical isomer separated from a racemate is also encompassed in the compound (A2). These isomers can be obtained as independent products by a synthesis means or a separation means (e.g., concentration, solvent extraction, column chromatography, recrystallization and the like), and the like known per se.

The compound (A2) may be a crystal, and both a single crystal and crystal mixtures are encompassed in the compound (A2). Crystals can be produced by crystallization according to crystallization methods known per se.

The compound (A2) may be a solvate (e.g., hydrate etc.) or a non-solvate, both of which are encompassed in the compound (A2).

A compound labeled with an isotope (e.g., $^3H$, $^{14}C$, $^{125}I$ and the like) is also encompassed in the compound (A2).

A compound represented by the above-mentioned formula (A2) can be produced, for example, according to the method described in WO 2006/036024.

In addition, preferable examples of the nonpeptidic pharmaceutically active ingredient having a primary or secondary amino group include the compound disclosed in WO 2007/026916, which is represented by the following formula (A3), and a salt thereof.

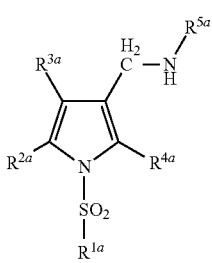

(A3)

wherein $R^{1a}$ is a nitrogen-containing monocyclic heterocyclic group optionally condensed with a benzene ring or a heterocycle, the nitrogen-containing monocyclic heterocyclic group optionally condensed with a benzene ring or a heterocycle optionally has substituent(s), $R^{2a}$ is an optionally substituted $C_{6-14}$ aryl group, an optionally substituted thienyl group or an optionally substituted pyridyl group, $R^{3a}$ and $R^{4a}$ are each a hydrogen atom, or one of $R^{3a}$ and $R^{3a}$ is a hydrogen atom, and the other is an optionally substituted lower alkyl group, an acyl group, a halogen atom, a cyano group or a nitro group, and $R^{5a}$ is an alkyl group.

In the formula (A3), as the "nitrogen-containing monocyclic heterocyclic group optionally condensed with a benzene ring or a heterocycle" for $R^{1a}$,
(1) a nitrogen-containing monocyclic heterocyclic group, and
(2) a fused ring group represented by the formula:

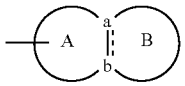

wherein ring A is a nitrogen-containing monocyclic heterocyclic group, ring B is a benzene ring or a heterocycle, a and b are each a bridgehead ring-constituting atom (e.g., a carbon atom, a nitrogen atom and the like), and

----- shows a single bond or a double bond, provided that a bond to an —SO$_2$— group in the formula (A3) is present in a ring A-constituting atom (ring atom) other than the bridgehead ring-constituting atoms a and b, can be mentioned.

As used herein, ring A needs only to contain, as a ring A-constituting atom (ring atom), at least one (preferably 1 to 4, more preferably 1 or 2) nitrogen atom, and one or both of the bridgehead ring-constituting atoms a and b may be nitrogen atoms.

The "nitrogen-containing monocyclic heterocyclic group optionally condensed with a benzene ring or a heterocycle" optionally has substituent(s), and the substituent(s) may be present in any of ring A and ring B.

As the "nitrogen-containing monocyclic heterocyclic group" of the "nitrogen-containing monocyclic heterocyclic group optionally condensed with a benzene ring or a heterocycle" and the above-mentioned ring A, for example, an aromatic nitrogen-containing monocyclic heterocyclic group, a saturated or unsaturated non-aromatic nitrogen-containing monocyclic heterocyclic group (aliphatic nitrogen-containing monocyclic heterocyclic group) and the like containing, as a ring-constituting atom (ring atom), at least one (preferably 1 to 4, more preferably 1 or 2) nitrogen atom can be mentioned.

As the "aromatic nitrogen-containing monocyclic heterocyclic group", for example, aromatic nitrogen-containing monocyclic heterocyclic groups such as pyrrolyl, oxazolyl, isoxazolyl, thiazolyl, isothiazolyl, imidazolyl (1H-imidazol-1-yl, 1H-imidazol-4-yl etc.), pyrazolyl, 1,2,3-oxadiazolyl, 1,2,4-oxadiazolyl, 1,3,4-oxadiazolyl, furazanyl, thiadiazolyl, 1,2,4-thiadiazolyl, 1,3,4-thiadiazolyl, 1,2,3-triazolyl, 1,2,4-triazolyl (1,2,4-triazol-1-yl, 1,2,4-triazol-4-yl etc.), tetrazolyl, pyridyl (2-, 3- or 4-pyridyl etc.), pyridazinyl, pyrimidinyl, pyrazinyl, triazinyl and the like, and N-oxide forms thereof and the like can be mentioned. Of these, a 5- or 6-membered aromatic nitrogen-containing monocyclic heterocyclic group is preferable, and thiazolyl, imidazolyl, pyrazolyl, pyridyl, pyrimidinyl and pyridazinyl are preferable, and pyridyl is particularly preferable.

As the "saturated or unsaturated non-aromatic nitrogen-containing monocyclic heterocyclic group", partially reduced forms (e.g., imidazolinyl, tetrahydropyrimidinyl and the like) of the above-mentioned "aromatic nitrogen-containing monocyclic heterocyclic group" and, for example, azetidinyl, pyrrolidinyl, piperidyl (2-, 3- or 4-piperidyl), morpholinyl, thiomorpholinyl, piperazinyl (1-piperazinyl etc.), homopiperazinyl and the like can be mentioned. Of these, a 5- or 6-membered non-aromatic nitrogen-containing monocyclic heterocyclic group is preferable.

As the "heterocycle" optionally condensed with a nitrogen-containing monocyclic heterocyclic group, for example, an aromatic heterocycle or non-aromatic heterocycle can be mentioned.

As the "aromatic heterocycle", for example, 5- or 6-membered aromatic heteromonocyclic rings such as a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, tetrazole ring, pyridine ring, pyridazine ring, pyrimidine ring, pyrazine ring, triazine ring and the like and, for example, 8- to 12-membered aromatic fused heterocycles such as a benzofuran ring, an isobenzofuran ring, a benzo[b]thiophene ring, an indole ring, an isoindole ring, a 1H-indazole ring, a benzindazole ring, a benzoxazole ring, a 1,2-benzoisoxazole ring, a benzothiazole ring, a benzopyran ring, a 1,2-benzoisothiazole ring, a 1H-benzotriazole ring, a quinoline ring, an isoquinoline ring, a cinnoline ring, a quinazoline ring, a quinoxaline ring, a phthalazine ring, a naphthyridine ring, a purine ring, a pteridine ring, a carbazole ring, an α-carboline ring, a β-carboline ring, a γ-carboline ring, an acridine ring, a phenoxathiine ring, a phenothiazine ring, a phenazine ring, a phenoxathiine ring, a thianthrene ring, a phenanthridine ring, a phenanthrone ring, an indolizine ring, a pyrrolo[1,2-b]pyridazine ring, a pyrazolo[1,5-a]pyridine ring, an imidazo[1,2-a]pyridine ring, an imidazo[1,5-a]pyridine ring, an imidazo[1,2-b]pyridazine ring, an imidazo[1,2-a]pyrimidine ring, a 1,2,4-triazolo[4,3-a]pyridine ring, a 1,2,4-triazolo[4,3-b]pyridazine ring and the like (preferably, a heterocycle wherein the aforementioned 5- or 6-membered aromatic heteromonocyclic ring is condensed with a benzene ring or a heterocycle wherein the same or different two heterocycles of the aforementioned 5- or 6-membered aromatic heteromonocyclic ring are condensed, more preferably a heterocycle wherein the aforementioned 5- or 6-membered aromatic monocyclic heterocyclic group is condensed with a benzene ring, preferably imidazopyrimidinyl etc.) and the like can be mentioned.

As the "non-aromatic heterocycle", for example, 3- to 8-membered saturated or unsaturated non-aromatic heterocycles such as an oxirane ring, an azetidine ring, an oxetane ring, a thietane ring, a pyrrolidine ring, a tetrahydrofuran ring, a thioran ring, a piperidine ring, a tetrahydropyran ring, a morpholine ring, a thiomorpholine ring, a piperazine ring, a 3-hexahydrocyclopenta[c]pyrrole ring, a homopiperidine ring, a homopiperazine ring and the like, or non-aromatic heterocycles wherein the double bonds of the aforementioned aromatic heteromonocyclic ring or aromatic fused heterocycle are partly or entirely saturated such as a dihydropyridine ring, a dihydropyrimidine ring, a 1,2,3,4-tetrahydroquinoline ring, a 1,2,3,4-tetrahydroisoquinoline ring and the like, and the like can be mentioned.

As preferable nitrogen-containing monocyclic heterocyclic group condensed with a benzene ring or a heterocycle, for example, nitrogen-containing aromatic fused heterocyclic groups such as 8- to 16-membered (preferably 8- to 12-membered) nitrogen-containing aromatic bicyclic fused heterocyclic groups such as 2- or 3-indolyl, 1- or 3-isoindolyl, 1H-indazol-3-yl, 2-benzimidazolyl, 2-benzoxazolyl, 3-benzoisoxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, purinyl, pteridinyl, 1,7-phenanthrolin-2-, 3- or 4-yl, 1-, 2- or 3-indolizinyl, pyrrolo[1,2-b]pyridazinyl, pyrazolo[1,5-a]pyridyl, imidazo[1,2-a]pyridyl, imidazo[1,2-b]pyrazolyl, imidazo[1,5-a]pyridyl, imidazo[4,5-c]pyridyl, pyrazolo[1,5-a]pyrimidinyl, pyrazolo[1,5-c]pyrimidinyl, pyrazolo[3,4-d]pyrimidinyl, imidazo[1,2-b]pyridazinyl, imidazo[1,5-b]pyridazinyl, pyrazolo[3,4-b]pyridyl, imidazo[1,2-a]pyrimidinyl, 1,2,4-triazolo[4,3-a]pyridyl, 1,2,4-triazolo[4,3-b]pyridazinyl, [1,2,4]triazolo[1,2-a]pyridazinyl, [1,2,3]triazolo[1,5-a]pyrimidinyl, [1,2,4]triazolo[1,5-c]pyrimidinyl, [1,2,4]triazolo[1,5-a]pyridyl, [1,2,4]triazolo[4,3-a]pyridyl, pyrazolo[5,1-b]thiazolyl, pyrrolo[2,1-f][1,2,4]triazinyl, pyrrolo[1,2-b]pyridazinyl, pyrrolo[2,3-d]pyrimidinyl, pyrrolo[2,3-b]pyridyl, thieno[3,2-b]pyrimidinyl, thieno[2,3-b]pyridyl, thieno[2,3-c]pyridyl, thieno[3,2-b]pyridyl, thieno[3,2-c]pyridyl, pyrido[2,3-b]pyrazyl, pyrido[3,4-b]pyrazyl, pyrido[2,3-d]pyrimidinyl, pyrido[3,2-d]pyrimidinyl, pyrido[4,3-d]pyrimidinyl and the like, and the like, and the like can be mentioned. As the nitrogen-containing aromatic fused heterocycle, fused pyridine wherein a pyridine ring is condensed with one or two (preferably one) of the aforementioned 5- or 6-membered nitrogen-containing aromatic monocyclic heterocycles or one or two (preferably one) benzene rings (when condensed with a benzene ring, the pyridine ring has a bond), fused pyrimidine wherein a pyrimidine ring is condensed with one or two (preferably one) of the aforementioned 5- or 6-membered nitrogen-containing aromatic monocyclic heterocycles, or one or two (preferably one) benzene rings (when condensed with a benzene ring, the pyrimidine ring has a bond) and the like are preferable.

As the "non-aromatic nitrogen-containing heterocycle", for example, 3- to 8-membered (preferably 5- or 6-membered) nitrogen-containing saturated or unsaturated (preferably saturated) non-aromatic heterocycle (aliphatic nitrogen-containing heterocycle) such as azetidine, pyrrolidine, imidazolidine, thiazolidine, oxazolidine, piperidine, morpholine, thiomorpholine, piperazine and the like, or nitrogen-containing non-aromatic heterocycle wherein the double bonds of the aforementioned nitrogen-containing aromatic monocyclic heterocycle or nitrogen-containing aromatic fused heterocycle are partly or entirely saturated, such as 1,2,3,4-tetrahydroquinoline, 1,2,3,4-tetrahydroisoquinoline and the like can be mentioned.

As the "nitrogen-containing monocyclic heterocyclic group optionally condensed with a benzene ring or a heterocycle", a 5- or 6-membered aromatic nitrogen-containing monocyclic heterocyclic group is preferable from among those mentioned above. Of them, a 6-membered aromatic nitrogen-containing heterocyclic group such as pyridyl (e.g., 2-, 3- or 4-pyridyl etc.), pyrimidinyl (e.g., 2-, 4- or 5-pyrimidinyl etc.), pyridazinyl (e.g., 3- or 4-pyridazinyl etc.) and the like is preferable, and pyridyl is particularly preferable.

As the substituent that the "nitrogen-containing monocyclic heterocyclic group optionally condensed with a benzene ring or a heterocycle" may have, the substituents of the above-mentioned substituent group A and (50) a $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., fluorine, chlorine, bromine, iodine), (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., fluorine, chlorine, bromine, iodine), (52) a $C_{2-6}$ alkynyl group (e.g., propargyl, 2-butynyl, 3-butynyl, 3-pentynyl, 3-hexynyl etc.), (53) a $C_{1-6}$ alkyl group substituted by 1 to 3 hydroxy (e.g., hydroxymethyl, hydroxyethyl etc.) and the like can be mentioned.

The substituent may be present at a substitutable position, and the number of the substituents is 1 to 5, preferably 1 to 3.

As the "$C_{6-14}$ aryl group" of the "optionally substituted $C_{6-14}$ aryl group" for $R^{2a}$, for example, phenyl, 1-naphthyl, 2-naphthyl, 2-biphenylyl, 3-biphenylyl, 4-biphenylyl, 2-anthryl and the like can be mentioned.

As the substituent that the "$C_{6-14}$ aryl group" optionally has, groups similar to the substituents that the "nitrogen-containing monocyclic heterocyclic group optionally condensed with a benzene ring or a heterocycle" for the aforementioned $R^{1a}$ optionally has can be mentioned.

The number of the substituents is 1 to 5, preferably 1 to 3.

As the "thienyl group" of the "optionally substituted thienyl group" for $R^{2a}$, 2- or 3-thienyl can be mentioned.

As the substituent that the "thienyl group" optionally has, groups similar to the substituents that the "nitrogen-containing monocyclic heterocyclic group optionally condensed with a benzene ring or a heterocycle" for the aforementioned $R^{1a}$ optionally has can be mentioned.

The number of the substituents is 1 to 4, preferably 1 to 3.

As the "pyridyl group" of the "optionally substituted pyridyl group" for $R^{2a}$, 2-, 3- or 4-pyridyl, or bipyridyl (e.g., 2,3'-bipyridin-5-yl) can be mentioned.

As the substituent that the "pyridyl group" optionally has, groups similar to the substituents that the "nitrogen-containing monocyclic heterocyclic group optionally condensed with a benzene ring or a heterocycle" for the aforementioned $R^{1a}$ optionally has can be mentioned.

The number of the substituents is 1 to 4, preferably 1 to 3.

As the "lower alkyl group" of the "optionally substituted lower alkyl group" for $R^{3a}$ or $R^{4a}$, for example, $C_{1-4}$ alkyl groups such as methyl, ethyl, propyl, isopropyl, butyl, isobutyl, sec-butyl, tert-butyl and the like, and the like can be mentioned.

As the substituent that the "lower alkyl group" optionally has, the substituents of the above-mentioned substituent group A and the like can be mentioned.

The number of the substituents is 1 to 3.

Examples of the "acyl group" for $R^{3a}$ or $R^{4a}$ include acyl groups similar to those exemplified as the "acyl group" for $R^2$, $R^3$ or $R^4$ of the above-mentioned formula (A2).

As the "halogen atom" for $R^{3a}$ or $R^{4a}$, a fluorine atom, a chlorine atom, a bromine atom and an iodine atom can be mentioned.

As the "alkyl group" for $R^{5a}$, for example, $C_{1-6}$ alkyl (e.g., methyl, ethyl, propyl, isopropyl, butyl, isobutyl, sec-butyl, tert-butyl, pentyl, hexyl etc.) and the like can be mentioned.

As $R^{1a}$, a "nitrogen-containing monocyclic heterocyclic group optionally condensed with a benzene ring or a heterocycle" (e.g., 5 or 6-membered aromatic nitrogen-containing monocyclic heterocyclic groups such as thiazolyl, imidazolyl, pyrazolyl, pyridyl, pyrimidinyl, pyridazinyl, pyrazinyl and the like, and the like) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) oxo and (viii) $C_{1-6}$ alkoxy-carbonyl (e.g., methoxycarbonyl, ethoxycarbonyl, propoxycarbonyl, tert-butoxycarbonyl etc.) is preferable.

As $R^{1a}$, especially, a "nitrogen-containing monocyclic heterocyclic group optionally condensed with a benzene ring or a heterocycle" (e.g., a 5 or 6-membered aromatic nitrogen-containing monocyclic heterocyclic group such as thiazolyl, imidazolyl, pyrazolyl, pyridyl, pyrimidinyl, pyridazinyl, pyrazinyl and the like, and the like), which is optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) oxo, is preferable.

As $R^{1a}$, particularly, a 6-membered nitrogen-containing aromatic heterocyclic group (e.g., pyridyl groups (e.g., 2-, 3- or 4-pyridyl etc.), pyrimidinyl groups (e.g., 2-, 4- or 5-pyrimidinyl etc.), pyridazinyl groups (e.g., 3- or 4-pyridazinyl etc.) etc.) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hex-yl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (vi) an amino group optionally substituted by $C_{1-6}$ alkyl (e.g., methyl, ethyl, propyl, isopropyl, butyl, isobutyl, sec-butyl, tert-butyl, pentyl, hexyl etc.) is preferable, and a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) is particularly preferable.

As $R^{2a}$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acetyl, (vi) cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogen atoms (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acyl (e.g., acetyl), (vi) nitro and (vii) amino is preferable.

Of these, as $R^{2a}$, [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl,

[2] a thienyl group optionally substituted by 1 to 3% substituents selected from (i) a halogen atom (e.g., fluorine, chlorine, bromine, iodine); (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acyl (e.g., acetyl), (vi) nitro and (vii) amino is preferable.

Particularly, as $R^{2a}$, [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine) is preferable.

Of those mentioned above, a preferable embodiment of $R^{2a}$ include [1] a phenyl group optionally substituted by 1 to 5 substituents selected from (i) a halogen atom and (ii) $C_{1-6}$ alkyl optionally substituted by 1 to 5 halogen atoms, [2] a pyridyl group optionally substituted by 1 to 4 substituents selected from lower ($C_{1-6}$) alkyl, a halogen atom, alkoxy ($C_{1-6}$ alkoxy), cyano, acyl (e.g., acetyl), nitro and amino, and the like.

As $R^{2a}$, a phenyl group, a 2-fluorophenyl group, a 2-methylphenyl group, a 2-fluoropyridin-3-yl group, a 3-fluoropyridin-4-yl group, a 2-chloropyridin-3-yl group, a 6-chloropyridin-3-yl group, a 4-methylpyridin-3-yl group, a 2-methylpyridin-3-yl group, a 3-methylpyridin-2-yl group, a 2-trifluoromethylpyridin-3-yl group and a 6'-chloro-2,3'-bipyridin-5-yl group are particularly preferable.

Preferably $R^{3a}$ and $R^{4a}$ are each a hydrogen atom, or one of $R^{3a}$ and $R^{4a}$ is a hydrogen atom and the other is a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., fluorine, chlorine, bromine, iodine), a cyano group or a nitro group. A compound wherein both $R^3$ and $R^4$ are hydrogen atoms is particularly preferable.

As the "alkyl" for $R^{5a}$, methyl or ethyl is preferable, and methyl is particularly preferable.

The above-mentioned preferable embodiments of the substituents for $R^{1a}$ to $R^{5a}$ may be optionally combined to achieve a preferable embodiment of compound (A3).

Of compounds (A3), a compound wherein $R^{1a}$ is a 5- or 6-membered aromatic nitrogen-containing monocyclic heterocyclic group (e.g., thiazolyl,' imidazolyl, pyrazolyl, pyridyl, pyrimidinyl, pyridazinyl, pyrazinyl and the like) or an imidazo[1,2-a]pyrimidinyl group, which are optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.) and (vii) $C_{1-6}$ alkoxy-carbonyl (e.g., methoxycarbonyl, ethoxycarbonyl, propoxycarbonyl, tert-butoxycarbonyl etc.);

$R^{2a}$ is [1] a $C_{6-14}$ aryl group (e.g., phenyl group) optionally substituted by 1 to 5 (preferably 1 to 3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tertbutyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) a $C_{1-6}$ alkyl group substituted by 1 to 3 hydroxy (e.g., hydroxymethyl, hydroxyethyl etc.), (ix) $C_{1-6}$ alkylthio (e.g., methylthio, ethylthio, propylthio, isopropylthio, butylthio, isobutylthio, sec-butylthio, pentylthio, hexylthio etc.) optionally substituted by 1 to 5 (preferably 1 to 3) halogen atoms (e.g., fluorine, chlorine, bromine, iodine) and (x) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine) and (v) acetyl,

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), (v) acyl (e.g., acetyl), (vi) nitro and (vii) amino, or

[4] a bipyridyl group optionally substituted by 1 to 3 halogen atoms (e.g., fluorine, chlorine, bromine, iodine); $R^{3a}$ and $R^{4a}$ are each a hydrogen atom, or one of $R^{3a}$ and $R^{4a}$ is a hydrogen atom and the other is a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a halogen atom (e.g., fluorine, chlorine, bromine, iodine), a cyano group or a nitro group;

$R^{5a}$ is methyl or ethyl is preferable, a compound wherein, for example, $R^{1a}$ is a pyridyl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3)

halogen (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogen (e.g., fluorine, chlorine, bromine, iodine), $R^{2a}$ is [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$)alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogen (e.g., fluorine, chlorine, bromine, iodine), $R^{3a}$ and $R^{4a}$ are each a hydrogen atom, and $R^{5a}$ is methyl is particularly preferable.

When the compound represented by the above-mentioned formula (A3) has isomers such as optical isomer, stereoisomer, positional isomer, rotational isomer and the like, any isomers and mixtures are encompassed in the compound (A3). For example, when compound (A3) has an optical isomer, an optical isomer separated from a racemate is also encompassed in the compound (A3). These isomers can be obtained as independent products by a synthesis means or a separation means (e.g., concentration, solvent extraction, column chromatography, recrystallization and the like), and the like known per se.

The compound (A3) may be a crystal, and both a single crystal and crystal mixtures are encompassed in the compound (A3). Crystals can be produced by crystallization according to crystallization methods known per se.

The compound (A3) may be a solvate (e.g., hydrate etc.) or a non-solvate, both of which are encompassed in the compound (A3).

A compound labeled with an isotope (e.g., $^3H$, $^{14}C$, $^{35}S$, $^{125}I$ and the like) is also encompassed in the compound (A3).

The compound represented by the above-mentioned formula (A3) can be produced, for example, according to the method described in WO 2007/026916.

In addition, preferable examples of the nonpeptidic pharmaceutically active ingredient having a primary or secondary amino group also include the compound and a salt thereof disclosed in WO 2008/108380, which is represented by the following formula (A4).

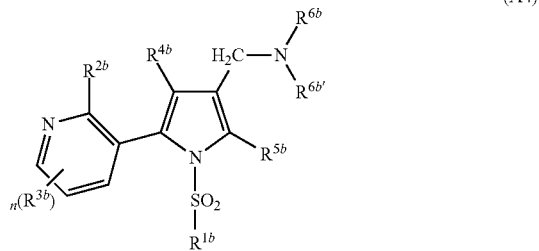

(A4)

wherein $R^{1b}$ is an optionally substituted cyclic group, $R^{2b}$ is a substituent, $R^{3b}$ is an optionally substituted alkyl group, an acyl group, an optionally substituted hydroxy group, an optionally substituted amino group, a halogen atom, a cyano group or a nitro group, $R^{4b}$ and $R^{5b}$ are each a hydrogen atom, an optionally substituted alkyl group, an acyl group, an optionally substituted hydroxy group, an optionally substituted amino group, a halogen atom, a cyano group or a nitro group, $R^{6b}$ and $R^{6b'}$ are each a hydrogen atom or an alkyl group, and n is an integer of 0-3.

Examples of the "optionally substituted cyclic group" for $R^{1b}$ in the formula (A4) include an aryl group, an alicyclic hydrocarbon group and a heterocyclic group, each of which is optionally substituted.

Examples of the aryl group in the "optionally substituted aryl group" for $R^{1b}$ include a $C_{6-14}$ aryl group such as phenyl, 1-naphthyl, 2-naphthyl, 2-biphenylyl, 3-biphenylyl, 4-biphenylyl, 2-anthryl and the like.

Examples of the substituent of the aryl group include (1) a halogen atom (e.g., fluorine atom, chlorine atom, bromine atom, iodine atom etc.), (2) nitro, (3) cyano, (4) hydroxy, (5) $C_{1-6}$ alkoxy optionally having 1 to 5 (preferably 1 to 3) halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 5 (preferably 1 to 3) halogen atoms (e.g., fluorine, chlorine, bromine, iodine) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl optionally substituted by hydroxyl (e.g., methylcarbamoyl, ethylcarbamoyl, 2-hydroxyethylcarbamoyl etc., preferably mono-$C_{1-6}$ alkyl-carbamoyl), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-19}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 1,2,3-oxadiazolyl, 1,2,4-oxadiazolyl, 1,2,5-oxadiazolyl, 1,3,4-oxadiazolyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), which is optionally substituted by 1 to 3 $C_{1-6}$ alkyl groups (e.g., methyl, ethyl, n-propyl, isopropyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) a $C_{1-6}$ alkyl group optionally having 1 to 5 (preferably 1 to 3) halogen atoms (e.g., fluorine, chlorine, bromine, iodine) or hydroxy (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl, hydroxymethyl etc., preferably a $C_{1-6}$ alkyl group optionally having 1 to 5 (preferably 1 to 3) halogen atoms), (51) a $C_{2-6}$ alkenyl group (e.g., allyl, isopropenyl, isobutenyl, 1-methylallyl, 2-pentenyl, 2-hexenyl etc.) optionally having 1 to 5 (preferably 1 to 3) halogen atoms (e.g., fluorine, chlorine, bromine, iodine), (52) a $C_{2-6}$ alkynyl group (e.g., propargyl, 2-butynyl, 3-butynyl, 3-pentynyl, 3-hexynyl etc.), (53) a $C_{6-14}$ aryl group (e.g., phenyl etc.) optionally having 1 to 5 (preferably 1 to 3) halogen atoms (e.g., fluorine, chlorine, bromine, iodine), (54) $C_{7-16}$ aralkyl (e.g., benzyl, phenethyl etc.) optionally having 1 to 5 (preferably 1 to 3) halogen atoms (e.g., fluorine, chlorine, bromine, iodine), (55) oxo (hereinafter to be referred to as substituent group C), and the like.

The substituent may be present at a substitutable position, and the number of the substituents is 1 to 5, preferably 1 to 3.

Examples of the alicyclic hydrocarbon group in the "optionally substituted alicyclic hydrocarbon group" for $R^{1b}$ include a $C_{3-14}$ cycloalkyl group such as cyclopropyl, cyclobutyl, cyclopentyl, cyclohexyl, perhydronaphthyl, perhydroanthranyl, bicyclo[2,2,1]heptyl and the like (preferably a $C_{3-7}$ cycloalkyl group), a $C_{3-14}$ cycloalkenyl group such as cyclopropenyl, cyclobuten-1- or 3-yl, cyclopenten-1-, 3- or 4-yl, cyclohexen-1- or 3-yl and the like (preferably a $C_{3-7}$ cycloalkenyl group) and the like.

Examples of the substituent of the alicyclic hydrocarbon group include those similar to the substituents selected from the above-mentioned substituent group C. The substituent may be present at a substitutable position, and the number of the substituents is 1 to 5, preferably 1 to 3.

Examples of the heterocyclic group in the "optionally substituted heterocyclic group" for $R^{1b}$ include a 4- to 7-membered non-aromatic heterocyclic group (preferably, a 4- to 6-membered non-aromatic heterocyclic group) containing 1 to 3 hetero atom selected from nitrogen atom, oxygen atom, sulfur atom and the like, such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, homomorpholinyl, homopiperazinyl and the like, and a heteroaryl group (preferably, a 5- or 6-membered aromatic heterocyclic group or a fused ring group thereof) such as pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-4-yl, 1,2,3-triazol-1-yl, 1,2,3-triazol-5-yl, 1,2,4-triazol-1-yl, 1,2,4-triazol-3-yl, 1,2,4-triazol-4-yl, 1,2,4-triazol-5-yl), tetrazolyl (e.g., tetrazol-1-, 2- or 5-yl), furyl (e.g., 2- or 3-furyl), thienyl (e.g., 2- or 3-thienyl), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyridyl (e.g., 1-, 2-, 3- or 4-pyridyl), pyridazinyl (e.g., 1-, 3- or 4-pyridazinyl), pyrimidinyl (e.g., 1-, 2-, 4- or 5-pyrimidinyl), pyrazinyl (e.g., 1- or 2-pyrazinyl), benzofuryl (e.g., 2- or 3-benzofuryl), benzothienyl (e.g., 2- or 3-benzothienyl), isoindolyl (e.g., 1- or 3-isoindolyl), benzimidazolyl (e.g., 2-benzimidazolyl), benzoxazolyl (e.g., 2-benzoxazolyl), benzisoxazolyl (e.g., 3-benzisoxazolyl), benzothiazolyl (e.g., 2-benzothiazolyl), benzisothiazolyl (e.g., 3-benzisothiazolyl), cinnolinyl (e.g., 3- or 4-cinnolinyl), quinazolinyl (e.g., 2- or 4-quinazolinyl), quinoxalinyl (e.g., 2- or 3-quinoxalinyl), phthalazinyl (e.g., 1- or 4-phthalazinyl), pteridinyl, indolyl (e.g., 3H-indol-2-, 3-, 4-, 5-, 6- or 7-yl), quinolyl (e.g., 3-, 4-, 5-, 6-, 7- or 8-quinolyl), isoquinolyl (e.g., 1-, 3- or 4-isoquinolyl), pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), imidazo[1,2-a]pyridyl, imidazo[2,1-b]thiazolyl, imidazo[1,2-a]pyrimidinyl, imidazo[1,2-b]pyridazinyl, imidazo[1,2-a]imidazolyl, imidazo[2,1-b](1.3.4)thiadiazolyl, pyrazolo[1,5-a]pyrimidinyl, pyrazolo[5,1-b]thiazolyl or pyrazolo[1,5-a]pyridyl and the like.

Examples of the substituent of the heterocyclic group include those similar to the substituents selected from the above-mentioned substituent group C. The substituent may be present at a substitutable position, and the number of the substituents is 1 to 5, preferably 1 to 3.

$R^{1b}$ is preferably an "optionally substituted aryl group or a heteroaryl group".

Examples of the "substituent" for $R^{2b}$ include an electron withdrawing group and an electron donating group, particularly preferably an electron withdrawing group.

Examples of the electron withdrawing group include a halogen atom (e.g., fluorine, chlorine, bromine, iodine), a cyano group, an acyl group, a halogenoalkyl group (e.g., a halogeno($C_{1-3}$)alkyl group such as fluoromethyl, chloromethyl, bromomethyl, iodomethyl, difluoromethyl, trifluoromethyl and the like etc.) and the like.

Examples of the aforementioned "acyl group" include an acyl group derived from an optionally substituted carboxylic acid, an optionally substituted oxycarboxylic acid, an optionally substituted sulfonic acid, an optionally substituted sulfinic acid and the like, and the like, for example, a group represented by the formula —S(O)$_p$—R$^{7b}$ wherein p is 1 or 2, and R$^{7b}$ is a hydroxyl group, a hydrocarbon group optionally having substituent(s) or a heterocyclic group optionally having substituent(s), a group represented by the formula —COOR$^{8b}$ wherein R$^{8b}$ is a hydrogen atom, a hydrocarbon group optionally having substituent(s) or a heterocyclic group optionally having substituent(s), a group represented by the formula —CONR$^{9b}$R$^{10b}$ wherein R$^{9b}$ and R$^{10b}$ are the same or different and each is a hydrogen atom, a hydrocarbon group optionally having substituent(s) or a heterocyclic group optionally having substituent(s), a group represented by the formula —SO$_2$NH—R$^{11b}$ wherein R$^{12b}$ is a hydrogen atom, a hydrocarbon group optionally having substituent(s) or a heterocyclic group optionally having substituent(s), a group represented by the formula —CO—R$^{12b}$ wherein R$^{12b}$ is a hydrogen atom, a hydrocarbon group optionally having substituent(s) or a heterocyclic group optionally having substituent(s), and the like.

Examples of the "hydrocarbon group" of the "hydrocarbon group optionally having substituent(s)" for R$^{7b}$, R$^{8b}$, R$^{9b}$, R$^{10b}$, R$^{11b}$ or R$^{12b}$ include a chain or cyclic hydrocarbon group (e.g., alkyl, alkenyl, alkynyl, cycloalkyl, aryl, aralkyl etc.). Of these, a chain or cyclic hydrocarbon group having 1 to 16 carbon atoms and the like are preferable.

Examples of the "alkyl" include C$_{1-6}$ alkyl (e.g., methyl, ethyl, propyl, isopropyl, butyl, isobutyl, sec-butyl, tert-butyl, pentyl, hexyl etc.) and the like.

Examples of the "alkenyl" include C$_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the "alkynyl" include C$_{2-6}$ alkynyl (e.g., ethynyl, propargyl, 1-butynyl, 2-butynyl, 3-butynyl, 1-hexynyl etc.) and the like.

Examples of the "cycloalkyl" include C$_{3-7}$ cycloalkyl (e.g., cyclopropyl, cyclobutyl, cyclopentyl, cyclohexyl, cycloheptyl etc.) and the like.

Examples of the "aryl" include C$_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the "aralkyl" include C$_{7-16}$ aralkyl (e.g., phenyl-C$_{1-6}$ alkyl, naphthyl-C$_{1-6}$ alkyl or diphenyl-C$_{1-4}$ alkyl etc. such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like) and the like.

When the above-mentioned "hydrocarbon group" of the "hydrocarbon group optionally having substituent(s)" for R$^{7b}$, R$^{8b}$, R$^{9b}$, R$^{10b}$, R$^{11b}$ or R$^{12b}$ is alkyl, alkenyl or alkynyl, the group may be substituted by 1 to 3 substituents selected from (1) a halogen atom (e.g., fluorine atom, chlorine atom, bromine atom, iodine atom etc.), (2) nitro, (3) cyano, (4) hydroxy, (5) C$_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.), (6) C$_{6-14}$ aryloxy (e.g., phenyloxy, naphthyloxy etc.), (7) C$_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) C$_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) C$_{6-14}$ arylthio (e.g., phenylthio, naphthylthio etc.), (11) C$_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.) (12) amino, (13) mono-C$_{1-6}$ alkylamino (e.g., methylamino, ethylamino etc.), (14) mono-C$_{6-14}$ arylamino (e.g., phenylamino, 1-naphthylamino, 2-naphthylamino etc.), (15) mono-C$_{7-16}$ aralkylamino (e.g., benzylamino etc.), (16) di-C$_{1-6}$ alkylamino (e.g., dimethylamino, diethylamino etc.), (17) di-C$_{6-14}$ arylamino (e.g., diphenylamino etc.), (18) di-C$_{7-16}$ aralkylamino (e.g., dibenzylamino etc.), (19) formyl, (20) C$_{1-6}$ alkyl-carbonyl (e.g., acetyl, propionyl etc.), (21) C$_{6-14}$ aryl-carbonyl (e.g., benzoyl, 1-naphthoyl, 2-naphthoyl etc.), (22) carboxyl, (23) C$_{1-6}$ alkoxy-carbonyl (e.g., methoxycarbonyl, ethoxycarbonyl, propoxycarbonyl, tert-butoxycarbonyl etc.), (24) C$_{6-14}$ aryloxy-carbonyl (e.g., phenoxycarbonyl etc.), (25) carbamoyl, (26) thiocarbamoyl, (27) mono-C$_{1-6}$ alkyl-carbamoyl (e.g., methylcarbamoyl, ethylcarbamoyl etc.), (28) di-C$_{1-6}$ alkyl-carbamoyl (e.g., dimethylcarbamoyl, diethylcarbamoyl, ethylmethylcarbamoyl etc.), (29) C$_{6-14}$ aryl-carbamoyl (e.g., phenylcarbamoyl, 1-naphthylcarbamoyl, 2-naphthylcarbamoyl etc.), (30) C$_{1-6}$ alkylsulfonyl (e.g., methylsulfonyl, ethylsulfonyl etc.), (31) C$_{6-14}$ arylsulfonyl (e.g., phenylsulfonyl, 1-naphthylsulfonyl, 2-naphthylsulfonyl etc.), (32) C$_{1-6}$ alkylsulfinyl (e.g., methylsulfinyl, ethylsulfinyl etc.), (33) C$_{6-14}$ arylsulfinyl (e.g., phenylsulfinyl, 1-naphthylsulfinyl, 2-naphthylsulfinyl etc.), (34) formylamino, (35) C$_{1-6}$ alkyl-carbonylamino (e.g., acetylamino etc.), (36) C$_{6-14}$ aryl-carbonylamino (e.g., benzoylamino, naphthoylamino etc.), (37) C$_{1-6}$ alkoxy-carbonylamino (e.g., methoxycarbonylamino, ethoxycarbonylamino, propoxycarbonylamino, butoxycarbonylamino etc.), (38) C$_{1-6}$ alkylsulfonylamino (e.g., methylsulfonylamino, ethylsulfonylamino etc.), (39) C$_{6-14}$ arylsulfonylamino (e.g., phenylsulfonylamino, 2-naphthylsulfonylamino, 1-naphthylsulfonylamino etc.), (40) C$_{1-6}$ alkyl-carbonyloxy (e.g., acetoxy, propionyloxy etc.), (41) C$_{6-14}$ aryl-carbonyloxy (e.g., benzoyloxy, naphthylcarbonyloxy etc.), (42) C$_{1-6}$ alkoxy-carbonyloxy (e.g., methoxycarbonyloxy, ethoxycarbonyloxy, propoxycarbonyloxy, butoxycarbonyloxy etc.), (43) mono-C$_{1-6}$ alkyl-carbamoyloxy (e.g., methylcarbamoyloxy, ethylcarbamoyloxy etc.), (44) di-C$_{1-6}$ alkyl-carbamoyloxy (e.g., dimethylcarbamoyloxy, diethylcarbamoyloxy etc.), (45) C$_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) C$_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.) and the like.

In addition, when the "hydrocarbon group" of the "hydrocarbon group optionally having substituent(s)" for $R^{7b}$, $R^{8b}$, $R^{9b}$, $R^{10b}$, $R^{11b}$ or $R^{12b}$ is cycloalkyl, aryl or aralkyl, the group may be substituted by 1 to 5 (preferably 1 to 3) substituents selected from (1) halogen atom (e.g., fluorine atom, chlorine atom, bromine atom, iodine atom etc.), (2) nitro, (3) cyano, (4) hydroxy, (5) $C_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl optionally having 1 to 3 halogen atoms (e.g., fluorine atom, chlorine atom, bromine atom, iodine atom) (e.g., methylsulfonyl, ethylsulfonyl, trifluoromethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ arylcarbonylamino (e.g., benzoylamino, naphthoylamino etc.) (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) a $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., fluorine atom, chlorine atom, bromine atom, iodine atom) or hydroxy group, (51) a $C_{2-6}$ alkenyl group (e.g., allyl, isopropenyl, isobutenyl, 1-methylallyl, 2-pentenyl, 2-hexenyl etc.) optionally having 1 to 3 halogen atoms (e.g., fluorine atom, chlorine atom, bromine atom, iodine atom), (52) $C_{2-6}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), and (54) a 5- or 10-membered heterocyclyl-carbonyl containing, besides carbon atom, 1 or 2 kinds of 1 to 4 hetero atoms selected from a nitrogen atom, a sulfur atom and an oxygen atom (e.g., 4-morpholinocarbonyl etc.) (hereinafter to be referred to as substituent group D) and the like.

Examples of the "heterocyclic group" of the "heterocyclic group optionally having substituent (s)" for $R^{7b}$, $R^{8b}$, $R^{9b}$, $R^{10b}$, $R^{11b}$ or $R^{12b}$ include a 3- to 8-membered heterocyclic group (preferably a 5- or 6-membered heterocyclic group) containing 1 to 4 hetero atoms selected from a nitrogen atom (optionally oxidized), an oxygen atom, a sulfur atom (optionally mono- or di-oxidized) and the like, or a group wherein a 3- to 8-membered heterocyclic group (preferably a 5- or 6-membered heterocyclic group) containing 1 to 4 hetero atoms selected from a nitrogen atom (optionally oxidized), an oxygen atom, a sulfur atom (optionally mono- or di-oxidized) and the like is condensed with a benzene ring or a 3- to 8-membered ring group (preferably a 5- or 6-membered ring group) containing 1 to 4 hetero atoms selected from a nitrogen atom (optionally oxidized), an oxygen atom, a sulfur atom (optionally mono- or di-oxidized) and the like, preferably a group wherein the 5- or 6-membered heterocyclic group is condensed with a 5- or 6-membered ring optionally containing 1 to 4 hetero atoms selected from a nitrogen atom (optionally oxidized), an oxygen atom, a sulfur atom (optionally mono- or di-oxidized) and the like.

Specific examples thereof include aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-1-, 4- or -5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein the sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), triazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein the nitrogen atom is oxidized (e.g., 2-, 3- or 4-pyridyl-N-oxide), pyridazinyl (e.g., 3- or 4-pyridazinyl), pyridazinyl wherein one or both of the nitrogen atoms are oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atoms are oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indole-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein the sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl and the like.

Examples of the "substituent" of the heterocyclic group include those similar to the substituents selected from the above-mentioned substituent group D. The number of the substituents is 1 to 5, preferably 1 to 3.

Of the above-mentioned group, the electron withdrawing group is preferably a halogen atom, a cyano group, an acyl group or a trifluoromethyl group.

Examples of the electron donating group include a $C_{1-6}$ alkyl group (e.g., methyl, ethyl, propyl, isopropyl, butyl, isobutyl, sec-butyl, tert-butyl, pentyl, hexyl etc.), a $C_{1-6}$ alkylthio group (e.g., methylthio, ethylthio, propylthio, isopropylthio, butylthio, pentylthio, hexylthio etc.), a $C_{1-6}$ alkoxy group (e.g., methoxy, ethoxy, propoxy, isopropoxy, butoxy, pentyloxy, hexyloxy etc.), a group represented by the —$NR^{13b}R^{14b}$ wherein $R^{13b}$ and $R^{14b}$ are the same or different and each is a hydrogen atom or an alkyl group, and the like. Examples of the alkyl group for $R^{13b}$) or $R^{14b}$ include a $C_{1-6}$ alkyl group such as methyl, ethyl, propyl, isopropyl, butyl, isobutyl, sec-butyl, tert-butyl, pentyl, hexyl and the like, particularly preferably a $C_{1-3}$ alkyl group.

Of the above-mentioned group, the electron donating group is preferably a $C_{1-3}$ alkyl, a $C_{1-3}$ alkylthio, or a group represented by the formula —$NR^{13b}R^{14b}$ wherein each symbol is as defined above.

Of the aforementioned group, the "substituent" for $R^{2b}$ is preferably, for example, an electron withdrawing group or electron donating group having not more than 7 atoms and comparatively low molecular weight shown above.

In the formula (A4), $R^{3b}$ is an optionally substituted alkyl group, an acyl group, an optionally substituted hydroxy group, an optionally substituted amino group, a halogen atom, a cyano group or a nitro group. $R^{3b}$ is preferably an alkyl group optionally substituted by halogen, an acyl group, a halogen atom, a cyano group or a nitro group.

$R^{4b}$ and $R^{5b}$ are the same or different and each is a hydrogen atom, an optionally substituted alkyl group, an acyl group, an optionally substituted hydroxy group, an optionally substituted amino group, a halogen atom, a cyano group or a nitro group. Preferably, $R^{4b}$ and $R^{5b}$ are the same or different and each is a hydrogen atom, an alkyl group optionally substituted by halogen, an acyl group, a halogen atom, a cyano group or a nitro group.

Examples of the "alkyl group" in the "optionally substituted alkyl group" for $R^{3b}$, $R^{4b}$ or $R^{5b}$ include a $C_{1-6}$ alkyl group such as methyl, ethyl, propyl, isopropyl, butyl, isobutyl, sec-butyl, tert-butyl, pentyl, hexyl and the like. Examples of the "substituent" of the alkyl include those similar to the substituents that the above-mentioned "hydrocarbon group" for $R^{7b}$, $R^{8b}$, $R^{9b}$, $R^{10b}$, $R^{11b}$ or $R^{12b}$ may have when it is alkyl, alkenyl or alkynyl. The number of the substituents is 1 to 5, preferably 1 to 3.

Preferable examples of the substituent of the alkyl group for $R^{3b}$, $R^{4b}$ or $R^{5b}$ include halogen (e.g., a fluorine atom, a chlorine atom, a bromine atom, an iodine atom). The number of the halogen atom as a substituent is 1 to 5, preferably 1 to 3.

Examples of the "acyl group" for $R^{3b}$, $R^{4b}$ or $R^{5b}$ include acyl groups having 1 to 20 carbon atoms, which is derived from organic carboxylic acids, for example, $C_{1-7}$ alkanoyl groups (e.g., formyl; $C_{1-6}$ alkyl-carbonyl such as acetyl, propionyl, butyryl, isobutyryl, pentanoyl, hexanoyl, heptanoyl and the like; etc.), $C_{6-14}$ aryl-carbonyl groups (e.g., benzoyl, naphthalenecarbonyl etc.), $C_{1-6}$ alkoxy-carbonyl groups (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), $C_{6-14}$ aryloxy-carbonyl groups (e.g., phenoxycarbonyl group), $C_{7-19}$ aralkyl-carbonyl groups (e.g., phenyl-$C_{1-4}$ alkylcarbonyl such as benzylcarbonyl, phenethylcarbonyl, phenylpropylcarbonyl and the like, naphthyl-$C_{1-4}$ alkylcarbonyl such as benzhydrylcarbonyl, naphthylethylcarbonyl and the like, etc.), $C_{7-19}$ aralkyloxy-carbonyl groups (e.g., phenyl-$C_{1-4}$ alkyloxycarbonyl such as benzyloxycarbonyl and the like, etc.), 5- or 6-membered heterocyclyl-carbonyl groups or condensed heterocyclyl-carbonyl groups thereof (e.g., pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4-, or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein the nitrogen atom is oxidized, such as 2-, 3- or 4-pyridyl-N-oxidocarbonyl and the like; pyridazinylcarbonyl such as 3- or 4-pyridazinylcarbonyl and the like; pyridazinyl wherein one or both of the nitrogen atoms are oxidized, such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both of the nitrogen atoms are oxidized, such as 2-, 4-, 5- or 6-pyrimidinyl-N-oxidocarbonyl and the like; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl (e.g., 1,5-naphthyridin-2- or 3-ylcarbonyl) such as 1,5-, 1,6-, 1,7-, 1,8-, 2,6- or 2,7-naphthyridinylcarbonyl and the like; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); 5- or 6-membered heterocyclyl-carbonyl groups (e.g., 5- or 6-membered heterocyclylcarbonyl group containing 1 to 4 hetero atoms such as a nitrogen atom (optionally oxidized), an oxygen atom, a sulfur atom (optionally mono- or di-oxidized) and the like, such as chromenylcarbonyl (e.g., 2H-chromen-2- or 3-ylcarbonyl etc.) and the like), 5- or 6-membered heterocyclyl-acetyl groups (e.g., 5- or 6-membered heterocyclyl-acetyl groups containing 1 to 4 hetero atoms such as a nitrogen atom (optionally oxidized), an oxygen atom, a sulfur atom (optionally mono- or di-oxidized) and the like such as 2-pyrrolylacetyl, 3-imidazolylacetyl, 5-isoxazolylacetyl and the like), and the like can be used.

As regards the substituent of acyl group, for example, when the above-mentioned acyl group is an alkanoyl group or an alkoxy-carbonyl group, it is optionally substituted by 1 to 3 alkylthio groups (e.g., $C_{1-4}$ alkylthio such as methylthio, ethylthio, n-propylthio, isopropylthio and the like, and the like), halogen (e.g., fluorine, chlorine, bromine, iodine), an alkoxy group (e.g., $C_{1-6}$ alkoxy such as methoxy, ethoxy, n-propoxy, tert-butoxy, n-hexyloxy and the like, and the like), a nitro group, an alkoxy-carbonyl group (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), an alkylamino group (e.g., mono- or alkylamino such as methylamino; ethylamino, n-propylamino, n-butylamino, tert-butylamino, n-pentylamino, n-hexylamino, dimethylamino, diethylamino, methylethylamino, di-(n-propyl) amino, di-(n-butyl)amino and the like, and the like), an alkoxyimino group (e.g., $C_{1-6}$ alkoxyimino such as methoxyimino, ethoxyimino, n-propoxyimino, tert-butoxyimino, n-hexyloxy-imino and the like, and the like) or hydroxy-imino.

When the above-mentioned acyl group is an aryl-carbonyl group, an aryloxy-carbonyl group, an aralkyl-carbonyl group, an aralkyloxycarbonyl group, a 5- or 6-membered heterocyclyl-carbonyl group or a 5- or 6-membered heterocyclyl-acetyl group, it is optionally substituted by 1 to 5 (preferably 1 to 3) alkyl group (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), an alkenyl group (e.g., $C_{2-6}$ alkenyl such as allyl, isopropenyl, isobutenyl, 1-methylallyl, 2-pentenyl, 2-hexenyl and the like, and the like), an alkynyl group (e.g., $C_{2-6}$ alkynyl such as propargyl, 2-butynyl, 3-butynyl, 3-pentynyl, 3-hexynyl and the like, and the like), an alkoxy group (e.g., $C_{1-6}$ alkoxy such as methoxy, ethoxy, n-propoxy, tert-butoxy, n-hexyloxy and the like, and the like), an acyl group [e.g., $C_{1-7}$ alkanoyl such as formyl, acetyl, propionyl, butyryl, isobutyryl, pentanoyl, hexanoyl, heptanoyl and the like; $C_{6-14}$ aryl-carbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, halogen (e.g., fluorine, chlorine, bromine, iodine) or an alkylthio group ($C_{1-4}$ alkylthio such as methylthio, ethylthio, n-propylthio, isobutylthio and the like, and the like).

Examples of the "optionally substituted hydroxy group" for $R^{3b}$, $R^{4b}$ or $R^{5b}$ include a group represented by —$OR^{16b}$ wherein $R^{16b}$ is a hydrogen atom, an optionally substituted hydrocarbon group, an optionally substituted heterocyclic group or an acyl group.

Examples of the "optionally substituted hydrocarbon group" for $R^{16b}$ include those similar to the "optionally substituted hydrocarbon group" for the above-mentioned $R^{7b}$, $R^{8b}$, $R^{9b}$, $R^{10b}$, $R^{11b}$ or $R^{12b}$.

Examples of the "optionally substituted heterocyclic group" for $R^{16b}$ include those similar to the "optionally substituted heterocyclic group" for the above-mentioned $R^{7b}$, $R^{8b}R^{9b}$, $R^{10b}$, $R^{11b}$ or $R^{12b}$.

Examples of the "acyl group" for $R^{16b}$ include those similar to the "acyl group" exemplified as the above-mentioned "substituent" for $R^{2b}$.

Examples of the "optionally substituted amino group" for $R^{3b}$, $R^{4b}$ or $R^{5b}$ include a group represented by —$NR^{17b}R^{18b}$ wherein $R^{17b}$ and $R^{18b}$ are the same or different and each is a hydrogen atom, an optionally substituted hydrocarbon group, an optionally substituted heterocyclic group or an acyl group.

Examples of the "optionally substituted hydrocarbon group" for $R^{17b}$ or $R^{18b}$ include those similar to the "optionally substituted hydrocarbon group" for the above-mentioned $R^{7b}$, $R^{8b}$, $R^{9b}$, $R^{10b}$, $R^{11b}$ or $R^{12b}$.

Examples of the "optionally substituted heterocyclic group" for $R^{17b}$ or $R^{18b}$ include those similar to the "optionally substituted heterocyclic group" for the above-mentioned $R^{7b}$, $R^{9b}$, $R^{7b}$, $R^{11b}$ or $R^{12b}$.

Examples of the "optionally substituted acyl group" for $R^{17b}$ or $R^{18b}$ include those similar to the "acyl group" exemplified as the above-mentioned "substituent" for $R^{2b}$.

Examples of the "halogen atom" for $R^{3b}$, $R^{4b}$ or $R^{5b}$ include fluorine, chlorine, bromine and iodine.

In the formula (A4), $R^{3b}$ is optionally substituted at any substitutable position of the pyridine ring. The number (i.e., n) of substituent $R^{3b}$ is 0 to 3. When n is 2 or 3, each of $R^{3b}$ is the same or different.

Preferably, n is 0.

Preferably, $R^{4b}$ and $R^{5b}$ are the same or different and each is a hydrogen atom or a halogen atom.

Examples of the "alkyl group" for $R^{6b}$ or $R^{6b'}$ include a $C_{1-6}$ alkyl group such as methyl, ethyl, propyl, isopropyl, butyl, isobutyl, sec-butyl, tert-butyl, pentyl, hexyl and the like, preferably a $C_{1-3}$ alkyl group, particularly preferably methyl.

Preferable embodiment of the partial structure of the formula (A4):

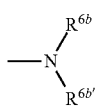

is

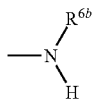

wherein $R^{6b}$ is an alkyl group.

When the compound represented by the above-mentioned formula (A4) has isomers such as optical isomer, stereoisomer, positional isomer, rotational isomer and the like, any isomers and mixtures are encompassed in the compound (A4). For example, when compound (A4) has an optical isomer, an optical isomer separated from a racemate is also encompassed in the compound (A4). These isomers can be obtained as independent products by a synthesis means or a separation means (e.g., concentration, solvent extraction, column chromatography, recrystallization and the like), and the like known per se.

The compound (A4) may be a crystal, and both a single crystal and crystal mixtures are encompassed in the compound (A4). Crystals can be produced by crystallization according to crystallization methods known per se.

The compound (A4) may be a solvate (e.g., hydrate etc.) or a non-solvate, both of which are encompassed in the compound (A4).

A compound labeled with an isotope (e.g., $^3$H, $^{14}$C, $^{35}$S, $^{125}$I and the like) is also encompassed in the compound (A4).

The compound represented by the above-mentioned formula (A4) can be produced, for example, according to the method described in WO 2008/108380.

In the pharmaceutical composition of the present invention, preferable examples of the nonpeptidic pharmaceutically active ingredient having a primary or secondary amino group include the following compounds.

N-methyl-1-{1-[(4-methylphenyl)sulfonyl]-5-phenyl-1H-pyrrol-3-yl}methanamine or a salt thereof,
1-{1-[(4-fluorophenyl)sulfonyl]-5-phenyl-1H-pyrrol-3-yl}-N-methylmethanamine or a salt thereof,
1-[1-(methylsulfonyl)-5-phenyl-1H-pyrrol-3-yl]-N-methylmethanamine or a salt thereof,
1-{1-[(4-methoxyphenyl)sulfonyl]-5-phenyl-1H-pyrrol-3-yl}-N-methylmethanamine or a salt thereof,
1-{1-[(4-fluorophenyl)sulfonyl]-2-methyl-5-phenyl-1H-pyrrol-3-yl}-N-methylmethanamine or a salt thereof,
1-{1-(4-fluorophenyl)-1-[(4-methylphenyl)sulfonyl]-1H-pyrrol-3-yl}-N-methylmethanamine or a salt thereof,
N-methyl-1-{5-(3-methylphenyl)-1-[(4-methylphenyl)sulfonyl]-1H-pyrrol-3-yl}methanamine or a salt thereof,
N-methyl-1-{5-(3-fluorophenyl)-1-[(4-methylphenyl)sulfonyl]-1H-pyrrol-3-yl}methanamine or a salt thereof,
N-methyl-1-{1-[(2-methylphenyl)sulfonyl]-5-phenyl-1H-pyrrol-3-yl}methanamine or a salt thereof,
N-methyl-1-(5-phenyl-1-{[4-(trifluoromethyl)phenyl]sulfonyl}-1H-pyrrol-3-yl)methanamine or a salt thereof,
1-{1-[(4-fluoro-2-methylphenyl)sulfonyl]-5-phenyl-1H-pyrrol-3-yl}-N-methylmethanamine or a salt thereof,
N,N-dimethyl-1-(5-phenyl-1-{[4-(trifluoromethyl)phenyl]sulfonyl}-1H-pyrrol-3-yl)methanamine or a salt thereof,
1-[5-(4-fluorophenyl)-1-(phenylsulfonyl)-1H-pyrrol-3-yl]-N-methylmethanamine or a salt thereof,
N-methyl-1-[5-(2-methylphenyl)-1-(4-methylphenylsulfonyl)-1H-pyrrol-3-yl]methanamine or a salt thereof,
1-{5-(4-fluorophenyl)-1-[(4-fluorophenyl)sulfonyl]-1H-pyrrol-3-yl}-N-methylmethanamine or a salt thereof,
1-(5-(4-fluorophenyl)-1-{[4-(trifluoromethyl)phenyl]sulfonyl}-1H-pyrrol-3-yl)-N-methylmethanamine or a salt thereof,
1-[1-[(4-fluorophenyl)sulfonyl]-5-(4-methoxyphenyl)-1H-pyrrol-3-yl]-N-methylmethanamine or a salt thereof,
1-{1-[(4-fluorophenyl)sulfonyl]-5-[2-(trifluoromethyl)phenyl]-1H-pyrrol-3-yl}-N-methylmethanamine or a salt thereof,
N-methyl-1-{1-(4-methylphenyl)sulfonyl}-5-[2-(trifluoromethyl)phenyl]-1H-pyrrol-3-yl}methanamine or a salt thereof,
N-methyl-1-[2-methyl-5-phenyl-1-(phenylsulfonyl)-1H-pyrrol-3-yl]methanamine or a salt thereof,
1-{5-(2,4-difluorophenyl)-1-[(4-methoxyphenyl)sulfonyl]-1H-pyrrol-3-yl}-N-methylmethanamine or a salt thereof,
1-[1-[(4-methoxyphenyl)sulfonyl]-5-(4-phenoxyphenyl)-1H-pyrrol-3-yl]-N-methylmethanamine or a salt thereof,
1-[1-[(4-methoxyphenyl)sulfonyl]-5-(2-naphthyl)-1H-pyrrol-3-yl]-N-methylmethanamine or a salt thereof,
3-[1-[(4-methoxyphenyl)sulfonyl]-4-[(methylamino)methyl]-1H-pyrrol-2-yl]aniline or a salt thereof,
1-{1-[(4-methoxyphenyl)sulfonyl]-5-pyridin-3-yl-1H-pyrrol-3-yl}-N-methylmethanamine or a salt thereof,
1-{(1-[(4-methylphenyl)sulfonyl]-5-phenyl-1H-pyrrol-3-yl}methanamine or a salt thereof,
N-methyl-1-{4-methyl-1-[(4-methylphenyl)sulfonyl]-5-phenyl-1H-pyrrol-3-yl}methanamine or a salt thereof,
3-{4-[(methylamino)methyl]-1-[(4-methylphenyl)sulfonyl]-1H-pyrrol-2-yl}benzonitrile or a salt thereof,
4-{4-[(methylamino)methyl]-1-[(4-methylphenyl)sulfonyl]-1H-pyrrol-2-yl}benzonitrile or a salt thereof,
N-methyl-1-[1-(phenylsulfonyl)-5-(3-thienyl)-1H-pyrrol-3-yl]methanamine or a salt thereof,
N-methyl-1-[5-phenyl-1-(phenylsulfonyl)-1H-pyrrol-3-yl]methanamine or a salt thereof,
1-{1-[(4-fluorophenyl)sulfonyl]-5-(3-thienyl)-1H-pyrrol-3-yl}-N-methylmethanamine or a salt thereof,
1-{1-[(3-chlorophenyl)sulfonyl]-5-phenyl-1H-pyrrol-3-yl}-N-methylmethanamine or a salt thereof,
1-[1-[(3-chlorophenyl)sulfonyl]-5-(3-thienyl)-1H-pyrrol-3-yl]-N-methylmethanamine or a salt thereof,
1-[1-[(3-chlorophenyl)sulfonyl]-5-(4-fluorophenyl)-1H-pyrrol-3-yl]-N-methylmethanamine or a salt thereof,
1-{1-[(4-chlorophenyl)sulfonyl]-5-phenyl-1H-pyrrol-3-yl}-N-methylmethanamine or a salt thereof,
1-{1-[(3,4-difluorophenyl)sulfonyl]-5-phenyl-1H-pyrrol-3-yl}-N-methylmethanamine or a salt thereof,
1-[1-(2,3-dihydro-1-benzofuran-5-ylsulfonyl)-5-phenyl-1H-pyrrol-3-yl]-N-methylmethanamine or a salt thereof,
1-[1-(butylsulfonyl)-5-phenyl-1H-pyrrol-3-yl]-N-methylmethanamine or a salt thereof,
1-{1-[(4-isopropoxyphenyl)sulfonyl]-5-phenyl-1H-pyrrol-3-yl}-N-methylmethanamine or a salt thereof,
1-{1-[(3-methoxyphenyl)sulfonyl]-5-phenyl-1H-pyrrol-3-yl}-N-methylmethanamine or a salt thereof,
3-({4-[(methylamino)methyl]-2-phenyl-1H-pyrrol-1-yl}sulfonyl)benzonitrile or a salt thereof,
N-methyl-1-[5-phenyl-1-(3-thienylsulfonyl)-1H-pyrrol-3-yl]methanamine or a salt thereof,
1-[5-(3-furyl)-1-[(4-methoxyphenyl)sulfonyl]-1H-pyrrol-3-yl]-N-methylmethanamine or a salt thereof, 1-{1-[(2,5-dichloro-3-thienyl)sulfonyl]-5-phenyl-1H-pyrrol-3-yl}-N-methylmethanamine or a salt thereof,
1-(2-chloro-5-phenyl-1-{[4-(trifluoromethyl)phenyl]sulfonyl}-1H-pyrrol-3-yl)-N-methylmethanamine or a salt thereof,
1-{1-[(3-chlorophenyl)sulfonyl]-2-methyl-5-phenyl-1H-pyrrol-3-yl}-N-methylmethanamine or a salt thereof,
N-methyl-1-(5-phenyl-1-{[4-(trifluoromethoxy)phenyl]sulfonyl}-1H-pyrrol-3-yl)methanamine or a salt thereof,
N-methyl-1-[5-phenyl-1-(2-thienylsulfonyl)-1H-pyrrol-3-yl]methanamine or a salt thereof,
N-methyl-1-[2-methyl-1-(phenylsulfonyl)-5-(3-thienyl)-1H-pyrrol-3-yl]methanamine or a salt thereof,
1-[5-(4-fluorophenyl)-2-methyl-1-(phenylsulfonyl)-1H-pyrrol-3-yl]-N-methylmethanamine or a salt thereof,
N-ethyl-1-[5-(4-fluorophenyl)-2-methyl-1-(phenylsulfonyl)-1H-pyrrol-3-yl]methylamine or a salt thereof,
1-[2,4-dimethyl-5-phenyl-1-(phenylsulfonyl)-1H-pyrrol-3-yl]-N-methylmethanamine or a salt thereof,
N-methyl-1-[5-phenyl-1-(phenylsulfonyl)-4-propyl-1H-pyrrol-3-yl]methanamine or a salt thereof,
1-[4,5-diphenyl-1-(phenylsulfonyl)-1H-pyrrol-3-yl]-N-methylmethanamine or a salt thereof,
1-[2-chloro-5-phenyl-1-(phenylsulfonyl)-1H-pyrrol-3-yl]-N-methylmethanamine or a salt thereof,
1-[2-fluoro-5-phenyl-1-(phenylsulfonyl)-1H-pyrrol-3-yl]-N-methylmethanamine or a salt thereof,
1-[2-chloro-4-fluoro-5-phenyl-1-(phenylsulfonyl)-1H-pyrrol-3-yl]-N-methylmethanamine or a salt thereof,
1-[4-fluoro-5-phenyl-1-(phenylsulfonyl)-1H-pyrrol-3-yl]-N-methylmethanamine or a salt thereof,
N-methyl-1-{2-methyl-1-[(3-methylphenyl)sulfonyl]-5-phenyl-1H-pyrrol-3-yl}methanamine or a salt thereof,
N-methyl-1-[1-(2-methylpyrimidin-5-ylsulfonyl)-5-phenyl-1H-pyrrol-3-yl]methanamine or a salt thereof,
N-methyl-1-{4-methyl-[1-(3-methylphenyl)sulfonyl]-5-phenyl-1H-pyrrol-3-yl}methanamine or a salt thereof,
1-{[1-(4-fluorophenyl)sulfonyl]-4-methyl-5-phenyl-1H-pyrrol-3-yl}-N-methylmethanamine or a salt thereof,
N-methyl-1-[2-methyl-1-(pyridin-3-ylsulfonyl)-5-phenyl-1H-pyrrol-3-yl]methanamine or a salt thereof,
1-[4-chloro-2-methyl-5-phenyl-1-(phenylsulfonyl)-1H-pyrrol-3-yl]-N-methylmethanamine or a salt thereof,
1-[5-butyl-1-(phenylsulfonyl)-1H-pyrrol-3-yl]-N-methylmethanamine or a salt thereof,
1-[5-cyclohexyl-1-(phenylsulfonyl)-1H-pyrrol-3-yl]-N-methylmethanamine or a salt thereof,
1-[5-cyclopropyl-1-(phenylsulfonyl)-1H-pyrrol-3-yl]-N-methylmethanamine or a salt thereof,
N-methyl-1-(1-{[3-(methylsulfonyl)phenyl]sulfonyl}-5-phenyl-1H-pyrrol-3-yl)methanamine or a salt thereof,
1-(1-{[3-(ethylsulfonyl)phenyl]sulfonyl}-5-phenyl-1H-pyrrol-3-yl)-N-methylmethanamine or a salt thereof,
1-[1-(2,3-dihydro-1,4-benzodioxyn-6-ylsulfonyl)-5-phenyl-1H-pyrrol-3-yl]-N-methylmethanamine or a salt thereof,
2-({4-[(methylamino)methyl]-2-phenyl-1H-pyrrol-1-yl}sulfonyl)benzonitrile or a salt thereof,
4-({4-[(methylamino)methyl]-2-phenyl-1H-pyrrol-1-yl}sulfonyl)benzonitrile or a salt thereof,
methyl 2-({4-[(methylamino)methyl]-2-phenyl-1H-pyrrol-1-yl}sulfonyl)benzoate or a salt thereof,
methyl 2-({4-[(methylamino)methyl]-2-phenyl-1H-pyrrol-1-yl}sulfonyl)benzoate or a salt thereof,
methyl 3-({4-[(methylamino)methyl]-2-phenyl-1H-pyrrol-1-yl}sulfonyl)benzoate or a salt thereof,
methyl 3-({4-[(methylamino)methyl]-2-phenyl-1H-pyrrol-1-yl}sulfonyl)benzoate or a salt thereof,
2-chloro-4-({4-[(methylamino)methyl]-2-phenyl-1H-pyrrol-1-yl}sulfonyl)benzonitrile or a salt thereof,
[1-(1,3-benzothiazol-6-ylsulfonyl)-5-phenyl-1H-pyrrol-3-yl]-N-methylmethanamine or a salt thereof,
1-{1-[(1,1-dioxide-2,3-dihydro-1-benzothien-6-yl)sulfonyl]-5-phenyl-1H-pyrrol-3-yl}-N-methylmethanamine or a salt thereof,
1-[1-(1-benzothien-2-ylsulfonyl)-5-phenyl-1H-pyrrol-3-yl]-N-methylmethanamine or a salt thereof,
N-methyl-1-(1-{[4-(methylsulfonyl)phenyl]sulfonyl}-5-phenyl-1H-pyrrol-3-yl)methanamine or a salt thereof,
1-[3-({4-[(methylamino)methyl]-2-phenyl-1H-pyrrol-1-yl}sulfonyl)phenyl]ethanone or a salt thereof,
N-methyl-1-{1-[(3-nitrophenyl)sulfonyl]-5-phenyl-1H-pyrrol-3-yl}methanamine or a salt thereof,
N-methyl-1-[5-phenyl-1-(pyridin-3-ylsulfonyl)-1H-pyrrol-3-yl]methanamine or a salt thereof,
1-{1-[(6-methoxypyridin-3-yl)sulfonyl]-5-phenyl-1H-pyrrol-3-yl}-N-methylmethanamine or a salt thereof,
N-methyl-1-[1-(4-methylaminopyridin-3-ylsulfonyl)-5-phenyl-1H-pyrrol-3-yl]methanamine or a salt thereof,
N-methyl-1-[1-(2-methylaminopyridin-3-ylsulfonyl)-5-phenyl-1H-pyrrol-3-yl]methanamine or a salt thereof,
N-methyl-1-[1-(2-methylaminopyrimidin-5-ylsulfonyl)-5-phenyl-1H-pyrrol-3-yl]methanamine or a salt thereof,
1-[5-(2-fluorophenyl)-1-{[3-(methylsulfonyl)phenyl]sulfonyl}-1H-pyrrol-3-yl]-N-methylmethanamine or a salt thereof,
1-[1-{[3-(ethylsulfonyl)phenyl]sulfonyl}-5-(2-fluorophenyl)-1H-pyrrol-3-yl]-N-methylmethanamine or a salt thereof,
2-{[2-(2-fluorophenyl)-4-[(methylamino)methyl]-1H-pyrrol-1-yl]sulfonyl}benzonitrile or a salt thereof,
4-{[2-(2-fluorophenyl)-4-[(methylamino)methyl]-1H-pyrrol-1-yl]sulfonyl}benzonitrile or a salt thereof,
1-{5-(2-fluorophenyl)-1-[(2-fluorophenyl)sulfonyl]-1H-pyrrol-3-yl}-N-methylmethanamine or a salt thereof,
1-[5-(2-fluorophenyl)-1-(pyridin-3-ylsulfonyl)-1H-pyrrol-3-yl]-N-methylmethanamine or a salt thereof,
N-methyl-1-(1-{[3-(methylsulfonyl)phenyl]sulfonyl}-5-[2-(trifluoromethyl)phenyl]-1H-pyrrol-3-yl)methanamine or a salt thereof,
N-methyl-1-{1-(pyridin-3-ylsulfonyl)-5-[2-(trifluoromethyl)phenyl]-1H-pyrrol-3-yl}methanamine or a salt thereof,
N-methyl-1-[5-(2-methylphenyl)-1-{[3-(methylsulfonyl)phenyl]sulfonyl}-1H-pyrrol-3-yl]methanamine or a salt thereof,
N-methyl-1-[1-(phenylsulfonyl)-5-(pyridin-2-yl)-1H-pyrrol-3-yl]methanamine or a salt thereof,
1-{1-[(3,4-difluorophenyl)sulfonyl]-5-(pyridin-2-yl)-1H-pyrrol-3-yl}-N-methylmethanamine or a salt thereof,
1-[1-(2,3-dihydro-1,4-benzodioxyn-5-ylsulfonyl)-4-methyl-5-phenyl-1H-pyrrol-3-yl]-N-methylmethanamine or a salt thereof,
1-{1-[(2,5-dimethoxyphenyl)sulfonyl]-4-methyl-5-phenyl-1H-pyrrol-3-yl}-N-methylmethanamine or a salt thereof,
1-[1-(2,3-dihydro-1,4-benzodioxyn-6-ylsulfonyl)-4-methyl-5-phenyl-1H-pyrrol-3-yl]-N-methylmethanamine or a salt thereof,
1-(1-{[3-(methylsulfonyl)phenyl]sulfonyl}-4-methyl-5-phenyl-1H-pyrrol-3-yl)-N-methylmethanamine or a salt thereof;
N-methyl-1-{4-methyl-5-phenyl-1-(3-thienylsulfonyl)-1H-pyrrol-3-yl}methanamine or a salt thereof,
N-methyl-1-[4-methyl-1-(pyridin-3-ylsulfonyl)-5-phenyl-1H-pyrrol-3-yl]methanamine or a salt thereof, N-methyl-1-[4-methyl-1-(pyridin-2-ylsulfonyl)-5-phenyl-1H-pyrrol-3-yl]methanamine or a salt thereof,
1-{1-[(1,2-dimethyl-1H-imidazol-4-yl)sulfonyl]-4-methyl-5-phenyl-1H-pyrrol-3-yl}-N-methylmethanamine or a salt thereof,
1-{1-[(5-chloro-1,3-dimethyl-1H-pyrazol-4-yl)sulfonyl]-4-methyl-5-phenyl-1H-pyrrol-3-yl}-N-methylmethanamine or a salt thereof,
1-{1-[(1,3-dimethyl-1H-pyrazol-4-yl)sulfonyl]-4-methyl-5-phenyl-1H-pyrrol-3-yl}-N-methylmethanamine or a salt thereof,
1-{1-[(2,4-dimethyl-1,3-thiazol-5-yl)sulfonyl]-4-methyl-5-phenyl-1H-pyrrol-3-yl}-N-methylmethanamine or a salt thereof,
[5-(2-fluorophenyl)-4-methyl-1-(pyridin-3-ylsulfonyl)-1H-pyrrol-3-yl]-N-methylmethanamine or a salt thereof,
N-methyl-[2-methyl-1-(phenylsulfonyl)-5-(3-pyridyl)-1H-pyrrol-3-yl]methanamine or a salt thereof,
N-methyl-[2-methyl-5-(1-methyl-1H-pyrazol-4-yl)-1-(phenylsulfonyl)-1H-pyrrol-3-yl]methanamine or a salt thereof,
N-methyl-1-[4-methyl-1-(phenylsulfonyl)-5-(3-thienyl)-1H-pyrrol-3-yl]methanamine or a salt thereof,
1-[5-phenyl-1-({4-[(trifluoromethyl)sulfonyl]phenyl}sulfonyl)-1H-pyrrol-3-yl]-N-methylmethanamine or a salt thereof,
1-[5-phenyl-1-({3-[(trifluoromethyl)sulfonyl]phenyl}sulfonyl)-1H-pyrrol-3-yl]-N-methylmethanamine or a salt thereof,
1-[5-(2-fluorophenyl)-1-({3-[(trifluoromethyl)sulfonyl]phenyl}sulfonyl)-1H-pyrrol-3-yl]-N-methylmethanamine or a salt thereof,
N-methyl-1-[4-methyl-5-phenyl-1-(phenylsulfonyl)-1H-pyrrol-3-yl]methanamine or a salt thereof,
1-{1-[(3-chlorophenyl)sulfonyl]-4-methyl-5-phenyl-1H-pyrrol-3-yl}-N-methylmethanamine or a salt thereof,
5-({4-[(methylamino)methyl]-2-phenyl-1H-pyrrol-1-yl}sulfonyl)pyrimidin-2-amine or a salt thereof,
1-[(imidazo[1,2-a]pyrimidin-6-ylsulfonyl)-5-phenyl-1H-pyrrol-3-yl]-N-methylmethanamine or a salt thereof,
N-methyl-1-[1-(pyridazin-3-ylsulfonyl)-5-phenyl-1H-pyrrol-3-yl]methanamine or a salt thereof,
N,N-dimethyl-1-[5-phenyl-1-(phenylsulfonyl)-1H-pyrrol-3-yl]methanamine or a salt thereof,
N,N-dimethyl-1-[5-phenyl-1-(3-thienylsulfonyl)-1H-pyrrol-3-yl]methanamine or a salt thereof,
N,N-dimethyl-1-{5-phenyl-1-(3-pyridinesulfonyl)-1H-pyrrol-3-yl}methanamine or a salt thereof,
1-[4-ethyl-5-phenyl-1-(phenylsulfonyl)-1H-pyrrol-3-yl]-N-methylmethanamine or a salt thereof,
1-[4-isopropyl-5-phenyl-1-(phenylsulfonyl)-1H-pyrrol-3-yl]-N-methylmethanamine or a salt thereof,
2-({4-[(methylamino)methyl]-2-phenyl-1H-pyrrol-1-yl}sulfonyl)benzoic acid or a salt thereof,
3-({4-[(methylamino)methyl]-2-phenyl-1H-pyrrol-1-yl}sulfonyl)benzoic acid or a salt thereof,
3-({4-[(methylamino)methyl]-2-phenyl-1H-pyrrol-1-yl}sulfonyl)benzamide or a salt thereof,
N-cyclopropyl-3-({4-[(methylamino)methyl]-2-phenyl-1H-pyrrol-1-yl}sulfonyl)benzamide or a salt thereof,
N-methyl-3-({4-[(methylamino)methyl]-2-phenyl-1H-pyrrol-1-yl}sulfonyl)benzamide or a salt thereof,
N,N-dimethyl-3-({4-[(methylamino)methyl]-2-phenyl-1H-pyrrol-1-yl}sulfonyl)benzamide or a salt thereof,
N-methyl-1-(1-{[3-(morpholin-4-ylcarbonyl)phenyl]sulfonyl}-5-phenyl-1H-pyrrol-3-yl)methanamine or a salt thereof,
2-[3-({4-[(methylamino)methyl]-2-phenyl-1H-pyrrol-1-yl}sulfonyl)phenyl]propan-2-ol or a salt thereof,
2-fluoro-4-({4-[(methylamino)methyl]-2-phenyl-1H-pyrrol-1-yl}sulfonyl)benzonitrile or a salt thereof,
N-methyl-1-(5-phenyl-1-{[3-(1H-tetrazol-5-yl)phenyl]sulfonyl}-1H-pyrrol-3-yl)methanamine or a salt thereof,
2-({4-[(methylamino)methyl]-2-(pyridin-3-yl)-1H-pyrrol-1-yl}sulfonyl)benzonitrile or a salt thereof,
N-methyl-1-(1-{[3-(methylsulfonyl)phenyl]sulfonyl}-5-(3-thienyl)-1H-pyrrol-3-yl)methanamine or a salt thereof,
N-methyl-1-(1-{[3-(methylsulfonyl)phenyl]sulfonyl}-5-(pyridin-3-yl)-1H-pyrrol-3-yl)methanamine or a salt thereof,
1-[1-(2-chloropyridin-3-ylsulfonyl)-5-phenyl-1H-pyrrol-3-yl]-N-methylmethanamine or a salt thereof,
N-methyl-1-[1-(5-methyl-3-pyridinesulfonyl)-5-phenyl-1H-pyrrol-3-yl]methanamine or a salt thereof,
5-({4-[(methylamino)methyl]-2-phenyl-1H-pyrrol-1-yl}sulfonyl)pyridin-2-ol or a salt thereof,
5-({4-[(methylamino)methyl]-2-phenyl-1H-pyrrol-1-yl}sulfonyl)pyridine-2-carbonitrile or a salt thereof
N-methyl-1-{1-[(6-methylpyridin-3-yl)sulfonyl]-5-phenyl-1H-pyrrol-3-yl}methanamine or a salt thereof,
N-methyl-1-[1-(pyridin-3-ylsulfonyl)-5-(3-thienyl)-1H-pyrrol-3-yl]methanamine or a salt thereof,
1-[5-(4-fluorophenyl)-1-(pyridin-3-ylsulfonyl)-1H-pyrrol-3-yl]-N-methylmethanamine or a salt thereof,
N-methyl-1-[5-(2-methylphenyl)-1-(pyridin-3-ylsulfonyl)-1H-pyrrol-3-yl]methanamine or a salt thereof,
1-[5-(4-fluoro-2-methylphenyl)-1-(pyridin-3-ylsulfonyl)-1H-pyrrol-3-yl]-N-methylmethanamine or a salt thereof,
N-methyl-1-[5-(4-methyl-3-thienyl)-1-(pyridin-3-ylsulfonyl)-1H-pyrrol-3-yl]methanamine or a salt thereof,
3-[4-[(methylamino)methyl]-1-(pyridin-3-ylsulfonyl)-1H-pyrrol-2-yl]benzonitrile or a salt thereof,
1-[5-(2-chlorophenyl)-1-(pyridin-3-ylsulfonyl)-1H-pyrrol-3-yl]-N-methylmethanamine or a salt thereof,
1-[5-(2,4-difluorophenyl)-1-(pyridin-3-ylsulfonyl)-1H-pyrrol-3-yl]-N-methylmethanamine or a salt thereof,
1-[5-(2,5-difluorophenyl)-1-(pyridin-3-ylsulfonyl)-1H-pyrrol-3-yl]-N-methylmethanamine or a salt thereof,
1-[5-(4-chloro-2-fluorophenyl)-1-(pyridin-3-ylsulfonyl)-1H-pyrrol-3-yl]-N-methylmethanamine or a salt thereof,
1-[5-(3-fluorophenyl)-1-(pyridin-3-ylsulfonyl)-1H-pyrrol-3-yl]-N-methylmethanamine or a salt thereof,
N-methyl-1-[1-(phenylsulfonyl)-5-(pyrimidin-5-yl)-1H-pyrrol-3-yl]methanamine or a salt thereof,
N-methyl-1-[1-(phenylsulfonyl)-5-(pyridin-3-yl)-1H-pyrrol-3-yl]methanamine or a salt thereof,
{1-[5-(2-fluorophenyl)-2-methyl-1-(pyridin-3-ylsulfonyl)-1H-pyrrol-3-yl]-N-methylmethanamine or a salt thereof,
2,2,2-trifluoro-N-({1-[(4-methylphenyl)sulfonyl]-5-phenyl-1H-pyrrol-3-yl]methyl)ethaneamine or a salt thereof,
N-methyl-1-{1-[6-(methylamino)pyridin-3-ylsulfonyl]-5-phenyl-1H-pyrrol-3-yl}methanamine or a salt thereof,
N-methyl-1-{1-[2-(methylamino)pyridin-3-ylsulfonyl]-5-phenyl-1H-pyrrol-3-yl}methanamine or a salt thereof,
N-methyl-1-{1-[2-(methylamino)pyrimidin-3-ylsulfonyl]-5-phenyl-1H-pyrrol-3-yl}methanamine or a salt thereof,
N-methyl-1-[2-methyl-5-phenyl-1-(pyridin-3-ylsulfonyl)-1H-pyrrol-3-yl]methanamine or a salt thereof,
N-methyl-1-[1-(2-methylpyrimidin-5-ylsulfonyl)-5-phenyl-1H-pyrrol-3-yl]-methanamine or a salt thereof,
N-methyl-1-[4-methyl-5-phenyl-1-(pyridin-3-ylsulfonyl)-1H-pyrrol-3-yl]methanamine or a salt thereof,
N-methyl-1-[4-methyl-5-phenyl-1-(pyridin-2-ylsulfonyl)-1H-pyrrol-3-yl]methanamine or a salt thereof, N-methyl-1-[5-phenyl-1-(pyridazin-3-ylsulfonyl)-1H-pyrrol-3-yl]methanamine or a salt thereof,
N-methyl-1-(5-phenyl-1-{[5-(trifluoromethyl)pyridin-3-yl]sulfonyl}-1H-pyrrol-3-yl)methanamine or a salt thereof,
N-methyl-1-{1-[(2-methylpyridin-3-yl)sulfonyl]-5-phenyl-1H-pyrrol-3-yl}methanamine or a salt thereof,
1-[5-(2,6-difluorophenyl)-1-(pyridin-3-ylsulfonyl)-1H-pyrrol-3-yl]-N-methylmethanamine or a salt thereof,
1-[5-(4-cyclohexylphenyl)-1-(pyridin-3-ylsulfonyl)-1H-pyrrol-3-yl]-N-methylmethanamine or a salt thereof,
1-[4-fluoro-5-phenyl-1-(pyridin-3-ylsulfonyl)-1H-pyrrol-3-yl]-N-methylmethanamine or a salt thereof,
1-[4-fluoro-5-phenyl-1-(pyridin-3-ylsulfonyl)-1H-pyrrol-3-yl]-N-methylmethanamine or a salt thereof,
1-[4-fluoro-5-phenyl-1-(pyridin-3-ylsulfonyl)-1H-pyrrol-3-yl]-N-methylmethanamine or a salt thereof,
1-{5-(2-fluorophenyl)-1-[(6-methylpyridin-3-yl)sulfonyl]-1H-pyrrol-3-yl}-N-methylmethanamine or a salt thereof,
1-[(5-(2-fluorophenyl)-1-(pyridin-2-ylsulfonyl)-1H-pyrrol-3-yl]-N-methylmethanamine or a salt thereof,
1-{5-(2-fluorophenyl)-1-[(1-methyl-1H-pyrazol-4-yl)sulfonyl]-1H-pyrrol-3-yl}-N-methylmethanamine or a salt thereof,
N-methyl-1-[5-(2-methylphenyl)-1-(pyridin-3-ylsulfonyl)-1H-pyrrol-3-yl]methanamine or a salt thereof,
1-[4-chloro-5-(2-fluorophenyl)-1-(pyridin-3-ylsulfonyl)-1H-pyrrol-3-yl]-N-methylmethanamine or a salt thereof,
1-[4-fluoro-5-(2-fluorophenyl)-1-(pyridin-3-ylsulfonyl)-1H-pyrrol-3-yl]-N-methylmethanamine or a salt thereof,
1-[4-fluoro-5-(2-methylphenyl)-1-(pyridin-3-ylsulfonyl)-1H-pyrrol-3-yl]-N-methylmethanamine or a salt thereof,
1-[2-chloro-5-(2,6-difluorophenyl)-1-(pyridin-3-ylsulfonyl)-1H-pyrrol-3-yl]-N-methylmethanamine or a salt thereof,
1-[2-chloro-5-(2-fluorophenyl)-1-(pyridin-3-ylsulfonyl)-1H-pyrrol-3-yl]-N-methylmethanamine or a salt thereof,
1-{1-[(5-bromopyridin-3-yl)sulfonyl]-5-phenyl-1H-pyrrol-3-yl}-N-methylmethanamine or a salt thereof,
5-({4-[(methylamino)methyl]-2-phenyl-1H-pyrrol-1-yl}sulfonyl)nicotinonitrile or a salt thereof,
methyl 5-({4-[(methylamino)methyl]-2-phenyl-1H-pyrrol-1-yl}sulfonyl)nicotinate or a salt thereof,
N-methyl-1-{1-[(5-methylpyridin-3-yl)sulfonyl]-5-phenyl-1H-pyrrol-3-yl}methanamine or a salt thereof,
1-[5-(2,4-dimethylphenyl)-1-(pyridin-3-ylsulfonyl)-1H-pyrrol-3-yl]-N-methylmethanamine or a salt thereof,
N-methyl-1-{5-[4-(methylsulfonyl)phenyl]-1-(pyridin-3-ylsulfonyl)-1H-pyrrol-3-yl}methanamine or a salt thereof,
(2-{4-[(methylamino)methyl]-1-(pyridin-3-ylsulfonyl)-1H-pyrrol-2-yl}phenyl)methanol or a salt thereof,
N-methyl-1-[5-(4-methyl-3-thienyl)-1-(pyridin-3-ylsulfonyl)-1H-pyrrol-3-yl]methanamine or a salt thereof,
N-methyl-1-(5-phenyl-1-(pyridin-3-ylsulfonyl)-1H-pyrrol-3-yl)methanamine or a salt thereof,
1-[5-mesityl-1-(pyridin-3-ylsulfonyl)-1H-pyrrol-3-yl]-N-methylmethanamine or a salt thereof,
N-methyl-1-{5-[2-(methylthio)phenyl]-1-(pyridin-3-ylsulfonyl)-1H-pyrrol-3-yl}methanamine or a salt thereof,
N-methyl-1-{5-[2-(methylsulfonyl)phenyl]-1-(pyridin-3-ylsulfonyl)-1H-pyrrol-3-yl}methanamine or a salt thereof,
2-{4-[(methylamino)methyl]-1-(pyridin-3-ylsulfonyl)-1H-pyrrol-2-yl}benzonitrile or a salt thereof,
1-[5-(2,6-dimethylphenyl)-1-(pyridin-3-ylsulfonyl)-1H-pyrrol-3-yl]-N-methylmethanamine or a salt thereof,
N-methyl-1-{5-[2-(methylsulfinyl)phenyl]-1-(pyridin-3-ylsulfonyl)-1H-pyrrol-3-yl}methanamine or a salt thereof,
2-(2-fluorophenyl)-4-[(methylamino)methyl]-1-(pyridin-3-ylsulfonyl)-1H-pyrrole-3-carbonitrile or a salt thereof,
5-(2-fluorophenyl)-3-[(methylamino)methyl]-1-(pyridin-3-ylsulfonyl)-1H-pyrrole-2-carbonitrile or a salt thereof,
4-{4-[(methylamino)methyl]-1-(pyridin-3-ylsulfonyl)-1H-pyrrol-2-yl}benzonitrile or a salt thereof,
4-fluoro-3-{4-[(methylamino)methyl]-1-(pyridin-3-ylsulfonyl)-1H-pyrrol-2-yl}benzonitrile or a salt thereof,
1-[5-(2-fluoro-5-methoxyphenyl)-1-(pyridin-3-ylsulfonyl)-1H-pyrrol-3-yl]-N-methylmethanamine or a salt thereof,
1-(2-fluoro-3-{4-[(methylamino)methyl]-1-(pyridin-3-ylsulfonyl)-1H-pyrrol-2-yl}phenyl)ethanone or a salt thereof,
1-[5-(2-fluoropyridin-3-yl)-1-(pyridin-3-ylsulfonyl)-1H-pyrrol-3-yl]-N-methylmethanamine or a salt thereof,
1-[5-(3-fluoropyridin-4-yl)-1-(pyridin-3-ylsulfonyl)-1H-pyrrol-3-yl]-N-methylmethanamine or a salt thereof,
1-[5-(2-chloropyridin-3-yl)-1-(pyridin-3-ylsulfonyl)-1H-pyrrol-3-yl]-N-methylmethanamine or a salt thereof,
1-[5-(6-chloropyridin-3-yl)-1-(pyridin-3-ylsulfonyl)-1H-pyrrol-3-yl]-N-methylmethanamine or a salt thereof,
1-[5-(6'-chloro-2,3'-bipyridin-5-yl)-1-(pyridin-3-ylsulfonyl)-1H-pyrrol-3-yl]-N-methylmethanamine or a salt thereof,
1-{5-(2-fluoropyridin-3-yl)-1-[(6-methoxypyridin-3-yl)sulfonyl]-1H-pyrrol-3-yl}-N-methylmethanamine or a salt thereof,
(2-fluoro-3-{4-[(methylamino)methyl]-1-(pyridin-3-ylsulfonyl)-1H-pyrrol-2-yl}phenyl)methanol or a salt thereof,
1-(2-fluoro-3-{(4-[(methylamino)methyl]-1-(pyridin-3-ylsulfonyl)-1H-pyrrol-2-yl}phenyl)ethanol or a salt thereof,
1-[5-(2-fluoro-3-methoxyphenyl)-1-(pyridin-3-ylsulfonyl)-1H-pyrrol-3-yl]-N-methylmethanamine or a salt thereof,
1-[5-(2-fluoro-6-methoxyphenyl)-1-(pyridin-3-ylsulfonyl)-1H-pyrrol-3-yl]-N-methylmethanamine or a salt thereof,
1-{5-[4-(difluoromethoxy)phenyl]-1-(pyridin-3-ylsulfonyl)-1H-pyrrol-3-yl}-N-methylmethanamine or a salt thereof,
N-methyl-1-[5-(4-methylpyridin-3-yl)-1-(pyridin-3-ylsulfonyl)-1H-pyrrol-3-yl]methanamine or a salt thereof,
N-methyl-1-[5-(2-methylpyridin-3-yl)-1-(pyridin-3-ylsulfonyl)-1H-pyrrol-3-yl]methanamine or a salt thereof,
1-{5-(2-fluoropyridin-3-yl)-1-[(6-methylpyridin-3-yl)sulfonyl]-1H-pyrrol-3-yl}-N-methylmethanamine or a salt thereof,
1-[4-chloro-5-(2-fluoropyridin-3-yl)-1-(pyridin-3-ylsulfonyl)-1H-pyrrol-3-yl]-N-methylmethanamine or a salt thereof,
N-methyl-1-[1-(pyridin-3-ylsulfonyl)-5-(2-thienyl)-1H-pyrrol-3-yl]methanamine or a salt thereof,
N-methyl-1-[5-(3-methylpyridin-2-yl)-1-(pyridin-3-ylsulfonyl)-1H-pyrrol-3-yl]methanamine or a salt thereof,
2-fluoro-3-{4-[(methylamino)methyl]-1-(pyridin-3-ylsulfonyl)-1H-pyrrol-2-yl}benzonitrile or a salt thereof,
4-{4-[(methylamino)methyl]-1-(pyridin-3-ylsulfonyl)-1H-pyrrol-2-yl}thiophene-3-carbonitrile or a salt thereof,
1-[5-(2-fluoropyridin-3-yl)-1-(phenylsulfonyl)-1H-pyrrol-3-yl]-N-methylmethanamine or a salt thereof,
1-{1-[(2-fluorophenyl)sulfonyl]-5-(2-fluoropyridin-3-yl)-1H-pyrrol-3-yl}-N-methylmethanamine or a salt thereof,
1-[5-(2-fluoropyridin-3-yl)-1-(2-furylsulfonyl)-1H-pyrrol-3-yl]-N-methylmethanamine or a salt thereof,
1-(5-(2-fluoropyridin-3-yl)-1-{[3-(methylsulfonyl)phenyl]sulfonyl}-1H-pyrrol-3-yl)-N-methylmethanamine or a salt thereof,
1-[5-(2-fluoropyridin-3-yl)-1-(2-thienylsulfonyl)-1H-pyrrol-3-yl]-N-methylmethanamine or a salt thereof, 1-[1-(1,3-benzodioxol-5-ylsulfonyl)-5-(2-fluoropyridin-3-yl)-1H-pyrrol-3-yl]-N-methylmethanamine or a salt thereof,
1-(4-chloro-5-(2-fluoropyridin-3-yl)-1-{[3-(methylsulfonyl)phenyl]sulfonyl}-1H-pyrrol-3-yl)-N-methylmethanamine or a salt thereof,
1-[4-fluoro-5-(2-fluoropyridin-3-yl)-1-(pyridin-3-ylsulfonyl)-1H-pyrrol-3-yl]-N-methylmethanamine or a salt thereof,
1-{5-(2-chloropyridin-3-yl)-1-[(6-methylpyridin-3-yl)sulfonyl]-1H-pyrrol-3-yl}-N-methylmethanamine or a salt thereof,
3-{1-[(3-fluorophenyl)sulfonyl]-4-[(methylamino)methyl]-1H-pyrrol-2-yl}pyridine-2-carbonitrile or a salt thereof,
1-{5-(2-fluoropyridin-3-yl)-1-[(3-methoxyphenyl)sulfonyl]-1H-pyrrol-3-yl}-N-methylmethanamine or a salt thereof,
1-{1-[(3-fluorophenyl)sulfonyl]-5-(2-fluoropyridin-3-yl)-1H-pyrrol-3-yl}-N-methylmethanamine or a salt thereof,
1-[5-(2-fluoro-6-methylpyridin-3-yl)-1-(pyridin-3-ylsulfonyl)-1H-pyrrol-3-yl]-N-methylmethanamine or a salt thereof,
3-{4-[(methylamino)methyl]-1-(pyridin-3-ylsulfonyl)-1H-pyrrol-2-yl}pyridine-2-carbonitrile or a salt thereof,
1-[5-(2-chloropyridin-3-yl)-1-(phenylsulfonyl)-1H-pyrrol-3-yl]-N-methylmethanamine or a salt thereof,
3-{4-[(methylamino)methyl]-1-(phenylsulfonyl)-1H-pyrrol-2-yl}pyridine-2-carbonitrile or a salt thereof,
1-[5-(2-fluoropyridin-3-yl)-1-(3-thienylsulfonyl)-1H-pyrrol-3-yl]-N-methylmethanamine or a salt thereof,
3-({2-(2-fluoropyridin-3-yl)-4-[(methylamino)methyl]-1H-pyrrol-1-yl}sulfonyl)benzonitrile or a salt thereof,
1-[3-({2-(2-fluoropyridin-3-yl)-4-[(methylamino)methyl]-1H-pyrrol-1-yl}sulfonyl)phenyl]ethanone or a salt thereof,
1-{1-[(4-fluorophenyl)sulfonyl]-5-(2-fluoropyridin-3-yl)-1H-pyrrol-3-yl}-N-methylmethanamine or a salt thereof,
1-{1-[(2,3-difluorophenyl)sulfonyl]-5-(2-fluoropyridin-3-yl)-1H-pyrrol-3-yl}-N-methylmethanamine or a salt thereof,
1-{1-[(3,4-difluorophenyl)sulfonyl]-5-(2-fluoropyridin-3-yl)-1H-pyrrol-3-yl}-N-methylmethanamine or a salt thereof,
1-{1-[(3-fluoro-4-methylphenyl)sulfonyl]-5-(2-fluoropyridin-3-yl)-1H-pyrrol-3-yl}-N-methylmethanamine or a salt thereof,
1-{1-[(2,5-difluorophenyl)sulfonyl]-5-(2-fluoropyridin-3-yl)-1H-pyrrol-3-yl}-N-methylmethanamine or a salt thereof,
1-[5-(2-fluoropyridin-3-yl)-4-methyl-1-(pyridin-3-ylsulfonyl)-1H-pyrrol-3-yl]-N-methylmethanamine or a salt thereof,
1-[5-(2-fluoropyridin-3-yl)-4-methyl-1-(phenylsulfonyl)-1H-pyrrol-3-yl]-N-methylmethanamine or a salt thereof,
1-[4-fluoro-5-(2-fluoropyridin-3-yl)-1-(pyridin-3-ylsulfonyl)-1H-pyrrol-3-yl]-N-methylmethanamine or a salt thereof,
1-[4-fluoro-5-(2-fluoropyridin-3-yl)-1-(pyridin-3-ylsulfonyl)-1H-pyrrol-3-yl]-N-methylmethanamine or a salt thereof,
1-[4-fluoro-5-(2-fluoropyridin-3-yl)-1-(phenylsulfonyl)-1H-pyrrol-3-yl]-N-methylmethanamine or a salt thereof,
1-{4-fluoro-1-(phenylsulfonyl)-5-[2-(trifluoromethyl)pyridin-3-yl]-1H-pyrrol-3-yl}-N-methylmethanamine or a salt thereof,
1-{4-fluoro-1-(pyridin-3-ylsulfonyl)-5-[2-(trifluoromethyl)pyridin-3-yl]-1H-pyrrol-3-yl}-N-methylmethanamine or a salt thereof,
1-[5-(2-chloropyridin-3-yl)-4-fluoro-1-(phenylsulfonyl)-1H-pyrrol-3-yl]-N-methylmethanamine or a salt thereof,
3-[3-fluoro-4-[(methylamino)methyl]-1-(phenylsulfonyl)-1H-pyrrol-2-yl]pyridine-2-carbonitrile or a salt thereof,
1-{4-fluoro-5-(2-fluoropyridin-3-yl)-1-[(3-methoxyphenyl)sulfonyl]-1H-pyrrol-3-yl}-N-methylmethanamine or a salt thereof,
1-{4-fluoro-1-[(3-fluorophenyl)sulfonyl]-5-(2-fluoropyridin-3-yl)-1H-pyrrol-3-yl}-N-methylmethanamine or a salt thereof,
1-{5-(2-chloropyridin-3-yl)-4-fluoro-1-[(3-methoxyphenyl)sulfonyl]-1H-pyrrol-3-yl}-N-methylmethanamine or a salt thereof,
1-[5-(2-chloropyridin-3-yl)-4-fluoro-1-(pyridin-3-ylsulfonyl)-1H-pyrrol-3-yl]-N-methylmethanamine or a salt thereof,
1-{5-(2-chloropyridin-3-yl)-4-fluoro-1-[(3-fluorophenyl)sulfonyl]-1H-pyrrol-3-yl}-N-methylmethanamine or a salt thereof,
3-({2-(2-chloropyridin-3-yl)-3-fluoro-4-[(methylamino)methyl]-1H-pyrrol-1-yl}sulfonyl)benzonitrile or a salt thereof,
3-{3-fluoro-1-[(3-methoxyphenyl)sulfonyl]-4-[(methylamino)methyl]-1H-pyrrol-2-yl}pyridine-2-carbonitrile or a salt thereof,
3-{1-fluoro-1-[(3-fluorophenyl)sulfonyl]-4-[(methylamino)methyl]-1H-pyrrol-2-yl}pyridine-2-carbonitrile or a salt thereof,
3-{1-[(3-cyanophenyl)sulfonyl]-3-fluoro-4-[(methylamino)methyl]-1H-pyrrol-2-yl}pyridine-2-carbonitrile or a salt thereof,
3-[3-fluoro-4-[(methylamino)methyl]-1-(pyridin-3-ylsulfonyl)-1H-pyrrol-2-yl]pyridine-2-carbonitrile or a salt thereof,
3-({3-fluoro-2-(2-fluoropyridin-3-yl)-4-[(methylamino)methyl]-1H-pyrrol-1-yl}sulfonyl)benzonitrile or a salt thereof,
1-(4-fluoro-5-(2-fluoropyridin-3-yl)-1-{[3-(methylsulfonyl)phenyl]sulfonyl}-1H-pyrrol-3-yl)-N-methylmethanamine or a salt thereof,
3-({3-fluoro-2-(2-fluoropyridin-3-yl)-4-[((methylamino)methyl]-1H-pyrrol-1-yl}sulfonyl)-N-(2-hydroxyethyl)benzamide or a salt thereof,
[3-({3-fluoro-2-(2-fluoropyridin-3-yl)-4-[(methylamino)methyl]-1H-pyrrol-1-yl}sulfonyl)phenyl]methanol or a salt thereof,
3-({3-fluoro-2-(2-fluoropyridin-3-yl)-4-[methylamino)methyl]-1H-pyrrol-1-yl}sulfonyl)benzyl acetate or a salt thereof,
1-[4-fluoro-5-(2-fluoropyridin-3-yl)-1-(3-furylsulfonyl)-1H-pyrrol-3-yl]-N-methylmethanamine or a salt thereof,
1-[5-(2-fluoropyridin-3-yl)-1-(3-furylsulfonyl)-1H-pyrrol-3-yl]-N-methylmethanamine or a salt thereof,
1-[4-fluoro-5-(2-fluoropyridin-3-yl)-1-({3-[(methylsulfonyl)methyl]phenyl}sulfonyl)-1H-pyrrol-3-yl]-N-methylmethanamine or a salt thereof,
1-(4-fluoro-5-(2-fluoropyridin-3-yl)-1-{[3-(5-methyl-1,3,4-oxadiazol-2yl)phenyl]sulfonyl}-1H-pyrrol-3-yl)-N-methylmethanamine or a salt thereof,
3-({2-(2-chloropyridin-3-yl)-4-[(methylamino)methyl]-1H-pyrrol-1-yl}sulfonyl)benzonitrile or a salt thereof,
1-[1-(cyclohexylsulfonyl)-4-fluoro-5-(2-fluoropyridin-3-yl)-1H-pyrrol-3-yl]-N-methylmethanamine or a salt thereof,
1-[4-fluoro-5-(2-fluoropyridin-3-yl)-1-(piperidin-1-ylsulfonyl)-1H-pyrrol-3-yl]-N-methylmethanamine or a salt thereof, 1-{1-[(2,6-difluorophenyl)sulfonyl]-4-fluoro-5-(2-fluoropyridin-3-yl)-1H-pyrrol-3-yl}-N-methylmethanamine or a salt thereof,
1-{4-chloro-5-(2-fluoropyridin-3-yl)-1-[(1-methyl-1H-pyrazol-4-yl)sulfonyl]-1H-pyrrol-3-yl}-N-methylmethanamine or a salt thereof,
1-[4-fluoro-5-(2-fluoropyridin-3-yl)-1-(2-thienylsulfonyl)-1H-pyrrol-3-yl]-N-methylmethanamine or a salt thereof,
1-[4-fluoro-5-(2-fluoropyridin-3-yl)-1-(2-furylsulfonyl)-1H-pyrrol-3-yl]-N-methylmethanamine or a salt thereof,
1-[4-fluoro-5-(2-fluoropyridin-3-yl)-1-(3-thienylsulfonyl)-1H-pyrrol-3-yl]-N-methylmethanamine or a salt thereof,
1-{4-fluoro-5-(2-fluoropyridin-3-yl)-1-[(1-methyl-1H-pyrazol-4-yl)sulfonyl]-1H-pyrrol-3-yl}-N-methylmethanamine or a salt thereof,
Methyl 5-({3-fluoro-2-(2-fluoropyridin-3-yl)-4-[(methylamino)methyl]-1H-pyrrol-1-yl}sulfonyl)-2-furoate or a salt thereof,
[5-({3-fluoro-2-(2-fluoropyridin-3-yl)-4-[(methylamino)methyl]-1H-pyrrol-1-yl}sulfonyl)-2-furyl]methanol or a salt thereof,
[5-({3-fluoro-2-(2-fluoropyridin-3-yl)-4-[(methylamino)methyl]-1H-pyrrol-1-yl}sulfonyl)-2-furyl]methyl acetate or a salt thereof,
1-[4-fluoro-1-{[5-(fluoromethyl)-2-furyl]sulfonyl}-5-(2-fluoropyridin-3-yl)-1H-pyrrol-3-yl]-N-methylmethanamine or a salt thereof,
5-({3-fluoro-2-(2-fluoropyridin-3-yl)-4-[(methylamino)methyl]-1H-pyrrol-1-yl}sulfonyl)-2-furamide or a salt thereof,
5-({3-fluoro-2-(2-fluoropyridin-3-yl)-4-[(methylamino)methyl]-1H-pyrrol-1-yl}sulfonyl)-2-furonitrile or a salt thereof,
1-[1-{[5-(difluoromethyl)-2-furyl]sulfonyl}-4-fluoro-5-(2-fluoropyridin-3-yl)-1H-pyrrol-3-yl]-N-methylmethanamine or a salt thereof,
1-[5-({3-fluoro-2-(2-fluoropyridin-3-yl)-4-[(methylamino)methyl]-1H-pyrrol-1-yl}sulfonyl)-2-furyl]ethanol or a salt thereof,
1-[5-({3-fluoro-2-(2-fluoropyridin-3-yl)-4-[(methylamino)methyl]-1H-pyrrol-1-yl}sulfonyl)-2-furyl]ethanone or a salt thereof,
1-{4-fluoro-5-(2-fluoropyridin-3-yl)-1-[(2-methylfuran-3-yl)sulfonyl]-1H-pyrrol-3-yl}-N-methylmethanamine or a salt thereof,
1-[1-[(5-chloro-2-thienyl)sulfonyl]-4-fluoro-5-(2-fluoropyridin-3-yl)-1H-pyrrol-3-yl]-N-methylmethanamine or a salt thereof,
1-[1-[(5-bromo-2-thienyl)sulfonyl]-4-fluoro-5-(2-fluoropyridin-3-yl)-1H-pyrrol-3-yl]-N-methylmethanamine or a salt thereof,
1-[1-[(4-bromo-3-thienyl)sulfonyl]-4-fluoro-5-(2-fluoropyridin-3-yl)-1H-pyrrol-3-yl]-N-methylmethanamine or a salt thereof,
4-({3-fluoro-2-(2-fluoropyridin-3-yl)-4-[(methylamino)methyl]-1H-pyrrol-1-yl}sulfonyl)thiophene-3-carbonitrile or a salt thereof,
Methyl 3-({3-fluoro-2-(2-fluoropyridin-3-yl)-4-[(methylamino)methyl]-1H-pyrrol-1-yl}sulfonyl)thiophene-2-carboxylate or a salt thereof,
1-{5-(2-fluoropyridin-3-yl)-1-[(5-isoxazol-5-yl-2-thienyl)sulfonyl]-1H-pyrrol-3-yl}-N-methylmethanamine or a salt thereof,
1-{1-[(1-ethyl-1H-pyrazol-4-yl)sulfonyl]-4-fluoro-5-(2-fluoropyridin-3-yl)-1H-pyrrol-3-yl}-N-methylmethanamine or a salt thereof,
1-{1-[(1,5-dimethyl-1H-pyrazol-4-yl)sulfonyl]-4-fluoro-5-(2-fluoropyridin-3-yl)-1H-pyrrol-3-yl}-N-methylmethanamine or a salt thereof,
1-[1-{[1-(difluoromethyl)-1H-pyrazol-4-yl]sulfonyl}-4-fluoro-5-(2-fluoropyridin-3-yl)-1H-pyrrol-3-yl]-N-methylmethanamine or a salt thereof,
1-{4-fluoro-5-(2-fluoropyridin-3-yl)-1-[(1-methyl-1H-imidazol-2-yl)sulfonyl]-1H-pyrrol-3-yl}-N-methylmethanamine or a salt thereof,
1-[4-fluoro-5-(2-fluoropyridin-3-yl)-1-(1,3-thiazol-2-ylsulfonyl)-1H-pyrrol-3-yl]-N-methylmethanamine or a salt thereof,
1-{4-fluoro-5-(2-fluoropyridin-3-yl)-1-[(6-methoxypyridin-3-yl)sulfonyl]-1H-pyrrol-3-yl}-N-methylmethanamine or a salt thereof,
1-[4-fluoro-5-(2-fluoropyridin-3-yl)-1-(pyridin-2-ylsulfonyl)-1H-pyrrol-3-yl]-N-methylmethanamine or a salt thereof,
1-[1-[(2-chloropyridin-3-yl)sulfonyl]-4-fluoro-5-(2-fluoropyridin-3-yl)-1H-pyrrol-3-yl]-N-methylmethanamine or a salt thereof,
2-({3-fluoro-2-(2-fluoropyridin-3-yl)-4-[(methylamino)methyl]-1H-pyrrol-1-yl}sulfonyl)benzonitrile or a salt thereof,
4-({3-fluoro-2-(2-fluoropyridin-3-yl)-4-[(methylamino)methyl]-1H-pyrrol-1-yl}sulfonyl)phenol or a salt thereof,
1-[4-fluoro-5-(2-fluoropyridin-3-yl)-1-(morpholin-4-ylsulfonyl)-1H-pyrrol-3-yl]-N-methylmethanamine or a salt thereof,
1-[4-fluoro-5-(2-fluoropyridin-3-yl)-1-(pyrrolidin-1-ylsulfonyl)-1H-pyrrol-3-yl]-N-methylmethanamine or a salt thereof,
1-[5-(2-fluoropyridin-3-yl)-1-(1,3-thiazol-2-ylsulfonyl)-1H-pyrrol-3-yl]-N-methylmethanamine or a salt thereof,
3-{1-(2-furylsulfonyl)-4-[(methylamino)methyl]-1H-pyrrol-2-yl}pyridine-2-carbonitrile or a salt thereof,
3-{1-(3-furylsulfonyl)-4-[(methylamino)methyl]-1H-pyrrol-2-yl}pyridine-2-carbonitrile or a salt thereof,
3-[4-[(methylamino)methyl]-1-(2-thienylsulfonyl)-1H-pyrrol-2-yl]pyridine-2-carbonitrile or a salt thereof,
3-[4-[(methylamino)methyl]-1-(3-thienylsulfonyl)-1H-pyrrol-2-yl]pyridine-2-carbonitrile or a salt thereof,
3-{1-[(2,6-difluorophenyl)sulfonyl]-4-[(methylamino)methyl]-1H-pyrrol-2-yl}pyridine-2-carbonitrile or a salt thereof,
3-{1-[(2,4-difluorophenyl)sulfonyl]-4-[(methylamino)methyl]-1H-pyrrol-2-yl}pyridine-2-carbonitrile or a salt thereof,
3-{4-[(methylamino)methyl]-1-[(2-methylphenyl)sulfonyl]-1H-pyrrol-2-yl}pyridine-2-carbonitrile or a salt thereof,
3-{1-[(2-chlorophenyl)sulfonyl]-4-[(methylamino)methyl]-1H-pyrrol-2-yl}pyridine-2-carbonitrile or a salt thereof,
3-{1-[(2-fluorophenyl)sulfonyl]-4-[(methylamino)methyl]-1H-pyrrol-2-yl}pyridine-2-carbonitrile or a salt thereof,
3-{1-[(2-cyanophenyl)sulfonyl]-4-[(methylamino)methyl]-1H-pyrrol-2-yl}pyridine-2-carbonitrile or a salt thereof,
3-{1-[(6-methoxypyridin-3-yl)sulfonyl]-4-[(methylamino)methyl]-1H-pyrrol-2-yl}pyridine-2-carbonitrile or a salt thereof,
1-methyl-3-{4-[(methylamino)methyl]-1-(phenylsulfonyl)-1H-pyrrol-2-yl}pyridin-2(1H)-one or a salt thereof,
3-{4-[(dimethylamino)methyl]-1-(phenylsulfonyl)-1H-pyrrol-2-yl}-1-methylpyridin-2(1H)-one or a salt thereof,
3-[4-[(methylamino)methyl]-1-(phenylsulfonyl)-1H-pyrrol-2-yl]pyridin-2(1H)-one or a salt thereof, 1-{4-fluoro-5-(2-fluoropyridin-3-yl)-1-[(6-fluoropyridin-2-yl)sulfonyl]-1H-pyrrol-3-yl}-N-methylmethanamine or a salt thereof, 1-{4-fluoro-5-(2-fluoropyridin-3-yl)-1-[(6-methoxypyridin-2-yl)sulfonyl]-1H-pyrrol-3-yl}-N-methylmethanamine or a salt thereof, 1-{4-fluoro-5-(2-fluoropyridin-3-yl)-1-[(6-methylpyridin-2-yl)sulfonyl]-1H-pyrrol-3-yl}-N-methylmethanamine or a salt thereof.

In addition, the compounds shown in the following Tables 1-1 to 1-4 and salts thereof are also preferable as a pharmaceutically active ingredient having a primary or secondary amino group in the pharmaceutical composition of the present invention.

TABLE 1-1

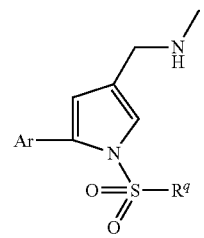

| Ar | R<sup>q</sup> | HPLC purity (%) | m/e (M<sup>+</sup> + 1) |
|---|---|---|---|
| 3-pyridyl | methoxy | 97 | 358 |
| 3-thienyl | methoxy | 96 | 363 |
| p-tolyl | methoxy | 96 | 371 |
| 4-cyanophenyl | methoxy | 100 | 382 |
| 3,5-dimethylphenyl | methoxy | 96 | 385 |
| 4-methoxyphenyl | methoxy | 97 | 387 |
| 4-chlorophenyl | methoxy | 91 | 391 |
| 4-acetylphenyl | methoxy | 98 | 399 |
| 3-acetylphenyl | methoxy | 97 | 399 |
| 4-aminocarbonylphenyl | methoxy | 98 | 400 |
| 4-(N,N-dimethylamino)phenyl | methoxy | 98 | 400 |
| 4-(methylthio)phenyl | methoxy | 81 | 403 |
| benzo[b]thiophen-2-yl | methoxy | 99 | 413 |
| 3-(acetylamino)phenyl | methoxy | 93 | 414 |
| 2,4-dimethoxyphenyl | methoxy | 97 | 417 |
| 3-(trifluoromethyl)phenyl | methoxy | 94 | 425 |
| 4-(trifluoromethoxy)phenyl | methoxy | 87 | 441 |
| 2-isopropoxyphenyl | methoxy | 99 | 415 |
| 3-(6-methoxy)pyridyl | methoxy | 93 | 388 |
| 3-cyanophenyl | methoxy | 98 | 382 |
| 3-furyl | methyl | 98 | 331 |

TABLE 1-2

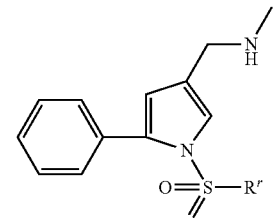

| Ar | R<sup>q</sup> | HPLC purity (%) | m/e (M<sup>+</sup> + 1) |
|---|---|---|---|
| 3-pyridyl | methyl | 100 | 342 |
| 3-thienyl | methyl | 99 | 347 |
| p-tolyl | methyl | 96 | 355 |

TABLE 1-2-continued

| Ar | R<sup>q</sup> | HPLC purity (%) | m/e (M<sup>+</sup> + 1) |
|---|---|---|---|
| 4-cyanophenyl | methyl | 98 | 366 |
| 3,5-dimethylphenyl | methyl | 93 | 369 |
| 4-methoxyphenyl | methyl | 99 | 371 |
| 4-chlorophenyl | methyl | 93 | 375 |
| 4-acetylphenyl | methyl | 98 | 383 |
| 3-acetylphenyl | methyl | 98 | 383 |
| 4-aminocarbonylphenyl | methyl | 98 | 384 |
| 4-(N,N-dimethylamino)phenyl | methyl | 99 | 384 |
| 4-(methylthio)phenyl | methyl | 96 | 387 |
| benzo[b]thiophen-2-yl | methyl | 99 | 397 |
| 3-(acetylamino)phenyl | methyl | 89 | 398 |
| 2,4-dimethoxyphenyl | methyl | 99 | 401 |
| 3-(trifluoromethyl)phenyl | methyl | 81 | 409 |
| 4-(trifluoromethoxy)phenyl | methyl | 89 | 425 |
| 2-isopropoxyphenyl | methyl | 92 | 399 |
| 3-(hydroxymethyl)phenyl | methyl | 91 | 371 |
| 3-(6-methoxy)pyridyl | methyl | 99 | 372 |
| 3-cyanophenyl | methyl | 98 | 366 |

TABLE 1-3

| R<sup>r</sup> | HPLC purity (%) | m/e (M<sup>+</sup> + 1) |
|---|---|---|
| 4-biphenyl | 100 | 403 |
| m-toluyl | 100 | 341 |
| 2,4-dichlorophenyl | 100 | 395 |
| 2-methoxy-4-methylphenyl | 100 | 371 |
| 2-chlorophenyl | 100 | 361 |
| 4-carboxyphenyl | 99 | 371 |
| 3,5-dimethylphenyl | 100 | 355 |
| 3,5-dichlorophenyl | 93 | 395 |
| 4-tert-butylphenyl | 99 | 383 |
| n-propyl | 99 | 293 |
| ethyl | 100 | 279 |
| 3,4-dimethoxyphenyl | 95 | 387 |
| 3-chlorophenyl | 100 | 361 |
| 4-cyanophenyl | 98 | 352 |
| 3-cyanophenyl | 98 | 352 |
| 2-cyanophenyl | 99 | 352 |
| 2,1,3-benzothiadiazol-4-yl | 96 | 385 |
| 3,4-dichlorophenyl | 99 | 395 |
| 3-thienyl | 96 | 333 |
| phenyl | 100 | 327 |

TABLE 1-4

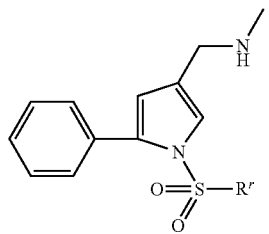

| R$^r$ | HPLC purity (%) | LC/MS m/e (M$^+$ + 1) |
|---|---|---|
| 1-naphthyl | 97 | 377 |
| p-styryl | 99 | 353 |
| 4-ethylphenyl | 100 | 355 |
| 2,5-dichlorophenyl | 99 | 395 |
| isopropyl | 100 | 293 |
| 2-(1-naphthyl)ethyl | 99 | 405 |
| 2-naphthyl | 99 | 377 |
| 2,4,6-trimethylphenyl | 100 | 369 |
| 4-bromophenyl | 99 | 405 |

Of these, preferred are the following compounds.
N-methyl-1-[1-(phenylsulfonyl)-5-(3-thienyl)-1H-pyrrol-3-yl]methanamine or a salt thereof,
N-methyl-1-[5-phenyl-1-(3-thienylsulfonyl)-1H-pyrrol-3-yl]methanamine or a salt thereof,
N-methyl-1-(1-{[3-(methylsulfonyl)phenyl]sulfonyl}-5-phenyl-1H-pyrrol-3-yl)methanamine or a salt thereof,
1-[1-(1-benzothien-2-ylsulfonyl)-5-phenyl-1H-pyrrol-3-yl]-N-methylmethanamine or a salt thereof,
1-[5-(2-fluorophenyl)-1-{[3-(methylsulfonyl)phenyl]sulfonyl}-1H-pyrrol-3-yl]-N-methylmethanamine or a salt thereof,
1-{5-(2-fluorophenyl)-1-[(2-fluorophenyl)sulfonyl]-1H-pyrrol-3-yl}-N-methylmethanamine or a salt thereof,
N-methyl-3-({4-[(methylamino)methyl]-2-phenyl-1H-pyrrol-1-yl}sulfonyl)benzamide or a salt thereof,
1-{5-(2-fluorophenyl)-1-[(6-methylpyridin-3-yl)sulfonyl]-1H-pyrrol-3-yl}-N-methylmethanamine or a salt thereof,
1-[4-fluoro-5-phenyl-1-(pyridin-3-ylsulfonyl)-1H-pyrrol-3-yl]-N-methylmethanamine or a salt thereof,
N-methyl-1-[5-(4-methyl-3-thienyl)-1-(pyridin-3-ylsulfonyl)-1H-pyrrol-3-yl]methanamine or a salt thereof,
1-[5-(2-fluoropyridin-3-yl)-1-(pyridin-3-ylsulfonyl)-1H-pyrrol-3-yl]-N-methylmethanamine or a salt thereof,
1-[5-(2-fluorophenyl)-1-(pyridin-3-ylsulfonyl)-1H-pyrrol-3-yl]-N-methylmethanamine or a salt thereof,
N-methyl-1-[5-(2-methylphenyl)-1-(pyridin-3-ylsulfonyl)-1H-pyrrol-3-yl]methanamine or a salt thereof,
1-[5-(2-Fluoropyridin-3-yl)-1-(phenylsulfonyl)-1H-pyrrol-3-yl]-N-methylmethanamine or a salt thereof,
1-[4-fluoro-5-(2-fluoropyridin-3-yl)-1-(pyridin-3-ylsulfonyl)-1H-pyrrol-3-yl]-N-methylmethanamine or a salt thereof,
1-[5-(2-chloropyridin-3-yl)-1-(phenylsulfonyl)-1H-pyrrol-3-yl]-N-methylmethanamine or a salt thereof,
3-{4-[(methylamino)methyl]-1-(phenylsulfonyl)-1H-pyrrol-2-yl}pyridine-2-carbonitrile or a salt thereof, or
1-{1-[(4-fluorophenyl)sulfonyl]-5-(2-fluoropyridin-3-yl)-1H-pyrrol-3-yl}-N-methylmethanamine or a salt thereof
1-[4-fluoro-5-(2-fluoropyridin-3-yl)-1-(3-furylsulfonyl)-1H-pyrrol-3-yl]-N-methylmethanamine or a salt thereof,
1-{4-fluoro-5-(2-fluoropyridin-3-yl)-1-[(2-methylfuran-3-yl)sulfonyl]-1H-pyrrol-3-yl}-N-methylmethanamine or a salt thereof,
1-[1-{[1-(difluoromethyl)-1H-pyrazol-4-yl]sulfonyl}-4-fluoro-5-(2-fluoropyridin-3-yl)-1H-pyrrol-3-yl]-N-methylmethanamine or a salt thereof,
1-[4-fluoro-5-(2-fluoropyridin-3-yl)-1-(pyridin-2-ylsulfonyl)-1H-pyrrol-3-yl]-N-methylmethanamine or a salt thereof.

Most preferred as a pharmaceutically active ingredient having a primary or secondary amino group in the pharmaceutical composition of the present invention are
1-{5-(2-fluorophenyl)-1-[(6-methylpyridin-3-yl)sulfonyl]-1H-pyrrol-3-yl}-N-methylmethanamine or a salt thereof,
1-[4-fluoro-5-phenyl-1-(pyridin-3-ylsulfonyl)-1H-pyrrol-3-yl]-N-methylmethanamine or a salt thereof,
N-methyl-1-[5-(4-methyl-3-thienyl)-1-(pyridin-3-ylsulfonyl)-1H-pyrrol-3-yl]methanamine or a salt thereof,
1-[5-(2-fluorophenyl)-1-(pyridin-3-ylsulfonyl)-1H-pyrrol-3-yl]-N-methylmethanamine or a salt thereof,
N-methyl-1-[5-(2-methylphenyl)-1-(pyridin-3-ylsulfonyl)-1H-pyrrol-3-yl]methanamine or a salt thereof, and
1-[4-fluoro-5-(2-fluoropyridin-3-yl)-1-(pyridin-3-ylsulfonyl)-1H-pyrrol-3-yl]-N-methylmethanamine or a salt thereof, and more preferred are
1-{5-(2-fluorophenyl)-1-[(6-methylpyridin-3-yl)sulfonyl]-1H-pyrrol-3-yl}-N-methylmethanamine or a salt thereof,
1-[4-fluoro-5-phenyl-1-(pyridin-3-ylsulfonyl)-1H-pyrrol-3-yl]-N-methylmethanamine or a salt thereof,
N-methyl-1-[5-(4-methyl-3-thienyl)-1-(pyridin-3-ylsulfonyl)-1H-pyrrol-3-yl]methanamine or a salt thereof,
1-[5-(2-fluorophenyl)-1-(pyridin-3-ylsulfonyl)-1H-pyrrol-3-yl]-N-methylmethanamine or a salt thereof, and
N-methyl-1-[5-(2-methylphenyl)-1-(pyridin-3-ylsulfonyl)-1H-pyrrol-3-yl]methanamine or a salt thereof.

Examples of the salt of the above-mentioned "nonpeptidic pharmaceutically active ingredient having a primary or secondary amino group" include metal salt, ammonium salt, salt with organic base, salt with inorganic acid, salt with organic acid, salt with basic or acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like. Preferable examples of the salt with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with an inorganic acid include salts with hydrochloric acid, hydrobromic acid, nitric acid, sulfuric acid, phosphoric acid and the like. Preferable examples of the salt with an organic acid include salts with adipic acid, ascorbic acid, benzoic acid, oleic acid, succinic acid, acetic acid, tartaric acid, sorbic acid, fumaric acid, lactic acid, maleic acid, malonic acid, citric anhydride, maleic anhydride, phthalic acid, phthalic anhydride, malic acid, formic acid, trifluoroacetic acid, oxalic acid, methanesulfonic acid, benzenesulfonic acid, p-toluenesulfonic acid and the like. Preferable examples of the salt with a basic amino acid include salts with arginine, lysine, ornithine and the like, and preferable examples of the salt with an acidic amino acid include salts with aspartic acid, glutamic acid and the like.

Of these, a salt with an organic acid is preferable for the pharmaceutical composition of the present invention. Examples of the salt with an organic acid for such nonpeptidic pharmaceutically active ingredient having a primary or secondary amino group include salts with adipic acid, ascorbic acid, benzoic acid, oleic acid, succinic acid, acetic acid, tartaric acid, sorbic acid, fumaric acid, lactic acid, maleic acid, malonic acid, citric anhydride, maleic anhydride, phthalic anhydride, malic acid and the like. In addition, of the organic acid salts, a salt with an unsaturated carboxylic acid is particularly preferably used. Examples of the salt with such unsaturated carboxylic acid include salts with fumaric acid, sorbic acid, maleic acid, oleic acid, succinic acid, tartaric acid and the like. Of these, the salts with fumaric acid, succinic acid and tartaric acid are preferable.

In the whole pharmaceutical composition of the present invention (a pharmaceutical composition containing at least a nonpeptidic pharmaceutically active ingredient having a primary or secondary amino group, an excipient and an acidic compound), the content (%) of the "pharmaceutically active ingredient having a primary or secondary amino group or a salt thereof" is preferably 0.1-80%, further preferably 0.1-60%, particularly preferably 0.1-50% (in the present specification, "%" means weight percent unless otherwise specified).

[2. Excipient (Second Component)]

As the "excipient", which is the second component of the pharmaceutical composition of the present invention, preferred is an excipient having pH 4.5 or above when dissolved or dispersed in water.

Examples of such excipient include mannitol, croscarmellose sodium, hydroxypropylcellulose, hydroxypropylmethylcellulose, polyethylene glycol, polyvinylpyrrolidone, crystalline cellulose, lactose, sucrose, starch, cornstarch, titanium oxide ($TiO_2$), light anhydrous silicic acid and the like. These excipients may be used alone or two or more kinds thereof may be used in combination. Of these, as the excipient, mannitol, hydroxypropylcellulose and crystalline cellulose are preferable.

The content (%) of the excipient in the whole pharmaceutical composition of the present invention is preferably 20-99.8%, further preferably 40-99.8%, particularly preferably 50-99.8%.

In the pharmaceutical composition of the present invention, the mixing ratio of the "excipient" to the "nonpeptidic pharmaceutically active ingredient having a primary or secondary amino group or a salt thereof" (to be abbreviated as "pharmaceutically active ingredient") is preferably pharmaceutically active ingredient:excipient=1:0.25-1:998, further preferably 1:0.67-1:998, particularly preferably 1:1-1:998. The above-mentioned mixing ratio is a weight ratio.

[3. Acidic Compound (Third Component)]

Here, the term acidic compound has a general meaning. Specifically, for example, the term can be defined based on the value of pKa (logarithm of reciprocal of acid dissociation constant) of the compound. The "acidic compound" means a compound having a partial structure having pKa of not more than 6.5 (preferably not more than 5.5). The acidic compound to be used in the present invention may be either a solid or a liquid at ambient temperature (15-25° C.). The above-mentioned "partial structure having pKa" refers to a partial structure that releases $H^+$.

The above-mentioned "nonpeptidic pharmaceutically active ingredient having a primary or secondary amino group (first component)" has a "primary or secondary amino group having high nucleophilicity". Thus, when a trace amount of a basic component is contained in the excipient, the basic component acts as a basic catalyst and highly possibly causes problems of Michael addition of, for example, fumaric acid and the like to an α or β-unsaturated carbonyl compound (nucleophilic addition reaction of a carbon at the end of a conjugated system in conjugation with an electron-withdrawing substituent) and the like.

Examples of the above-mentioned basic compound which is contained in the excipient and having a possibility of acting as a basic catalyst include a basic salt, oxide and hydroxide, such as metal carbonates such as alkali metal hydrogen carbonates (e.g., sodium hydrogen carbonate etc.), alkali metal carbonates (e.g., sodium carbonate, potassium carbonate etc.), alkaline earth metal carbonates (e.g., calcium carbonate, magnesium carbonate etc.) and the like; di-salt hydrogen phosphate such as di-alkali metal salt hydrogen phosphates (e.g., disodium hydrogen phosphate, dipotassium hydrogen phosphate, etc.) and the like; silicates such as calcium silicate, magnesium silicate and the like; metal oxides such as magnesium oxide and the like; metal hydroxides such as sodium hydroxide, calcium hydroxide, magnesium hydroxide, aluminum hydroxide and the like; citrates such as sodium citrate and the like; tartrates such as sodium dl- and l-tartrates and the like; pantothenates such as calcium pantothenate etc, and the like.

Therefore, a stabilizer is added to the pharmaceutical composition of the present invention. The stabilizer stabilizes the pharmaceutical composition by preventing a reaction of an amino group in the nonpeptidic pharmaceutically active ingredient having a primary or secondary amino group with an α or β-unsaturated carbonyl compound. As the stabilizer, any substance can be used as long as it is an acidic compound which can protonate, by releasing $H^+$, the amino group of the nonpeptidic pharmaceutically active ingredient having a primary or secondary amino group, preferably an organic acid or a salt thereof (particularly organic acid).

Specifically, the pharmaceutical composition of the present invention characteristically contains an acidic compound (third component) as the stabilizer in addition to a pharmaceutical composition containing a nonpeptidic pharmaceutically active ingredient having a primary or secondary amino group (first component) and an excipient (second component).

As the "acidic compound" to be used in the present invention, an inorganic acid such as hydrochloric acid, hydrobromic acid, nitric acid, sulfuric acid, phosphoric acid and the like, or an organic acid similar to the organic acid exemplified in the explanation of the above-mentioned "salt with an organic acid of a nonpeptidic pharmaceutically active ingredient having a primary or secondary amino group" can be used. Particularly preferable examples thereof include edible organic acids such as adipic acid, ascorbic acid, benzoic acid, oleic acid, succinic acid, acetic acid, tartaric acid, sorbic acid, fumaric acid, lactic acid, maleic acid, malonic acid, citric anhydride, maleic anhydride, phthalic anhydride, malic acid and the like. In addition, an organic acid such as formic acid, trifluoroacetic acid, phthalic acid, oxalic acid, methanesulfonic acid, benzenesulfonic acid, p-toluenesulfonic acid and the like can also be used for the object of stabilization of the pharmaceutical composition.

The organic acid may be a salt. Examples of the salt with an organic acid include sodium ascorbate, sodium fumarate, and those similar to the salts exemplified in the above-mentioned "salt with an organic acid of a nonpeptidic pharmaceutically active ingredient having a primary or secondary amino group". Of these, those similar to the salts exemplified in the above-mentioned "salt with an organic acid of a nonpeptidic pharmaceutically active ingredient having a primary or secondary amino group" are preferable. In addition, the salt with an organic acid similar to the above-mentioned respective organic acids are preferable.

These organic acids and salts thereof may be used alone or two or more kinds thereof may be used simultaneously. In addition, the organic acid to be used for the above-mentioned "salt with an organic acid of a nonpeptidic pharmaceutically active ingredient having a primary or secondary amino group" and an organic acid to be used as a stabilizer may be the same or different.

As the organic acid to be used for the above-mentioned "salt with an organic acid of a nonpeptidic pharmaceutically active ingredient having a primary or secondary amino group", preferred are fumaric acid, malonic acid, citric anhydride, maleic anhydride, succinic acid and tartaric acid, more preferred are fumaric acid, citric anhydride, succinic acid, tartaric acid, and still more preferred are fumaric acid, succinic acid and tartaric acid.

The pH of an excipient or acidic compound is measured under the following conditions. To be specific, the pH of an aqueous solution or dispersion obtained by dissolving or dispersing an excipient in water at 1% w/v is measured at 25° C. with a commercially available pH meter.

In the pharmaceutical composition of the present invention, the pKa value of the "nonpeptidic pharmaceutically active ingredient having a primary or secondary amino group" is preferably higher for stabilization of the pharmaceutical composition than that of the "organic acid or a salt thereof" to be added.

Particularly, the difference between the pKa value of the "nonpeptidic pharmaceutically active ingredient having a primary or secondary amino group" and that of the "organic acid" is preferably not less than 4, further preferably not less than 5, particularly preferably not less than 6.

For example, when the pharmaceutically active ingredient is represented by the formula (A2), an "organic acid" is preferably used as an acidic compound. Examples of the "organic acid" include edible organic acids such as adipic acid, ascorbic acid, benzoic acid, oleic acid, succinic acid, acetic acid, tartaric acid, sorbic acid, fumaric acid, lactic acid, maleic acid, malonic acid, citric acid, malic acid and the like. In addition, organic acids such as formic acid, trifluoroacetic acid, phthalic acid, oxalic acid, methanesulfonic acid, benzenesulfonic acid, p-toluenesulfonic acid and the like can also be used for stabilizing the pharmaceutical composition. Of these, fumaric acid is particularly preferable.

The content (%) of the acidic compound in the whole pharmaceutical composition of the present invention is preferably 0.1-20% (more preferably 0.1-19%), further preferably 1-10%, particularly preferably 2-10%. In another embodiment, it is 0.01-50%, preferably 0.05-19%, more preferably 0.1-10%.

In the pharmaceutical composition of the present invention, the mixing ratio of the "acidic compound" to the "nonpeptidic pharmaceutically active ingredient having a primary or secondary amino group" (to be abbreviated as a "pharmaceutically active ingredient") is preferably pharmaceutically active ingredient:acidic compound=1:0.00125-1:200, further preferably 1:0.0167-1:200, particularly preferably 1:0.04-1:100.

In the pharmaceutical composition of the present invention, the mixing ratio of the "acidic compound" to the "excipient" is preferably excipient:acidic compound=1:0.0001-1:1, further preferably 1:0.01-1:0.5, particularly preferably 1:0.02-1:0.2.

When producing the pharmaceutical composition of the present invention, the "acidic compound" may be added as a powder in a granulation step or a mixing step. In addition, an acidic compound can be sprayed by dissolving or dispersing in a binder solution in the granulation step or in a film coating solution in a film coating step.

The above-mentioned "binder solution" is prepared by dissolving a binder in an aqueous solution. Examples of the "binder" include hydroxypropylcellulose, hydroxypropylmethylcellulose, crystalline cellulose, starch, polyvinylpyrrolidone, gum arabic powder, gelatin, pullulan, low-substituted hydroxypropylcellulose and the like.

The above-mentioned "film coating solution" is prepared, for example, by dissolving or suspending a film coating polymer in a solvent. The film coating solution may further contain a colorant (preferably, diiron trioxide and yellow ferric oxide), a light shielding agent (preferably, titanium oxide) and the like. Examples of the "film coating polymer" include hydroxypropylmethylcellulose, ethylcellulose, hydroxymethylcellulose, hydroxypropylcellulose, hydroxypropylmethylcellulose acetate succinate, acrylic resin (methacrylic acid-acrylic acid copolymer, aminoalkylmethacrylate copolymer etc.), shellac, polyvinyl acetate phthalate, gum arabic, cellulose acetate phthalate, hydroxypropylmethylcellulose phthalate, carboxymethylethyl cellulose and the like. Examples of the "solvent" include water, alcohols (e.g., ethanol, isopropyl alcohol, n-propyl alcohol, methanol, etc.), acetone, ethyl acetate, dichloromethane, chloroform, hexane, toluene, heptane and the like. The amount of the "film coating polymer" to be used can be determined according to the kind of the solid preparation. For example, when the solid preparation is a tablet, the amount is about 0.5-10 wt % of the tablet. The spray temperature is generally 25-80° C., the spray time is generally 5 min-24 hr, and the drying conditions are generally at 30-80° C. for about 1 min-24 hr. The film coating layer of the present invention can be generally formed at ratio of 1-10 parts by weight, preferably 2-6 parts by weight, per 100 parts by weight of the solid preparation (preferably tablet, more preferably ellipse or round tablet) of the present invention.

To use the pharmaceutical composition of the present invention as a more stable pharmaceutical composition, the content of the decomposed product of the pharmaceutically active ingredient in the whole pharmaceutical composition does not desirably exceed, according to the ICH guideline, a lower of 1.0% and a total daily ingestion amount of 5 μg when the pharmaceutically active ingredient to be administered per day is <1 mg, a lower of 0.5% and a total daily ingestion amount of 20 μg when the pharmaceutically active ingredient to be administered per day is 1 mg-10 mg, a lower of 0.2% and a total daily ingestion amount of 2 mg when the pharmaceutically active ingredient to be administered per day is >10 mg-2 g, 0.10% when the pharmaceutically active ingredient to be administered per day is >2 g, a lower of 1.0% and a total daily ingestion amount of 50 μg when the pharmaceutically active ingredient to be administered per day is <10 mg, a lower of 0.5% and a total daily ingestion amount of 200 μg when the pharmaceutically active ingredient to be administered per day is 10 mg-100 mg, a lower of 0.2% and a total daily ingestion amount of 3 mg when the pharmaceutically active ingredient to be administered per day is >100 mg-2 g, and 0.15% when the pharmaceutically active ingredient to be administered per day is >2 g.

The preservation environment of a pharmaceutical product after being placed in the market by a manufacturer is difficult to control. To maintain the quality of a pharmaceutical product, therefore, the content of the decomposed product is preferably as small as possible under any temperature and humidity conditions (60° C., 40° C., 75% RH, 30° C., 65% RH etc.) and in any packaging form (open bottle, closed bottle etc.).

The pharmaceutical composition of the present invention shows a small content of a decomposed product under any conditions (60° C., 40° C., 75% RH, 30° C., 65% RH etc.) whether in an open bottle or a closed bottle.

Therefore, the pharmaceutical composition of the present invention can retain preservation stability and can maintain high quality under any conditions.

The pharmaceutical composition of the present invention has low toxicity, and can be safely administered orally or parenterally (e.g., topical, rectal, intravenous administration etc.) as it is or in the form of a pharmaceutical composition containing a pharmacologically acceptable carrier according to a method known per se, for example, preparations such as tablet (core tablet, sugar-coated tablet, film-coated tablet etc.), powder, granule, capsule (including soft capsule), orally disintegrating tablet, liquid, injection, suppository, sustained-release preparation, plaster and the like. The pharmaceutical composition of the present invention is preferably administered as an oral preparation such as tablet, granule, capsule and the like. Of these, a solid preparation such as tablet, capsule and the like is preferable, a sugar-coated tablet, a film-coated tablet and the like are especially preferable, and a film-coated tablet is particularly preferable.

Examples of the pharmacologically acceptable carrier that can be used for the production of the pharmaceutical composition of the present invention include various organic or inorganic carrier substances conventionally used as preparation materials. For example, filler, lubricant, binder, disintegrant, water-soluble polymer and basic inorganic salt for solid preparations; solvent, solubilizing agent, suspending agent, isotonicity agent, buffering agent and soothing agent for liquid preparation and the like can be mentioned. Where necessary, general additives such as preservative, antioxidant, colorant, sweetening agent, foaming agent, flavor and the like can also be used.

Examples of the "lubricant" include magnesium stearate, sucrose fatty acid ester, polyethylene glycol, talc, stearic acid and the like.

Examples of the "binder" include hydroxypropylcellulose, hydroxypropylmethylcellulose, crystalline cellulose, starch, polyvinylpyrrolidone, gum arabic powder, gelatin, pullulan, low-substituted hydroxypropylcellulose and the like.

Examples of the "disintegrant" include (1) crospovidone, (2) disintegrants referred to as super disintegrants such as croscarmellose sodium (FMC-Asahi Kasei), carmellose calcium (Gotoku Yakuhin) and the like, (3) sodium carboxymethyl starch (e.g., manufactured by Matsutani Chemical Industry Co., Ltd.), (4) low-substituted hydroxypropylcellulose (e.g., manufactured by Shin-Etsu Chemical Co., Ltd.), (5) cornstarch and the like. The "crospovidone" may be any crosslinked polymer having a chemical name of 1-ethenyl-2-pyrrolidinone homopolymer including polyvinylpolypyrrolidone (PVPP) and 1-vinyl-2-pyrrolidinone homopolymer. Specific examples thereof include Kollidon CL (manufactured by BASF), Polyplasdone XL (manufactured by ISP), Polyplasdone XL-10 (manufactured by ISP), Polyplasdone INF-10 (manufactured by ISP) and the like.

Examples of the "water-soluble polymer" include ethanol-soluble water-soluble polymer [e.g., cellulose derivatives such as hydroxypropylcellulose (hereinafter to be sometimes indicated as HPC) and the like, polyvinylpyrrolidone and the like], ethanol-insoluble water-soluble polymer [e.g., cellulose derivative such as hydroxypropylmethylcellulose (hereinafter to be sometimes indicated as HPMC), methylcellulose, carboxymethylcellulose sodium and the like, sodium polyacrylate, polyvinyl alcohol, sodium alginate, guar gum and the like] and the like.

Examples of the "basic inorganic salt" include basic inorganic salts of sodium, potassium, magnesium and/or calcium. Preferred are basic inorganic salts of magnesium and/or calcium. More preferred is a basic inorganic salt of magnesium. Examples of the basic inorganic salt of sodium include sodium carbonate, sodium hydrogen carbonate, disodium hydrogen phosphate and the like. Examples of the basic inorganic salt of potassium include potassium carbonate, potassium hydrogen carbonate and the like. Examples of the basic inorganic salt of magnesium include heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16}CO_3 \cdot 4H_2O$] and alumina magnesium hydroxide, preferably, heavy magnesium carbonate, magnesium carbonate, magnesium oxide, magnesium hydroxide and the like. Examples of the basic inorganic salt of calcium include precipitated calcium carbonate, calcium hydroxide and the like.

Examples of the "solvent" include water for injection, alcohol, propylene glycol, macrogol, sesame oil, corn oil, olive oil and the like.

Examples of the "solubilizing agent" include polyethylene glycol, propylene glycol, benzyl benzoate, ethanol, trisaminomethane, cholesterol, triethanolamine, sodium carbonate, sodium citrate and the like.

Examples of the "suspending agent" include surfactants such as stearyltriethanolamine, sodium lauryl sulfate, lauryl aminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like, and the like.

Examples of the "isotonicity agent" include glucose, D-sorbitol, sodium chloride, glycerol, D-mannitol and the like.

Examples of the "buffering agent" include buffers such as phosphate, acetate, carbonate, citrate and the like, and the like.

Examples of the "soothing agent" include benzyl alcohol and the like.

Examples of the "preservative" include paraoxybenzoates, chlorobutanol, benzyl alcohol, phenethyl alcohol, dehydroacetic acid, sorbic acid and the like.

Examples of the "antioxidant" include sulfite, ascorbic acid, α-tocopherol and the like.

Examples of the "colorant" include food colors such as Food Color Yellow No. 5, Food Color Red No. 2, Food Color Blue No. 2 and the like; food lake colors, ferric oxide red, yellow ferric oxide and the like.

Examples of the "sweetening agent" include saccharin sodium, dipotassium glycyrrhizinate, aspartame, stevia, thaumatin and the like.

Examples of the "foaming agent" include sodium bicarbonate and the like.

As the "flavor", any of synthetic substance and naturally-occurring substance may be used. Examples thereof include flavors such as lemon, lime, orange, menthol, strawberry and the like.

The pharmaceutical composition of the present invention does not have to contain a souring agent.

The pharmaceutical composition of the present invention can be formulated into a preparation for oral administration (film-coated tablet) by, for example, adding a pharmacologically acceptable carrier such as binder, disintegrant, lubricant and the like as necessary to a granulated powder containing the above-mentioned first to third components, tableting the obtained mixture by a method known per se (preparation of core tablet (core)) and, where necessary, coating the tablet by a method known per se for masking of taste, enteric coating or sustained release. When the pharmaceutical composition of the present invention is, for example, formulated into an orally disintegrating tablet, the above-mentioned composition containing the first to third components can be produced by a method known per se. Moreover, such tablet can be produced by a method including coating a core containing crystalline cellulose and lactose with the pharmaceutical composition of the present invention, forming an enteric coating layer by a method known per se to give fine granules, mixing the obtained fine granules and an additive and molding the mixture.

A film-coated tablet is more preferable.

In addition, a core material containing an acidic compound and a layer containing a pharmaceutically active ingredient do not need to be separated by a separating layer.

Examples of the above-mentioned "enteric coating layer" include a layer comprised of a mixture of one or more kinds from aqueous enteric polymer base such as cellulose acetate phthalate (CAP), hydroxypropylmethylcellulose phthalate, hydroxymethylcellulose acetate succinate, methacrylic acid copolymer [for example, Eudragit L30D-55 (trade name; manufactured by Roehm), Kollicoat MAE30DP (trade name; manufactured by BASF), Polyquid PA30 (trade name; manufactured by Sanyo chemical industries, Ltd.) etc.], carboxymethylethylcellulose, shellac and the like; sustained-release base such as methacrylic acid copolymer [for example, Eudragit NE30D (trade name), Eudragit RL30D (trade name), Eudragit RS30D (trade name) etc.] and the like; water-soluble polymer; plasticizer such as triethyl citrate, polyethylene glycol, acetylated monoglyceride, triacetine, castor oil etc. and the like.

Examples of the above-mentioned "additive" include water-soluble sugar alcohol (e.g., sorbitol, mannitol and maltitol, reduced starch saccharides, xylitol, reduced paratinose, erythritol etc.), crystalline cellulose (e.g., Ceolus KG 801, Avicel PH 101, Avicel PH 102, Avicel PH 301, Avicel PH 302, Avicel RC-591 (crystalline cellulose, carmellose sodium) etc.), low-substituted hydroxypropylcellulose (e.g., LH-22, LH-32, LH-23, LH-33 (Shin-Etsu Chemical Co., Ltd.) and a mixture thereof etc.) and the like. Furthermore, binder, foaming agent, sweetening agent, flavor, lubricant, colorant, stabilizer, excipient, disintegrant and the like can also be used.

The pharmaceutical composition of the present invention is superior in the preservation stability. Particularly, when the pharmaceutical composition of the present invention contains a compound represented by the above-mentioned formula (A2) or (A3) as a pharmaceutically active ingredient, such pharmaceutical composition is useful for the treatment or prophylaxis of peptic ulcer (e.g., gastric ulcer, ulcer due to postoperative stress, duodenal ulcer, anastomotic ulcer, ulcer caused by non-steroidal anti-inflammatory agent etc.); Zollinger-Ellison syndrome; gastritis; erosive esophagitis; reflux esophagitis such as erosive reflux esophagitis and the like; symptomatic gastroesophageal reflux disease (Symptomatic GERD) such as nonerosive esophageal reflux, esophageal reflux unaccompanied by esophagitis and the like; functional dyspepsia; Barrett esophagus; gastric cancer (including gastric cancer associated with promoted production of interleukin-1β due to gene polymorphism of interleukin-1); stomach MALT lymphoma; hyperacidity; upper gastrointestinal hemorrhage caused by peptic ulcer, acute stress ulcer, hemorrhagic gastritis, invasive stress (e.g., stress caused by major surgery requiring post-operative intensive management, or cerebrovascular disorder, head trauma, multiple organ failure or extensive burn requiring intensive treatment) and the like; airway disorders; asthma; and the like in mammals (e.g., human, monkey, sheep, bovine, horse, dog, cat, rabbit, rat, mouse etc.), pre-anesthetic administration, eradication or assistant to eradication of *Helicobacter pylori* and the like.

While the dose of the pharmaceutical composition of the present invention varies depending on the subject of administration, administration route, disease and the like, for oral administration to an adult (60 kg) as, for example, an antiulcerogenic drug, it is preferably administered in an amount of about 0.5-about 1500 mg/day, preferably about 5-about 150 mg/day, as a pharmaceutically active ingredient. The pharmaceutical composition of the present invention may be administered once a day or in 2-3 portions a day.

The pharmaceutical composition of the present invention may be used in combination with other active ingredient as long as the activity of the nonpeptidic pharmaceutically active ingredient having a primary or secondary amino group is not impaired.

Examples of the "other active ingredient" include anti-*Helicobacter pylori* active substance, imidazole compound, bismuth salt, quinolone compound and the like.

Examples of the "anti-*Helicobacter pylori* active substance" include penicillin antibiotic (e.g., amoxicillin, benzyl penicillin, piperacillin, mecillinam, ampicillin, temocillin, bacampicillin, aspoxicillin, sultamicillin, lenampicillin, etc.), cephem antibiotic (e.g., cefixime, cefaclor, etc.), macrolide antibiotic (e.g., erythromycin, clarithromycin, roxithromycin, rokitamycin, flurithromycin, telithromycin, etc.), tetracycline antibiotic (e.g., tetracycline, minocycline, streptomycin etc.), aminoglycoside antibiotic (e.g., gentamicin, amikacin etc.), imipenem and the like. Of these, penicillin antibiotic, macrolide antibiotic and the like are preferable.

Examples of the "imidazole compound" include metronidazole, miconazole and the like.

Examples of the "bismuth salt" include bismuth acetate, bismuth citrate, bithmuth subsalicylate and the like.

Examples of the "quinolone compound" include ofloxacin, ciploxacin and the like.

Particularly, for *Helicobacter pylori* eradication, in the pharmaceutical composition of the present invention wherein the pharmaceutically active ingredient is a compound represented by the above-mentioned (A2), (A3) or (A4), a penicillin antibiotic (e.g., amoxicillin etc.) and an erythromycin antibiotic (e.g., clarithromycin etc.) are preferably used. For *Helicobacter pylori* eradication, while the pharmaceutical composition of the present invention has an anti-*H. pylori* action (bacteriostatic or eradication action) by itself, it can enhance an antibacterial action of other antibiotics by regulating its pH in the stomach and the like, thus acting as an aid for the eradication effect based on the action of the antibiotic to be used in combination.

In addition, the pharmaceutical composition of the present invention may be used in combination with a gastric motility enhancer, a drug acting on the lower esophageal sphincter (e.g., transient lower esophageal sphincter relaxation inhibitor, etc.), ClC-2 channel opener (intestinal juice secretion accelerating agent), histamine H2 receptor antagonist, antacid, sedative, stomachic or non-steroidal anti-inflammatory drug (NSAID).

Examples of the "gastric motility enhancer" include domperidone, metoclopramide, mosapride, itopride, tegaserod and the like.

Examples of the "drug acting on the lower esophageal sphincter" include GABA-B receptor agonists such as baclofen, an optically active form thereof and the like, and the like.

Examples of the "ClC-2 channel opener (intestinal juice secretion accelerating agent)" include lubiprostone and the like.

Examples of the "histamine H2 receptor antagonist" include cimetidine, ranitidine, famotidine, roxatidine, nizatidine, lafutidine and the like.

Examples of the "antacid" include sodium hydrogen carbonate, aluminum hydroxide and the like.

Examples of the "sedative" include diazepam, chlordiazepoxide and the like.

Examples of the "stomachic" include *Gentiana lutea, swertia japonica*, diastase and the like.

Examples of the "non-steroidal anti-inflammatory drug" include aspirin, indomethacin, ibuprofen, mefenamic acid, diclofenac, etodolac, piroxicam, celecoxib and the like.

The pharmaceutical composition of the present invention may also be used in combination with the following medicaments.

(i) proton pump inhibitor, e.g., omeprazole, esomeprazole, pantoprazole, rabeprazole, tenatoprazole, ilaprazole and lansoprazole;

(ii) oral antacid-combination agent, e.g., Maalox (registered trade mark), Aludrox (registered trade mark) and Gaviscon (registered trade mark);

(iii) mucous membrane protector, e.g., polaprezinc, ecabet sodium, rebamipide, teprenone, cetraxate, sucralfate, chlorophylline-copper and plaunotol;

(iv) anti-gastrin agent, e.g., anti-gastrin vaccine, itriglumide and Z-360;

(v) 5-HT$_3$ antagonist, e.g., dolasetron, palonosetron, alosetron, azasetron, ramosetron, mitrazapine, granisetron, tropisetron, E-3620, ondansetron and indisetron;

(vii) 5-HT4 agonist, e.g., tegaserod, mosapride, cinitapride and oxitriptane;

(vii) laxative, e.g., Trifyba (registered trade mark), Fybogel (registered trade mark), Konsyl (registered trade mark), Isogel (registered trade mark), Regulan (registered trade mark), Celevac (registered trade mark) and Normacol (registered trade mark);

(viii) GABA$_B$ agonist, e.g., baclofen and AZD-3355;

(ix) GABA$_B$ antagonist, e.g., GAS-360 and SGS-742;

(x) calcium channel blocker, e.g., aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonist, e.g., metoclopramide, domperidone and levosulpiride;

(xii) tachykinin (NK) antagonist, particularly, NK-3, NK-2 and NK-1 antagonist, e.g., nepadutant, saredutant, talnetant, (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6,13-dione (TAK-637), 5-[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S);

(xiii) nitric oxide synthase inhibitor, e.g., GW-274150, tilarginine, P54, guanidioethyldisulfide and nitroflurbiprofen;

(xiv) vanilloid receptor 1 antagonist, e.g., AMG-517 and GW-705498;

(xv) ghrelin agonist, e.g., capromorelin and TZP-101;

(xvi) AchE release stimulant, e.g., Z-338 and KW-5092;

(xvii) therapeutic agent for insomnia (etizolam, zopiclone, triazolam, zolpidem, ramelteon, indiplon etc.), (xviii) potassium ion competitive acid secretion blocker (P-CAB), (xix) melatonin agonist, (xx) melatonin, and the like.

The above-mentioned medicaments (i)-(xx) may be used in combination by adding to the pharmaceutical composition of the present invention. Alternatively, the above-mentioned medicaments (i)-(xx) and the pharmaceutical composition of the present invention may be separately produced and simultaneously administered or administered in a staggered manner to the same subject.

Next, the second invention of the present invention is explained in detail by referring to a specific embodiment.

The solid preparation of the second invention of the present invention contains a pharmaceutically active ingredient, titanium oxide, a plasticizer and a chain organic acid, and is characteristically a solid preparation improved in the stability during light irradiation.

When a pharmaceutically active ingredient unstable to light irradiation is formulated into a preparation, titanium oxide ($TiO_2$) is generally used together with a film coating agent (also referred to as a coating agent) for shielding to ensure light-stability of the preparation. However, $TiO_2$ shows a shielding function due to its high refractive index, but also shows a strong oxidation action caused by hole generation during light irradiation. The cause is presumed to be that 1) titanium oxide in a coating agent develops a free radical due to UV light, 2) the drug and alcohols in the coating agent such as polyethylene glycol and the like are decomposed due to free radical, 3) a decomposed product of alcohols (e.g., polyethylene glycol and the like), for example, aldehydes such as formaldehyde, acetoaldehyde and the like, an acid such as formic acid and the like, and peroxide in the coating agent further cause decomposition of the drug. To improve the light-stability of the preparation, therefore, it is necessary to suppress the decomposed product due to its strong oxidation action while utilizing the light shielding effect of $TiO_2$. Conventionally, as a means to suppress an increase in the decomposed product, a method including forming an intermediate layer between a film coating and a core tablet and a method including removing PEG (plasticizer) from a film coating component have generally been employed. However, these methods may decrease the productivity during film coating, which may influence the final appearance of a film-coated tablet.

The present inventors have found an effect of suppressing a decomposed product during light irradiation by adding a chain organic acid to the solid preparation (either core or film), without decreasing the productivity during film coating.

The solid preparation of the present invention improved in the light stability is explained in the following.

[Pharmaceutically active ingredient (component I)]

The form of the pharmaceutically active ingredient to be used in the present invention may be any of solid, powder, crystal, oil, solution and the like, and its efficacy is not particularly limited. For example, one or more kinds of components selected from nutritional supplement, antipyretic analgesic antiphlogistic drug, psychotropic drug, antianxiety drug, antidepressant, hypnosedative, anticonvulsant, central nervous system neural active agent, brain metabolism improving agent, brain circulation improving agent, antiepilepsy agent, sympathetic nerve stimulant, digestive medicine, antacid, anti-ulcer agent, antitussive expectorant, antiemetic, respiratory stimulant, bronchodilator, antiallergic agent, dental and oral drug, antihistamine agent, cardiotonic agent, antiarrhythmic agent, diuretic, antihypertensive agent, vasoconstrictor, coronary vasodilator, peripheral vasodilator, lipid-lowering agent, cholagogue, antibiotic, chemotherapeutic agent, diabetes agent, osteoporosis agent, anti-rheumatic drug, skeleton muscle relaxants, hormone agent, narcotic alkaloid, sulfa drug, gout a therapeutic drug for, anticoagulant, anti-malignant tumor agent, therapeutic drug for Alzheimer's disease, potassium ion competitive acid secretion inhibitor and the like can be used.

Examples of the nutritional supplement include vitamins such as vitamin A, vitamin D, vitamin E (d-α-tocopherol acetate and the like), vitamin B1 (dibenzoylthiamine, fursultiamine hydrochloride and the like), vitamin B2 (riboflavin butyrate and the like), vitamin B6 (pyridoxine hydrochloride and the like), vitamin C (ascorbic acid, sodium L-ascorbate and the like), vitamin B12 (hydroxocobalamin acetate, cyanocobalamin and the like), mineral such as calcium, magnesium, iron and the like, protein, amino acid, oligosaccharide, crude drug and the like.

Examples of the antipyretic analgesic antiphlogistic drug include aspirin, acetaminophen, ethenzamide, ibuprofen, diphenhydramine hydrochloride, dl-chlorpheniramine maleate, dihydrocodeine phosphate, noscapine, methylephedrine hydrochloride, phenylpropanolamine hydrochloride, caffeine, anhydrous caffeine, serrapeptase, lysozyme chloride, tolfenamic acid, mefenamic acid, diclofenac sodium, flufenamic acid, salicylamide, aminopyrine, ketoprofen, indomethacin, bucolome, pentazocine and the like.

Examples of the psychotropic drug include chlorpromazine, reserpine and the like.

Examples of the antianxiety drug include alprazolam, chlordiazepoxide, diazepam and the like.

Examples of the antidepressant include imipramine, maprotiline hydrochloride, amphetamine and the like.

Examples of the hypnosedatives include estazolam, nitrazepam, diazepam, perlapine, phenobarbital sodium and the like.

Examples of the anticonvulsant include scopolamine hydrobromide, diphenhydramine hydrochloride, papaverine hydrochloride, meclizine hydrochloride, dimenhydrinate and the like.

Examples of the central nervous system neural active agent include citicoline and the like.

Examples of the brain metabolism improving agent include meclofenoxate hydrochloride and the like.

Examples of the brain circulation improving agent include vinpocetine and the like.

Examples of the antiepilepsy agent include phenyloin, carbamazepine and the like.

Examples of the sympathetic nerve stimulant include isoproterenol hydrochloride and the like.

Examples of the digestive medicine include stomachics and digestives such as diastase, saccharated pepsin, scopolia extract, cellulose AP3, lipase AP, cassia oil and the like, antiflatulent such as berberine chloride, resistant lactobacilli, bifidobacteria and the like, and the like.

Examples of the antacid include magnesium carbonate, sodium hydrogen carbonate, magnesium alumino metasilicate, synthetic hydrotalcite, precipitated calcium carbonate, magnesium oxide and the like.

Examples of the anti-ulcer agent include lansoprazole, omeprazole, rabeprazole, pantoprazole, ilaprazole, tenatoprazole, famotidine, cimetidine, ranitidine hydrochloride and the like.

Examples of the antitussive expectorant include cloperastine hydrochloride, dextromethorphan hydrobromide, theophylline, potassium guaiacolsulfonate, guaifenesin, codeine phosphate and the like.

Examples of the antiemetic include difenidol hydrochloride, metoclopramide and the like.

Examples of the respiratory stimulant include levallorphan tartrate and the like.

Examples of the bronchodilator include theophylline, salbutamol sulfate and the like.

Examples of the antiallergic agent include amlexanox, seratrodust and the like.

Examples of the dental and oral drug include oxytetracycline, triamcinolone acetonide, chlorhexidine hydrochloride, lidocain and the like.

Examples of the antihistamine agent include diphenhydramine hydrochloride, promethazine, isothipendyl hydrochloride, dl-chlorpheniramine maleate and the like.

Examples of the cardiotonic agent include caffeine, digoxin and the like.

Examples of the antiarrhythmic agent include procaineamide hydrochloride, propranolol hydrochloride, pindolol and the like.

Examples of the diuretic include thiazide such as isosorbide, furosemide, HCTZ and the like, and the like.

Examples of the antihypertensive agent include delapril hydrochloride, captopril, hexamethonium bromide, hydralazine hydrochloride, labetalol hydrochloride, manidipine hydrochloride, candesartancilexetil, methyldopa, losartan, valsartan, eprosartan, irbesartan, tasosartan, telmisartan and the like.

Examples of the vasoconstrictor include phenylephrine hydrochloride and the like.

Examples of the coronary vasodilator include carbochromene hydrochloride, molsidomine, verapamil hydrochloride and the like.

Examples of the peripheral vasodilator include cinnarizinee and the like.

Examples of the lipid-lowering agent include cerivastatin sodium, simvastatin, pravastatin sodium and the like.

Examples of the cholagogue include dehydrocholic acid, trepibutone and the like.

Examples of the antibiotic include cephem antibiotics such as cefalexin, cefaclor, amoxicillin, pivmecillinam hydrochloride, cefotiam hexetil hydrochloride, cefadroxil, cefixime, cefditoren pivoxil, cefteram pivoxil, cefpodoxime proxetil, cefotiam hydrochloride, cefozopran hydrochloride, cefmenoxime hydrochloride, cefsulodin sodium and the like, synthetic antibacterial agents such as ampicillin, ciclacillin, sulbenicillin sodium, naldixic acid, enoxacin and the like, monobactum antibiotics such as carumonam sodium and the like, penem and carbapenem antibiotics and the like.

Examples of the chemotherapeutic agent include sufamethizol, sufamethizol hydrochloride, thiazosulfone and the like.

Examples of the diabetes agent include tolbutamide, pioglitazone hydrochloride, voglibose, glibenclamide, troglitazone, rosiglitazone maleate, acarbose, miglitol, emiglitate and the like.

Examples of the osteoporosis agent include ipriflavone and the like.

Examples of the skeleton muscle relaxant include methocarbamol and the like.

Examples of the anti-rheumatic drug include methotrexate, bucillamine and the like.

Examples of the hormone agent include liothyronine sodium, dexamethasone sodium phosphate, prednisolone, oxendolone, leuprorelin acetate and the like.

Examples of the narcotic alkaloid include opium, morphine hydrochloride, ipecac, oxycodon hydrochloride, opium alkaloid hydrochloride, cocaine hydrochloride and the like.

Examples of the sulfa drug include sulfamin, sulfisomidine, sufamethizol and the like.

Examples of the therapeutic drug for gout include allopurinol, colchicine and the like.

Examples of the anticoagulant include dicoumarol and the like.

Examples of the anti-malignant tumor agent include 5-fluorouracil, uracil, mitomycin and the like.

Examples of the therapeutic drug for Alzheimer's disease include idebenone, vinpocetine and the like.

Examples of the potassium ion competitive acid secretion blocker (P-CAB) include a compound represented by the above-mentioned formula (A1), the formula (A2), the formula (A3) or the formula (A4) and the like.

Of the aforementioned pharmaceutically active ingredients, a pharmaceutically active ingredient that can particularly enjoy the effect of the invention is a pharmaceutically active ingredient unstable to light irradiation. For example, the present invention is particularly effective for a pharmaceutically active ingredient represented by the above-mentioned formula (A1), the formula (A2), the formula (A3) or the formula (A4), which belongs to the "pharmaceutically active ingredient unstable to light irradiation". That is, the present invention has a remarkable effect for improving the stability of a pharmaceutically active ingredient represented by the above-mentioned formula (A1), the formula (A2), the formula (A3) or the formula (A4) to light irradiation.

[Titanium Oxide (Component II)]

In the present invention, titanium oxide has a superior shielding effect against light. The particle size of titanium oxide to be used in the present invention is generally about 0.01-about 1.5 μm, preferably about 0.1-about 0.7 μm. When titanium oxide is added to a coating agent for film-coated tablets and the like, the content of titanium oxide is such an amount capable of achieving the object of shielding of the pharmaceutical preparation, which is preferably about 5-about 30 wt %, more preferably about 5-about 20 wt %, of the coating agent.

[Plasticizer (Component III)]

Examples of the "plasticizer" to be used in the present invention include plasticizers generally used in a pharmaceutical preparation. Specifically, for example, esters such as triethyl citrate, medium-chain triglyceride, diethyl phthalate, dibutyl phthalate, triacetine (triacetyl glycerol), butyl phthalyl butyl glycolate, glyceryl caprylate and the like; alcohols such as glycerol, propylene glycol, polyethylene glycol and the like, and the like. As the plasticizer, a compound of the chemical formula [$HOCH_2(CH_2OCH_2)_nCH_2OH$ (n=integer of 2-870)] is preferable, and polyethylene glycol (PEG) is particularly preferable. Examples of PEG actually used as the plasticizer include macrogol (manufactured by Sanyo chemical industries, Ltd.). While the average molecular weight of PEG is not particularly limited, it is preferably not less than 200, more preferably 200-20000, since a smaller average molecular weight increases hygroscopicity. When PEG is added to a coating agent for a film-coated tablet and the like, the content of PEG is preferably about 5-about 30 wt %, especially about 10-25 wt %, more preferably about 10-about 20 wt %, of the coating agent.

[Chain Organic Acid (Component IV)]

In the solid preparation of the present invention, titanium oxide is used for shielding. However, it is known that since titanium oxide has a strong oxidation action as mentioned above, when a coating agent containing a light shielding agent such as titanium oxide and the like and a plasticizer such as polyethylene glycol and the like is applied to a drug-containing tablet during formulation of a preparation of a drug unstable to light, the obtained film-coated tablet becomes inferior to the tablet before a coating treatment in the stability to light. The present invention effectively suppresses, without decreasing the productivity during film coating, generation of a decomposed product during light irradiation by adding an organic acid, particularly a chain organic acid, together with titanium oxide to, for example, a solid preparation such as a film coating agent and the like. Examples of the chain organic acid include adipic acid, oleic acid, succinic acid, acetic acid, tartaric acid, sorbic acid, fumaric acid, lactic acid, maleic acid, malonic acid, citric acid, malic acid and the like. These organic acids may be used alone, or two or more kinds thereof may be used simultaneously. The chain organic acid preferably has pH 6.0 or below when dissolved or dispersed in water. The chain organic acid is preferably fumaric acid, citric acid, succinic acid or tartaric acid, more preferably fumaric acid, succinic acid or tartaric acid.

The pH of a chain organic acid is measured under the following conditions. To be specific, the pH of an aqueous solution or dispersion obtained by dissolving or dispersing a measurement target in water at 1% w/v is measured at 25° C. with a commercially available pH meter.

The content (%) of the chain organic acid in the whole pharmaceutical composition of the present invention is preferably 0.1-20% (more preferably 0.1-19%), further preferably 1-10%, particularly preferably 2-10%. In another embodiment, it is 0.01-50%, preferably 0.05-19%, more preferably 0.1-10%.

When producing the pharmaceutical composition of the present invention, the "chain organic acid" may be added as a powder in a granulation step or a mixing step. In addition, a chain organic acid can be sprayed by dissolving or dispersing in a binder solution in the granulation step or in a film coating solution in a film coating step.

The solid preparation containing the pharmaceutically active ingredient of the present invention has low toxicity, and can be safely administered orally or parenterally (e.g., topical, rectal, intravenous administration etc.) as it is or in the form of a pharmaceutical composition containing a pharmacologically acceptable carrier according to a method known per se, for example, as preparations such as tablet (core tablet, sugar-coated tablet, film-coated tablet etc.), powder, granule, capsule (including soft capsule), orally disintegrating tablet, suppository, sustained-release preparation and the like. The pharmaceutical composition of the present invention is preferably administered as an oral preparation such as tablet, granule, capsule and the like. Of these, tablet and capsule are preferable, and a sugar-coated tablet and a film-coated tablet are especially preferable.

As the pharmacologically acceptable carrier that can be used for the production of the pharmaceutical composition of the present invention, those similar to the examples recited for the first invention can be mentioned.

The pharmaceutical composition of the present invention does not have to contain a souring agent.

Now, as one embodiment of the present invention, an example wherein a solid preparation containing a pharmaceutically active ingredient, titanium oxide, a plasticizer and a chain organic acid, as explained above, is applied to a film-coated tablet is explained in the following. The film-coated tablet is obtained by coating a core tablet (core) containing a pharmaceutically active ingredient with a film coating layer comprising the following film coating polymer. Generally, a pharmaceutically active ingredient is contained in a core, but titanium oxide, a chain organic acid and a plasticizer may be contained in either or both of a core or(and) a film coating layer. Particularly, titanium oxide and a plasticizer are preferably contained in a film coating layer. In addition, a core material containing a chain organic acid and a layer containing an active ingredient do not need to be separated by a separating layer.

A film coating solution is sprayed on a solid preparation (preferably tablet, more preferably ellipse or round tablet), and dried as necessary. The "film coating solution" is prepared by, for example, dissolving or suspending a film coating polymer in a solvent. The film coating solution may further contain, for example, a colorant (preferably, diiron trioxide and yellow ferric oxide), a light shielding agent (preferably, titanium oxide) and the like. Examples of the "film coating polymer" include hydroxypropylmethylcellulose, ethylcellulose, hydroxymethylcellulose, hydroxypropylcellulose, hydroxypropylmethylcellulose acetate succinate, acrylic resin (methacrylic acid-acrylic acid copolymer, aminoalkylmethacrylate copolymer etc.), shellac, polyvinyl acetatephthalate, gum arabic, cellulose acetate phthalate, hydroxypropylmethylcellulose phthalate, carboxymethylethylcellulose and the like. Examples of the "solvent" include water, alcohols (e.g., ethanol, isopropyl alcohol, n-propyl alcohol, methanol and the like), acetone, ethyl acetate, dichloromethane, chloroform, hexane, toluene, heptane and the like. The amount of the "film coating polymer" to be used can be selected according to the kind of the solid preparation and, when the solid preparation is a tablet, it is, for example, about 0.5-10 wt % of a tablet. The spraying temperature is generally 25-80° C., the spraying time is generally 5 min-24 hr, and the drying conditions are generally 30-80° C. for about 1 min-24 hr. The film coating layer of the present invention can be formed at a ratio of generally 1-10 parts by weight, preferably 2-6 parts by weight, per 100 parts by weight of the solid preparation (preferably tablet, more preferably ellipse or round tablet) of the present invention.

The pharmaceutical composition of the present invention can be formulated into a preparation for oral administration (film-coated tablet) by, for example, adding, where necessary, an excipient to the above-mentioned component I and component IV to give a granulated powder, adding, where necessary, a binder, a disintegrant, a lubricant and the like thereto, tableting the obtained mixture by a method known per se and, where necessary, coating the tablet by a method known per se for masking of taste, enteric coating or sustained release.

The core tablet of the pharmaceutical composition of the present invention can be obtained by adding an excipient and the above-mentioned component IV (chain organic acid) to the above-mentioned component I (pharmaceutically active ingredient), adding, where necessary, a binder, sieving the obtained granulated powder, adding, where necessary, a disintegrant and, where necessary, a lubricant, mixing the mixture, and punching the obtained mixed powder. The obtained core tablet can be formulated into a film-coated tablet of the pharmaceutical composition of the present invention by coating the core tablet by a method known per se.

A binder can be added by spraying an aqueous solution thereof and the like.

The coating by a method known per se includes, for example, separately preparing a coating solution using a disperser or a propeller stirring machine, and the like, and spraying and coating the solution on tablets charged in a film coating machine.

Examples of the above-mentioned "excipient", "binder", "disintegrant" and "lubricant" respectively include those similar to the examples recited for the above-mentioned first invention.

The pharmaceutical composition of the present invention is superior in the stability during light irradiation. The pharmaceutical composition of the present invention can be used in the same manner as described in the above-mentioned first invention.

The pharmaceutical composition of the present invention may have the characteristics of both the first invention and the second invention.

EXAMPLES

The present invention is explained in more detail in the following by referring to Comparative Examples, Examples and Experimental Examples, which are not to be construed as limitative. In the formulations described as Examples, Pharmacopoeia compatible products and Japanese Pharmaceutical Excipients compatible products were used as the components other than the active ingredient (additives). In the following Examples and Comparative Examples, the Japanese Pharmacopoeia 15th Edition or Japanese Pharmaceutical Excipients 2003 compatible products were used as the preparation additives (e.g., lactose, D-mannitol, hydroxypropylcellulose, crospovidone, magnesium stearate, crystalline cellulose).

Unless otherwise specified, % in the following means wt %.

Firstly, the results of the stability evaluation of the pharmaceutical composition of the first invention of the present invention, containing a nonpeptidic pharmaceutically active ingredient having a primary or secondary amino group, an excipient and an acidic compound are explained by Examples 1-44 and Comparative Examples 1-6.

Comparative Example 1

Sample 1

A plain tablet (core tablet) containing 1-[5-(2-fluorophenyl)-1-(pyridin-3-ylsulfonyl)-1H-pyrrol-3-yl]-N-methylmethanamine fumarate (hereinafter to be referred to as compound A) was produced as follows at the composition ratio shown in Table 2-1.

That is, compound A (24.491 g), mannitol (4350.0 g) and crystalline cellulose (540.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.0 g) was passed through a powermill (P-3, manufactured by Showa Kagaku Kikai Kosakusho) to give a sized powder. The sized powder (4230.0 g), croscarmellose sodium (225.0 g) and magnesium stearate (45.007 g) were placed in a tumbler mixer (TM-15S, manufactured by Showa Kagaku Kikai Kosakusho), and mixed to give a mixed powder. The mixed powder was tableted by a rotary tableting machine (COLLECT 12HUK, manufactured by Kikusui Seisakusho, Ltd.) using a 9 mmφ punch to give plain tablets (core tablets, 300 mg per tablet).

TABLE 2-1

Composition of plain tablet (core tablet)
containing compound A (sample 1)

| composition | amount (mg) |
| --- | --- |
| 1) compound A* | 1.336 |
| 2) mannitol | 241.664 |
| 3) crystalline cellulose | 30 |
| 4) hydroxypropylcellulose | 9 |
| 5) croscarmellose sodium | 15 |
| 6) magnesium stearate | 3 |
| total | 300.0 |

*Where necessary, the content was amended using mannitol as an adjustment component.

Comparative Example 2

Sample 2

The plain tablet (core tablet) (sample 1, 3300.0 g) obtained in Comparative Example 1 was placed in a film coating machine (DRC-500, manufactured by POWREX CORPORATION), and film-coated tablets (about 312 mg per tablet) were obtained while spraying a film coating solution (1372.0 g) having the composition ratio shown in Table 2-2. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 6 months.

TABLE 2-2

Composition of aqueous film coating solution

| composition | amount (mg) |
| --- | --- |
| 1) hypromellose | 10.8 |
| 2) titanium oxide | 1 |
| 3) diiron trioxide | 0.2 |
| 4) purified water | 108 |
| total | 120.0 |

Example 1

Sample 3

A plain tablet (core tablet) containing compound A was produced as follows at the composition ratios shown in Table 3.

That is, compound A (4.01 g), mannitol (722.6 g) and crystalline cellulose (90.6 g) were placed in a fluidized bed dryer granulator (LAB-1, manufactured by POWREX CORPORATION), and the mixture was preheated and mixed. The mixture was granulated while spraying an aqueous solution (452.4 g) of hydroxypropylcellulose (27.0 g) and fumaric acid (2.4 g) to give a granulated powder. The obtained granulated powder was passed through a 16M (1000 μm) sieve to give a sized powder. To the sized powder (564.3 g) were added croscarmellose sodium (30.00 g) and magnesium stearate (6.000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet). A part of the obtained plain tablet (core tablet) was used for preservation measurement. That is, the plain tablet (core tablet) was placed in a glass bottle, tightly sealed and preserved at 60° C. for 2 weeks.

TABLE 3

Composition of plain tablet (core tablet)
containing compound A (sample 3)

| composition | amount (mg) |
| --- | --- |
| 1) compound A | 1.336 |
| 2) mannitol | 240.864 |
| 3) crystalline cellulose | 30 |
| 4) hydroxypropylcellulose | 9 |
| 5) fumaric acid | 0.8 |
| 6) croscarmellose sodium | 15 |
| 7) magnesium stearate | 3 |
| total | 300.0 |

Example 2

Sample 4

A plain tablet (core tablet) containing compound A was produced as follows at the composition ratios shown in Table 4.

That is, compound A (4.01 g), mannitol (635.2 g), crystalline cellulose (90.0 g) and fumaric acid (90.1 g) were placed in a fluidized bed dryer granulator (LAB-1, manufactured by POWREX CORPORATION), and the mixture was preheated and mixed. The mixture was granulated while spraying an aqueous solution (450.0 g) of hydroxypropylcellulose (27.0 g) to give a granulated powder. The obtained granulated powder was passed through a 16M (1000 μm) sieve to give a sized powder. To the sized powder (564.2 g) were added croscarmellose sodium (30.00 g) and magnesium stearate (6.000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet). A part of the obtained plain tablet (core tablet) was used for preservation measurement. That is, the plain tablet (core tablet) was placed in a glass bottle, tightly sealed and preserved at 60° C. for 2 weeks.

TABLE 4

Composition of plain tablet (core tablet)
containing compound A (sample 4)

| composition | amount (mg) |
| --- | --- |
| 1) compound A | 1.336 |
| 2) mannitol | 211.664 |
| 3) crystalline cellulose | 30 |
| 4) hydroxypropylcellulose | 9 |
| 5) fumaric acid | 30 |
| 6) croscarmellose sodium | 15 |
| 7) magnesium stearate | 3 |
| total | 300.0 |

Example 3

Sample 5

A plain tablet (core tablet) containing compound A was produced as follows at the composition ratios shown in Table 5.

That is, compound A (4.01 g), mannitol (635.0 g), crystalline cellulose (90.0 g) and fumaric acid (87.7 g) were placed in a fluidized bed dryer granulator (LAB-1, manufactured by POWREX CORPORATION), and the mixture was preheated and mixed. The mixture was granulated while spraying an aqueous solution (452.4 g) of hydroxypropylcellulose (27.0 g) and fumaric acid (2.4 g) to give a granulated powder. The obtained granulated powder was passed through a 16M (1000 μm) sieve to give a sized powder. To the sized powder (564.1 g) were added croscarmellose sodium (30.20 g) and magnesium stearate (6.000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet). The plain tablet (core tablet) was placed in a glass bottle, tightly sealed and preserved at 60° C. for 2 weeks.

TABLE 5

Composition of plain tablet (core tablet) containing compound A (sample 5)

| composition | amount (mg) |
| --- | --- |
| 1) compound A | 1.336 |
| 2) mannitol | 211.664 |
| 3) crystalline cellulose | 30 |
| 4) hydroxypropylcellulose | 9 |
| 5) fumaric acid | 30 |
| 6) croscarmellose sodium | 15 |
| 7) magnesium stearate | 3 |
| total | 300.0 |

Example 4

Sample 6

A plain tablet (core tablet) containing compound A was produced as follows at the composition ratios shown in Table 6.

That is, compound A (2.6719 g), mannitol (481.8 g), crystalline cellulose (60.0 g) and fumaric acid (1.61 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (507.8 g) were added croscarmellose sodium (27.00 g) and magnesium stearate (5.4000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet).

TABLE 6

Composition of plain tablet (core tablet) containing compound A (sample 6)

| composition | amount (mg) |
| --- | --- |
| 1) compound A | 1.336 |
| 2) mannitol | 240.864 |
| 3) crystalline cellulose | 30 |
| 4) hydroxypropylcellulose | 9 |
| 5) fumaric acid | 0.8 |
| 6) croscarmellose sodium | 15 |
| 7) magnesium stearate | 3 |
| total | 300.0 |

Example 5

Sample 7

A plain tablet (core tablet) containing compound A was produced as follows at the composition ratios shown in Table 7.

That is, compound A (2.6724 g), mannitol (480.3 g), crystalline cellulose (60.0 g) and fumaric acid (3.01 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (507.9 g) were added croscarmellose sodium (27.00 g) and magnesium stearate (5.4000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet).

TABLE 7

Composition of plain tablet (core tablet) containing compound A (sample 7)

| composition | amount (mg) |
| --- | --- |
| 1) compound A | 1.336 |
| 2) mannitol | 240.164 |
| 3) crystalline cellulose | 30 |
| 4) hydroxypropylcellulose | 9 |
| 5) fumaric acid | 1.5 |
| 6) croscarmellose sodium | 15 |
| 7) magnesium stearate | 3 |
| total | 300.0 |

Example 6

Sample 8

A plain tablet (core tablet) containing compound A was produced as follows at the composition ratios shown in Table 8.

That is, compound A (2.6721 g), mannitol (477.3 g), crystalline cellulose (60.0 g) and fumaric acid (6.01 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (507.7 g) were added croscarmellose sodium (27.00 g) and magnesium stearate (5.4000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet).

TABLE 8

Composition of plain tablet (core tablet) containing compound A (sample 8)

| composition | amount (mg) |
|---|---|
| 1) compound A | 1.336 |
| 2) mannitol | 238.664 |
| 3) crystalline cellulose | 30 |
| 4) hydroxypropylcellulose | 9 |
| 5) fumaric acid | 3 |
| 6) croscarmellose sodium | 15 |
| 7) magnesium stearate | 3 |
| total | 300.0 |

Example 7

Sample 9

A plain tablet (core tablet) containing compound A was produced as follows at the composition ratios shown in Table 9.

That is, compound A (2.6715 g), mannitol (469.3 g), crystalline cellulose (60.0 g) and fumaric acid (14.00 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (507.5 g) were added croscarmellose sodium (27.00 g) and magnesium stearate (5.4000 g) and the mixture was mixed in a bag to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet).

TABLE 9

Composition of plain tablet (core tablet) containing compound A (sample 9)

| composition | amount (mg) |
|---|---|
| 1) compound A | 1.336 |
| 2) mannitol | 234.664 |
| 3) crystalline cellulose | 30 |
| 4) hydroxypropylcellulose | 9 |
| 5) fumaric acid | 7 |
| 6) croscarmellose sodium | 15 |
| 7) magnesium stearate | 3 |
| total | 300.0 |

Example 8

Sample 10

A plain tablet (core tablet) containing compound A was produced as follows at the composition ratios shown in Table 10.

That is, compound A (20.04 g), mannitol (451.0 g), crystalline cellulose (60.0 g) and fumaric acid (15.0 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (526.4 g) were added croscarmellose sodium (28.00 g) and magnesium stearate (5.60 g) and the mixture was mixed in a bag to give a mixed powder. The mixed powder was tableted by a rotary tableting machine (COLLECT 19K, manufactured by Kikusui Seisakusho, Ltd.) using a 8 mmϕ punch to give plain tablets (core tablets, 200 mg per tablet).

TABLE 10

Composition of plain tablet (core tablet) containing compound A (sample 10)

| composition | amount (mg) |
|---|---|
| 1) compound A | 6.68 |
| 2) mannitol | 150.32 |
| 3) crystalline cellulose | 20 |
| 4) hydroxypropylcellulose | 6 |
| 5) fumaric acid | 5 |
| 6) croscarmellose sodium | 10 |
| 7) magnesium stearate | 2 |
| total | 200.0 |

Example 9

Sample 11

A plain tablet (core tablet) containing compound A was produced as follows at the composition ratios shown in Table 11.

That is, compound A (80.16 g), mannitol (390.9 g), crystalline cellulose (60.0 g) and fumaric acid (15.0 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (526.4 g) were added croscarmellose sodium (28.00 g) and magnesium stearate (5.60 g) and the mixture was mixed in a bag to give a mixed powder. The mixed powder was tableted by a rotary tableting machine (COLLECT 19K, manufactured by Kikusui Seisakusho, Ltd.) using a 8 mmϕ punch to give plain tablets (core tablets, 200 mg per tablet).

TABLE 11

Composition of plain tablet (core tablet) containing compound A (sample 11)

| composition | amount (mg) |
|---|---|
| 1) compound A | 26.72 |
| 2) mannitol | 130.28 |
| 3) crystalline cellulose | 20 |
| 4) hydroxypropylcellulose | 6 |
| 5) fumaric acid | 5 |
| 6) croscarmellose sodium | 10 |
| 7) magnesium stearate | 2 |
| total | 200.0 |

Example 10

Sample 12

A plain tablet (core tablet) containing compound A was produced as follows at the composition ratios shown in Table 12.

That is, compound A (160.32 g), mannitol (310.7 g), crystalline cellulose (60.6 g) and fumaric acid (15.0 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (526.4 g) were added croscarmellose sodium (28.00 g) and magnesium stearate (5.60 g) and the mixture was mixed in a bag to give a mixed powder. The mixed powder was tableted by a rotary tableting machine (COLLECT 19K, manufactured by Kikusui Seisakusho, Ltd.) using a 8 mmφ punch to give plain tablets (core tablets, 200 mg per tablet).

TABLE 12

Composition of plain tablet (core tablet) containing compound A (sample 12)

| composition | amount (mg) |
| --- | --- |
| 1) compound A | 53.44 |
| 2) mannitol | 103.56 |
| 3) crystalline cellulose | 20 |
| 4) hydroxypropylcellulose | 6 |
| 5) fumaric acid | 5 |
| 6) croscarmellose sodium | 10 |
| 7) magnesium stearate | 2 |
| total | 200.0 |

Example 11

Sample 13

A plain tablet (core tablet) containing compound A was produced as follows at the composition ratios shown in Table 13.

That is, compound A (160.32 g), mannitol (265.7 g), crystalline cellulose (60.0 g) and fumaric acid (60.0 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. To the sized powder (526.4 g) were added croscarmellose sodium (28.00 g) and magnesium stearate (5.60 g) and the mixture was mixed in a bag to give a mixed powder. The mixed powder was tableted by a rotary tableting machine (COLLECT 19K, manufactured by Kikusui Seisakusho, Ltd.) using a 8 mmφ punch to give plain tablets (core tablets, 200 mg per tablet).

TABLE 13

Composition of plain tablet (core tablet) containing compound A (sample 13)

| composition | amount (mg) |
| --- | --- |
| 1) compound A | 53.44 |
| 2) mannitol | 88.56 |
| 3) crystalline cellulose | 20 |
| 4) hydroxypropylcellulose | 6 |
| 5) fumaric acid | 20 |
| 6) croscarmellose sodium | 10 |
| 7) magnesium stearate | 2 |
| total | 200.0 |

Example 12

Sample 14

A plain tablet (core tablet) containing compound A was produced as follows at the composition ratios shown in Table 14.

That is, compound A (80.890 g), mannitol (4065.0 g), crystalline cellulose (528.0 g) and fumaric acid (132.0 g) were placed in a fluidized bed dryer granulator (FD-5S, manufactured by POWREX CORPORATION), and the mixture was preheated and mixed. The mixture was granulated while spraying an aqueous solution (2640.0 g) of hydroxypropylcellulose (158.4 g) to give a granulated powder. The obtained granulated powder (4550.0 g) was passed through a powermill (P-3, manufactured by Showa Kagaku Kikai Kosakusho) to give a sized powder. The sized powder (4239.0 g), croscarmellose sodium (225.5 g) and magnesium stearate (45.10 g) were placed in a tumbler mixer (TM-15S, manufactured by Showa Kagaku Kikai Kosakusho), and mixed therein to give a mixed powder. The mixed powder was tableted by a rotary tableting machine (COLLECT 12HUK, manufactured by Kikusui Seisakusho, Ltd.) using a 8 mmφ punch to give plain tablets (core tablets, 220 mg per tablet).

TABLE 14

Composition of plain tablet (core tablet) containing compound A (sample 14)

| composition | amount (mg) |
| --- | --- |
| 1) compound A* | 3.34 |
| 2) mannitol | 169.36 |
| 3) crystalline cellulose | 22 |
| 4) hydroxypropylcellulose | 6.6 |
| 5) fumaric acid | 5.5 |
| 6) croscarmellose sodium | 11 |
| 7) magnesium stearate | 2.2 |
| total | 220.0 |

*Where necessary, the content was amended using mannitol as an adjustment component.

Example 13

Sample 15

A plain tablet (core tablet) containing compound A was produced as follows at the composition ratios shown in Table 15.

That is, compound A (161.8 g), mannitol (3984.0 g), crystalline cellulose (528.0 g) and fumaric acid (132.0 g) were placed in a fluidized bed dryer granulator (FD-5S, manufactured by POWREX CORPORATION), and the mixture was preheated and mixed. The mixture was granulated while spraying an aqueous solution (2640.0 g) of hydroxypropylcellulose (158.4 g) to give a granulated powder. The obtained granulated powder (4550.0 g) was passed through a power-mill (P-3, manufactured by Showa Kagaku Kikai Kosakusho) to give a sized powder. The sized powder (4239.0 g), croscarmellose sodium (225.5 g) and magnesium stearate (45.1 g) were placed in a tumbler mixer (TM-15S, manufactured by Showa Kagaku Kikai Kosakusho), and mixed therein to give a mixed powder. The mixed powder was tableted by a rotary tableting machine (COLLECT 12HUK, manufactured by Kikusui Seisakusho, Ltd.) using a 8 mmφ punch to give plain tablets (core tablets, 220 mg per tablet).

TABLE 15

Composition of plain tablet (core tablet) containing compound A (sample 15)

| composition | amount (mg) |
|---|---|
| 1) compound A* | 6.68 |
| 2) mannitol | 166.02 |
| 3) crystalline cellulose | 22 |
| 4) hydroxypropylcellulose | 6.6 |
| 5) fumaric acid | 5.5 |
| 6) croscarmellose sodium | 11 |
| 7) magnesium stearate | 2.2 |
| total | 220.0 |

*Where necessary, the content was amended using mannitol as an adjustment component.

Example 14

Sample 16

A plain tablet (core tablet) containing compound A was produced as follows at the composition ratios shown in Table 16.

That is, compound A (323.5 g), mannitol (3824.0 g), crystalline cellulose (528.0 g) and fumaric acid (132.0 g) were placed in a fluidized bed dryer granulator (FD-5S, manufactured by POWREX CORPORATION), and the mixture was preheated and mixed. The mixture was granulated while spraying an aqueous solution (2640.0 g) of hydroxypropylcellulose (158.4 g) to give a granulated powder. The obtained granulated powder (4550.0 g) was passed through a power-mill (P-3, manufactured by Showa Kagaku Kikai Kosakusho) to give a sized powder. The sized powder (4239.0 g), croscarmellose sodium (225.5 g) and magnesium stearate (45.1 g) were placed in a tumbler mixer (TM-15S, manufactured by Showa Kagaku Kikai Kosakusho), and mixed therein to give a mixed powder. The mixed powder was tableted by a rotary tableting machine (COLLECT 12HUK, manufactured by Kikusui Seisakusho, Ltd.) using a 8 mmφ punch to give plain tablets (core tablets, 220 mg per tablet).

TABLE 16

Composition of plain tablet (core tablet) containing compound A (sample 16)

| composition | amount (mg) |
|---|---|
| 1) compound A* | 13.36 |
| 2) mannitol | 159.34 |
| 3) crystalline cellulose | 22 |
| 4) hydroxypropylcellulose | 6.6 |
| 5) fumaric acid | 5.5 |

TABLE 16-continued

Composition of plain tablet (core tablet) containing compound A (sample 16)

| composition | amount (mg) |
|---|---|
| 6) croscarmellose sodium | 11 |
| 7) magnesium stearate | 2.2 |
| total | 220.0 |

*Where necessary, the content was amended using mannitol as an adjustment component.

Example 15

Sample 17

A plain tablet (core tablet) containing compound A was produced as follows at the composition ratios shown in Table 17.

That is, compound A (647.1 g), mannitol (3504.0 g), crystalline cellulose (528.0 g) and fumaric acid (132.0 g) were placed in a fluidized bed dryer granulator (FD-5S, manufactured by POWREX CORPORATION), and the mixture was preheated and mixed. The mixture was granulated while spraying an aqueous solution (2640.0 g) of hydroxypropylcellulose (158.4 g) to give a granulated powder. The obtained granulated powder (4550.0 g) was passed through a power-mill (P-3, manufactured by Showa Kagaku Kikai Kosakusho) to give a sized powder. The sized powder (4239.0 g), croscarmellose sodium (225.5 g) and magnesium stearate (45.1 g) were placed in a tumbler mixer (TM-15S, manufactured by Showa Kagaku Kikai Kosakusho), and mixed therein to give a mixed powder. The mixed powder was tableted by a rotary tableting machine (COLLECT 12HUK, manufactured by Kikusui Seisakusho, Ltd.) using a 8 mmφ punch to give plain tablets (core tablets, 220 mg per tablet).

TABLE 17

Composition of plain tablet (core tablet) containing compound A (sample 17)

| composition | amount (mg) |
|---|---|
| 1) compound A* | 26.72 |
| 2) mannitol | 145.98 |
| 3) crystalline cellulose | 22 |
| 4) hydroxypropylcellulose | 6.6 |
| 5) fumaric acid | 5.5 |
| 6) croscarmellose sodium | 11 |
| 7) magnesium stearate | 2.2 |
| total | 220.0 |

*Where necessary, the content was amended using mannitol as an adjustment component.

Example 16

Sample 18

The plain tablet (core tablet) (sample 3, 299.95 g) obtained in Example 1 was placed in a film coating machine (HCT-MINI type, manufactured by Freund Corporation), and film-coated tablets (about 312 mg per tablet) were obtained while spraying a film coating solution (136.9 g) having the composition ratio shown in Table 18. The obtained film-coated tablet was placed in a glass bottle, tightly sealed and preserved at 60° C. for 2 weeks, and at 40° C., 75% RH for 2 or 6 months.

The film-coated tablet was placed in a glass bottle, and preserved in an open bottle at 40° C., 75% RH for 2 or 6 months.

TABLE 18

| Composition of aqueous film coating solution | |
|---|---|
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 17

Sample 19

The plain tablet (core tablet) (sample 4, 250.0 g) obtained in Example 2 was placed in a film coating machine (HCT-MINI type, manufactured by Freund Corporation), and film-coated tablets (about 312 mg per tablet) were obtained while spraying a film coating solution (103.1 g) having the composition ratio shown in Table 19. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 2 or 6 months.

TABLE 19

| Composition of aqueous film coating solution | |
|---|---|
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 18

Sample 20

The plain tablets (core tablets) obtained in Example 3 (sample 5, 300.0 g) were placed in a film coating machine (HCT-MINI type, manufactured by Freund Corporation), and film-coated tablets (about 312 mg per tablet) were obtained while spraying a film coating solution (126.6 g) having the composition ratio shown in Table 20. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 2 or 6 months.

TABLE 20

| Composition of aqueous film coating solution | |
|---|---|
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 19

Sample 21

The plain tablets (core tablets) obtained in Example 4 (sample 6, 300.0 g) were placed in a film coating machine (HCT-MINI type, manufactured by Freund Corporation), and film-coated tablets (about 312 mg per tablet) were obtained while spraying a film coating solution (145.0 g) having the composition ratio shown in Table 21. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 2 or 6 months.

TABLE 21

| Composition of aqueous film coating solution | |
|---|---|
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 20

Sample 22

The plain tablets (core tablets) obtained in Example 5 (sample 7, 300.1 g) were placed in a film coating machine (HCT-MINI type, manufactured by Freund Corporation), and film-coated tablets (about 312 mg per tablet) were obtained while spraying a film coating solution (143.5 g) having the composition ratio shown in Table 22. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 2 or 6 months.

TABLE 22

| Composition of aqueous film coating solution | |
|---|---|
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 21

Sample 23

The plain tablets (core tablets) obtained in Example 6 (sample 8, 300.1 g) were placed in a film coating machine (HCT-MINI type, manufactured by Freund Corporation), and film-coated tablets (about 312 mg per tablet) were obtained while spraying a film coating solution (158.3 g) having the composition ratio shown in Table 23. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 2 or 6 months.

TABLE 23

| Composition of aqueous film coating solution | |
| --- | --- |
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 22

Sample 24

The plain tablets (core tablets) obtained in Example 7 (sample 9, 300.0 g) were placed in a film coating machine (HCT-MINI type, manufactured by Freund Corporation), and film-coated tablets (about 312 mg per tablet) were obtained while spraying a film coating solution (138.1 g) having the composition ratio shown in Table 24. The obtained film-coated tablet was placed in a glass bottle, tightly sealed and preserved at 60° C. for 2 weeks, and at 40° C., 75% RH for 2 or 6 months. The film-coated tablet was placed in a glass bottle, and preserved in an open bottle at 40° C., 75% RH for 2 or 6 months.

TABLE 24

| Composition of aqueous film coating solution | |
| --- | --- |
| composition | amount (mg) |
| 1) hypromellose | 10.8 |
| 2) titanium oxide | 1 |
| 3) diiron trioxide | 0.2 |
| 4) purified water | 108 |
| total | 120.0 |

Example 23

Sample 25

The plain tablets (core tablets) obtained in Example 8 (sample 10, 350.1 g) were placed in a film coating machine (HCT-MINI type, manufactured by Freund Corporation), and film-coated tablets (about 209 mg per tablet) were obtained while spraying a film coating solution (192.0 g) having the composition ratio shown in Table 25. The obtained film-coated tablet was placed in a glass bottle, tightly sealed and preserved at 60° C. for 2 weeks, and at 40° C., 75% RH for 2 months. The film-coated tablet was placed in a glass bottle, and preserved in an open bottle at 40° C., 75% RH for 2 months.

TABLE 25

| Composition of aqueous film coating solution | |
| --- | --- |
| composition | amount (mg) |
| 1) hypromellose | 6.732 |
| 2) macrogol 6000 | 1.350 |
| 3) titanium oxide | 0.9 |
| 4) diiron trioxide | 0.018 |
| 5) purified water | 90 |
| total | 99.0 |

Example 24

Sample 26

The plain tablets (core tablets) obtained in Example 9 (sample 11, 350.0 g) were placed in a film coating machine (HCT-MINI type, manufactured by Freund Corporation), and film-coated tablets (about 209 mg per tablet) were obtained while spraying a film coating solution (182.3 g) having the composition ratio shown in Table 26. The obtained film-coated tablet was placed in a glass bottle, tightly sealed and preserved at 60° C. for 2 weeks, and at 40° C., 75% RH for 2 months. The film-coated tablet was placed in a glass bottle, and preserved in an open bottle at 40° C., 75% RH for 2 months.

TABLE 26

| Composition of aqueous film coating solution | |
| --- | --- |
| composition | amount (mg) |
| 1) hypromellose | 6.732 |
| 2) macrogol 6000 | 1.350 |
| 3) titanium oxide | 0.9 |
| 4) diiron trioxide | 0.018 |
| 5) purified water | 90 |
| total | 99.0 |

Example 25

Sample 27

The plain tablets (core tablets) obtained in Example 10 (sample 12, 350.1 g) were placed in a film coating machine (HCT-MINI type, manufactured by Freund Corporation), and film-coated tablets (about 209 mg per tablet) were obtained while spraying a film coating solution (189.0 g) having the composition ratio shown in Table 27. The obtained film-coated tablet was placed in a glass bottle, tightly sealed and preserved at 60° C. for 2 weeks, and at 40° C., 75% RH for 2 months. The film-coated tablet was placed in a glass bottle, and preserved in an open bottle at 40° C., 75% RH for 2 months.

TABLE 27

Composition of aqueous film coating solution

| composition | amount (mg) |
|---|---|
| 1) hypromellose | 6.732 |
| 2) macrogol 6000 | 1.350 |
| 3) titanium oxide | 0.9 |
| 4) diiron trioxide | 0.018 |
| 5) purified water | 90 |
| total | 99.0 |

Example 26

Sample 28

The plain tablets (core tablets) obtained in Example 11 (sample 13, 240.1 g) were placed in a film coating machine (HCT-MINI type, manufactured by Freund Corporation), and film-coated tablets (about 209 mg per tablet) were obtained while spraying a film coating solution (126.3 g) having the composition ratio shown in Table 28. The obtained film-coated tablet was placed in a glass bottle, tightly sealed and preserved at 60° C. for 2 weeks, and at 40° C., 75% RH for 2 months. The film-coated tablet was placed in a glass bottle, and preserved in an open bottle at 40° C., 75% RH for 2 months.

TABLE 28

Composition of aqueous film coating solution

| composition | amount (mg) |
|---|---|
| 1) hypromellose | 6.732 |
| 2) macrogol 6000 | 1.350 |
| 3) titanium oxide | 0.9 |
| 4) diiron trioxide | 0.018 |
| 5) purified water | 90 |
| total | 99.0 |

Example 27

Sample 29

The plain tablets (core tablets) obtained in Example 12 (sample 14, 3300.0 g) were placed in a film coating machine (DRC-500, manufactured by POWREX CORPORATION), and film-coated tablets (about 229 mg per tablet) were obtained while spraying a film coating solution (1480.9 g) having the composition ratio shown in Table 29. The film-coated tablet was placed in a glass bottle, and preserved in an open bottle at 40° C., 75% RH for 2 months.

TABLE 29

Composition of aqueous film coating solution

| composition | amount (mg) |
|---|---|
| 1) hypromellose | 6.6 |
| 2) macrogol 6000 | 1.5 |
| 3) titanium oxide | 0.75 |
| 4) yellow ferric oxide | 0.075 |
| 5) diiron trioxide | 0.075 |
| 6) purified water | 81 |
| total | 90.0 |

Example 28

Sample 30

The plain tablets (core tablets) obtained in Example 13 (sample 15, 3300.0 g) were placed in a film coating machine (DRC-500, manufactured by POWREX CORPORATION), and film-coated tablets (about 229 mg per tablet) were obtained while spraying a film coating solution (1501.0 g) having the composition ratio shown in Table 30. The film-coated tablet was placed in a glass bottle, and preserved in a closed bottle or an open bottle at 40° C., 75% RH for 2 months.

TABLE 30

Composition of aqueous film coating solution

| composition | amount (mg) |
|---|---|
| 1) hypromellose | 6.6 |
| 2) macrogol 6000 | 1.5 |
| 3) titanium oxide | 0.75 |
| 4) yellow ferric oxide | 0.075 |
| 5) diiron trioxide | 0.075 |
| 6) purified water | 81 |
| total | 90.0 |

Example 29

Sample 31

The plain tablets (core tablets) obtained in Example 14 (sample 16, 3300.0 g) were placed in a film coating machine (DRC-500, manufactured by POWREX CORPORATION), and film-coated tablets (about 229 mg per tablet) were obtained while spraying a film coating solution (1514.0 g) having the composition ratio shown in Table 31. The film-coated tablet was placed in a glass bottle, and preserved in a closed bottle or an open bottle at 40° C., 75% RH for 2 months.

TABLE 31

Composition of aqueous film coating solution

| composition | amount (mg) |
|---|---|
| 1) hypromellose | 6.6 |
| 2) macrogol 6000 | 1.5 |
| 3) titanium oxide | 0.75 |
| 4) yellow ferric oxide | 0.075 |
| 5) diiron trioxide | 0.075 |
| 6) purified water | 81 |
| total | 90.0 |

Example 30

Sample 32

The plain tablets (core tablets) obtained in Example 15 (sample 17, 3300.0 g) were placed in a film coating machine (DRC-500, manufactured by POWREX CORPORATION), and film-coated tablets (about 229 mg per tablet) were obtained while spraying a film coating solution (1374.0 g) having the composition ratio shown in Table 32. The film-coated tablet was placed in a glass bottle, and preserved in a closed bottle or an open bottle at 40° C., 75% RH for 2 months.

TABLE 32

| Composition of aqueous film coating solution | |
|---|---|
| composition | amount (mg) |
| 1) hypromellose | 6.6 |
| 2) macrogol 6000 | 1.5 |
| 3) titanium oxide | 0.75 |
| 4) yellow ferric oxide | 0.075 |
| 5) diiron trioxide | 0.075 |
| 6) purified water | 81 |
| total | 90.0 |

Comparative Example 3

Sample 33

A plain tablet (core tablet) containing N-methyl-1-[5-(2-methylphenyl)-1-(pyridin-3-ylsulfonyl)-1H-pyrrol-3-yl] methanamine fumarate (hereinafter to be referred to as compound B) was produced as follows at the composition ratio shown in Table 33.

That is, compound B (2.680 g), mannitol (483.320 g) and crystalline cellulose (60.0 g) were placed in a fluidized bed dryer granulator (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. Croscarmellose sodium (27.00 g) and magnesium stearate (5.400 g) were added to the sized powder (507.6 g) and mixed to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet).

TABLE 33

| Composition of plain tablet (core tablet) containing compound B | |
|---|---|
| composition | amount (mg) |
| 1) compound B | 1.340 |
| 2) mannitol | 241.66 |
| 3) crystalline cellulose | 30 |
| 4) hydroxypropylcellulose | 9 |
| 5) croscarmellose sodium | 15 |
| 6) magnesium stearate | 3 |
| total | 300.0 |

Comparative Example 4

Sample 34

The plain tablets (core tablets) obtained in Comparative Example 3 (sample 33, 200.0 g) were placed in a film coating machine (DRC-200, manufactured by POWREX CORPORATION), and film-coated tablets (about 312 mg per tablet) were obtained while spraying a film coating solution (96.8 g) having the composition ratio shown in Table 34. The obtained film-coated tablet was placed in a glass bottle, tightly sealed and preserved at 40° C., 75% RH for 2 months. The film-coated tablet was placed in a glass bottle, and preserved in an open bottle at 40° C., 75% RH for 2 months.

TABLE 34

| composition of aqueous film coating solution | |
|---|---|
| composition | amount (mg) |
| 1) hypromellose | 8.8 |
| 2) polyethylene glycol | 2 |
| 3) titanium oxide | 1 |
| 4) diiron trioxide | 0.2 |
| 5) purified water | 108 |
| total | 120.0 |

Example 31

Sample 35

A plain tablet (core tablet) containing compound B was produced as follows at the composition ratio shown in Table 35.

That is, compound B (24.54 g), mannitol (4223.0 g), crystalline cellulose (540.0 g) and fumaric acid (126.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.0 g) was passed through a power-mill (P-3, manufactured by Showa Kagaku Kikai Kosakusho) to give a sized powder. The sized powder (4230.0 g), croscarmellose sodium (225.0 g) and magnesium stearate (45.00 g) were placed in a tumbler mixer (TM-15S, manufactured by Showa Kagaku Kikai Kosakusho), and mixed to give a mixed powder. The mixed powder was tableted by a rotary tableting machine (COLLECT 12HUK, manufactured by Kikusui Seisakusho, Ltd.) using a 9 mmϕ punch to give plain tablets (core tablets, 300 mg per tablet).

TABLE 35

| Composition of plain tablet (core tablet) containing compound B | |
|---|---|
| composition | amount (mg) |
| 1) compound B | 1.340 |
| 2) mannitol | 234.66 |
| 3) crystalline cellulose | 30 |
| 4) hydroxypropylcellulose | 9 |
| 5) fumaric acid | 7 |
| 6) croscarmellose sodium | 15 |
| 7) magnesium stearate | 3 |
| total | 300.0 |

Example 32

Sample 36

The plain tablets (core tablets) obtained in Example 31 (sample 35, 3300.0 g) were placed in a film coating machine (DRC-500, manufactured by POWREX CORPORATION), and film-coated tablets (about 312 mg per tablet) were obtained while spraying a film coating solution (1432.0 g) having the composition ratio shown in Table 34. The obtained film-coated tablet was placed in a glass bottle, tightly sealed and preserved at 40° C., 75% RH for 2 months. The film-coated tablet was placed in a glass bottle, and preserved in an open bottle at 40° C., 75% RH for 2 months.

Example 33

Sample 37

A plain tablet (core tablet) containing compound B was produced as follows at the composition ratio shown in Table 36.

That is, compound B (5.360 g), mannitol (479.2 g) and crystalline cellulose (60.00 g) were placed in a fluidized bed dryer granulator (LAB-1, manufactured by POWREX CORPORATION), and the mixture was preheated and mixed. The mixture was granulated while spraying an aqueous solution (301.4 g) of hydroxypropylcellulose (18.0 g) and fumaric acid (0.60 g) to give a granulated powder. The obtained granulated powder was passed through a 16M (1000 μm) sieve to give a sized powder. Croscarmellose sodium (24.75 g) and magnesium stearate (4.950 g) were added to the sized powder (465.3 g), and mixed to give a mixed powder. The mixed powder was tableted by a rotary tableting machine (COLLECT 19K, manufactured by Kikusui Seisakusho, Ltd.) using a 7 mmφ punch to give plain tablets (core tablets, 150 mg per tablet).

TABLE 36

Composition of plain tablet (core tablet) containing compound B

| composition | amount (mg) |
| --- | --- |
| 1) compound B | 1.340 |
| 2) mannitol | 119.81 |
| 3) crystalline cellulose | 15 |
| 4) hydroxypropylcellulose | 4.5 |
| 5) fumaric acid | 0.35 |
| 6) croscarmellose sodium | 7.5 |
| 7) magnesium stearate | 1.5 |
| total | 150.0 |

Example 34

Sample 38

The plain tablets (core tablets) obtained in Example 33 (sample 37, 180.3 g) were placed in a film coating machine (DRC-200, manufactured by POWREX CORPORATION), and film-coated tablets (core tablet, 156.1 mg per tablet) while spraying a film coating solution (75.0 g) having the composition ratio shown in Table 37. The obtained film-coated tablet was placed in a glass bottle, tightly sealed and preserved at 40° C., 75% RH for 2 months. The film-coated tablet was placed in a glass bottle, and preserved in an open bottle at 40° C., 75% RH for 2 months.

TABLE 37 composition of aqueous film coating solution

| composition | amount (mg) |
| --- | --- |
| 1) hypromellose | 4.47 |
| 2) macrogol 6000 | 1.02 |
| 3) titanium oxide | 0.508 |
| 4) yellow ferric oxide | 0.051 |
| 5) diiron trioxide | 0.051 |
| 6) purified water | 54.9 |
| total | 61.0 |

Example 35

Sample 39

A plain tablet (core tablet) containing compound B was produced as follows at the composition ratio shown in Table 38.

That is, compound B (24.54 g), mannitol (4223.0 g), crystalline cellulose (540.0 g) and fumaric acid (126.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.0 g) was passed through a power-mill (P-3, manufactured by Showa Kagaku Kikai Kosakusho) to give a sized powder. The sized powder (4230.0 g), croscarmellose sodium (225.0 g) and magnesium stearate (45.00 g) were placed in a tumbler mixer (TM-15S, manufactured by Showa Kagaku Kikai Kosakusho), and mixed to give a mixed powder. The mixed powder was tableted by a rotary tableting machine (COLLECT 12HUK, manufactured by Kikusui Seisakusho, Ltd.) using a 7 mmφ punch to give plain tablets (core tablets, 150 mg per tablet).

TABLE 38

Composition of plain tablet (core tablet) containing compound B

| composition | amount (mg) |
| --- | --- |
| 1) compound B | 0.67 |
| 2) mannitol | 117.33 |
| 3) crystalline cellulose | 15 |
| 4) hydroxypropylcellulose | 4.5 |
| 5) fumaric acid | 3.5 |
| 6) croscarmellose sodium | 7.5 |
| 7) magnesium stearate | 1.5 |
| total | 150.0 |

Example 36

Sample 40

The plain tablets (core tablets) obtained in Example 35 (sample 39, 3300.0 g) were placed in a film coating machine (DRC-500, manufactured by POWREX CORPORATION), and film-coated tablets (about 156 mg per tablet) were obtained while spraying a film coating solution (1470.0 g) having the composition ratio shown in Table 34. The obtained film-coated tablet was placed in a glass bottle, tightly sealed and preserved at 40° C., 75% RH for 2 months. The film-coated tablet was placed in a glass bottle, and preserved in an open bottle at 40° C., 75% RH for 2 months.

Example 37

Sample 41

A plain tablet (core tablet) containing compound B was produced as follows at the composition ratio shown in Table 39.

That is, compound B (245.4 g), mannitol (4003.0 g), crystalline cellulose (540.0 g) and fumaric acid (126.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.0 g) was passed through a powermill (P-3, manufactured by Showa Kagaku Kikai Kosakusho) to give a sized powder. The sized powder (4230.0 g), croscarmellose sodium (225.0 g) and magnesium stearate (45.00 g) were placed in a tumbler mixer (TM-15S, manufactured by Showa Kagaku Kikai Kosakusho), and mixed to give a mixed powder. The mixed powder was tableted by a rotary tableting machine (COLLECT 12HUK, manufactured by Kikusui Seisakusho, Ltd.) using a 9 mmϕ punch to give plain tablets (core tablets, 300 mg per tablet).

TABLE 39

Composition of plain tablet (core tablet) containing compound B

| composition | amount (mg) |
|---|---|
| 1) compound B | 13.4 |
| 2) mannitol | 222.6 |
| 3) crystalline cellulose | 30 |
| 4) hydroxypropylcellulose | 9 |
| 5) fumaric acid | 7 |
| 6) croscarmellose sodium | 15 |
| 7) magnesium stearate | 3 |
| total | 300.0 |

Example 38

Sample 42

The plain tablets (core tablets) obtained in Example 37 (sample 41, 3300.0 g) were placed in a film coating machine (DRC-500, manufactured by POWREX CORPORATION), and film-coated tablets (about 312 mg per tablet) were obtained while spraying a film coating solution (1425.0 g) having the composition ratio shown in Table 34. The obtained film-coated tablet was placed in a glass bottle, tightly sealed and preserved at 40° C., 75% RH for 2 months. The film-coated tablet was placed in a glass bottle, and preserved in an open bottle at 40° C., 75% RH for 2 months.

Example 39

Sample 43

A plain tablet (core tablet) containing compound B was produced as follows at the composition ratio shown in Table 40.

That is, compound B (981.5 g), mannitol (3267.0 g), crystalline cellulose (540.0 g) and fumaric acid (126.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.0 g) was passed through a powermill (P-3, manufactured by Showa Kagaku Kikai Kosakusho) to give a sized powder. The sized powder (4230.0 g), croscarmellose sodium (225.0 g) and magnesium stearate (45.00 g) were placed in a tumbler mixer (TM-15S, manufactured by Showa Kagaku Kikai Kosakusho), and mixed to give a mixed powder. The mixed powder was tableted by a rotary tableting machine (COLLECT 12HUK, manufactured by Kikusui Seisakusho, Ltd.) using a 9 mmϕ punch to give plain tablets (core tablets, 300 mg per tablet).

TABLE 40

Composition of plain tablet (core tablet) containing compound B

| composition | amount (mg) |
|---|---|
| 1) compound B | 53.6 |
| 2) mannitol | 182.4 |
| 3) crystalline cellulose | 30 |
| 4) hydroxypropylcellulose | 9 |
| 5) fumaric acid | 7 |
| 6) croscarmellose sodium | 15 |
| 7) magnesium stearate | 3 |
| total | 300.0 |

Example 40

Sample 44

The plain tablets (core tablets) obtained in Example 39 (sample 43, 3300.0 g) were placed in a film coating machine (DRC-500, manufactured by POWREX CORPORATION), and film-coated tablets (about 312 mg per tablet) were obtained while spraying a film coating solution (1417.2 g) having the composition ratio shown in Table 34. The obtained film-coated tablet was placed in a glass bottle, tightly sealed and preserved at 40° C., 75% RH for 2 months. The film-coated tablet was placed in a glass bottle, and preserved in an open bottle at 40° C., 75% RH for 2 months.

Comparative Example 5

Sample 45

A plain tablet (core tablet) containing 1-[(4-fluoro-5-(2-fluoropyridin-3-yl)-1-(pyridin-3-ylsulfonyl)-1H-pyrrol-3-yl]-N-methylmethanamine fumarate (hereinafter to be referred to as compound C) was produced as follows at the composition ratio shown in Table 41.

That is, compound C (2.318 g), mannitol (483.7 g) and crystalline cellulose (60.0 g) were placed in a fluidized-bed dryer (LAB-1, manufactured by POWREX CORPORATION), and the mixture was preheated and mixed. The mixture was granulated while spraying an aqueous solution (300.0 g) of hydroxypropylcellulose (18.0 g) to give a granulated powder. The obtained granulated powder was passed through a 16M (1000 μm) sieve to give a sized powder. Croscarmellose sodium (27.0 g) and magnesium stearate (5.40 g) were added to the sized powder (507.6 g), and mixed in a bag to give a mixed powder. The mixed powder was tableted by a rotary tableting machine (COLLECT 19K, manufactured by Kikusui Seisakusho, Ltd.) using a 9 mmφ punch to give plain tablets (core tablets, 300 mg per tablet).

TABLE 41

Composition of plain tablet (core tablet) containing compound C

| composition | amount (mg) |
|---|---|
| 1) compound C | 1.159 |
| 2) mannitol | 238.841 |
| 3) crystalline cellulose | 30 |
| 4) hydroxypropylcellulose | 9 |
| 5) croscarmellose sodium | 15 |
| 6) magnesium stearate | 3 |
| total | 300.0 |

Comparative Example 6

Sample 46

The plain tablets (core tablets) obtained in Comparative Example 5 (sample 45, 200.0 g) were placed in a film coating machine (Hicoater mini, manufactured by Freund Corporation), and film-coated tablets (about 312 mg per tablet) were obtained while spraying a film coating solution (136.3 g) having the composition ratio shown in Table 42. The obtained film-coated tablet was placed in a glass bottle, tightly sealed and preserved at 40° C., 75% RH for 1 month. The film-coated tablet was placed in a glass bottle, and preserved in an open bottle at 40° C., 75% RH for 1 month.

TABLE 42 composition of aqueous film coating solution

| composition | amount (mg) |
|---|---|
| 1) hypromellose | 8.8 |
| 2) polyethylene glycol | 2 |
| 3) titanium oxide | 1 |
| 4) diiron trioxide | 0.2 |
| 5) purified water | 108 |
| total | 120.0 |

Example 41

Sample 47

A plain tablet (core tablet) containing compound C was produced as follows at the composition ratio shown in Table 43.

That is, compound C (2.318 g), mannitol (482.082 g) and crystalline cellulose (60 g) were placed in a fluidized bed dryer granulator (LAB-1, manufactured by POWREX CORPORATION), preheated and mixed. A granulated powder was obtained while spraying an aqueous solution (300.0 g) of tartaric acid (1.60 g) and hydroxypropylcellulose (18.0 g). The obtained granulated powder was passed through a 16M (1000 μm) sieve to give a sized powder. Croscarmellose sodium (24.08 g) and magnesium stearate (4.81 g) were added to the sized powder (451.2 g), and mixed in a bag to give a mixed powder. The mixed powder was tableted by a rotary tableting machine (COLLECT 19K, manufactured by Kikusui Seisakusho, Ltd.) using a 9 mmφ punch to give plain tablets (core tablets, 300 mg per tablet).

TABLE 43

Composition of plain tablet (core tablet) containing compound C

| composition | amount (mg) |
|---|---|
| 1) compound C | 1.159 |
| 2) mannitol | 241.041 |
| 3) crystalline cellulose | 30 |
| 4) hydroxypropylcellulose | 9 |
| 5) tartaric acid | 0.8 |
| 6) croscarmellose sodium | 15 |
| 7) magnesium stearate | 3 |
| total | 300.0 |

Example 42

Sample 48

The plain tablets (core tablets) obtained in Example 41 (sample 47, 200.23 g) were placed in a film coating machine (Hicoater mini, manufactured by Freund Corporation), and film-coated tablets (about 312 mg per tablet) were obtained while spraying a film coating solution (101.7 g) having the composition ratio shown in Table 42. The obtained film-coated tablet was placed in a glass bottle, tightly sealed and preserved at 40° C., 75% RH for 1 month.

Example 43

Sample 49

A plain tablet (core tablet) containing compound C was produced as follows at the composition ratio shown in Table 44.

That is, compound C (6.954 g), mannitol (477.4 g) and crystalline cellulose (60 g) were placed in a fluidized bed dryer granulator (LAB-1, manufactured by POWREX CORPORATION), preheated and mixed. A granulated powder was obtained while spraying an aqueous solution (300.0 g) of tartaric acid (1.60 g) and hydroxypropylcellulose (18.0 g). The obtained granulated powder was passed through a 16M (1000 μm) sieve to give a sized powder. The sized powder (376.0 g), croscarmellose sodium (20.00 g) and magnesium stearate (4.00 g) were added, and mixed to give a mixed powder. The mixed powder was tableted by a rotary tableting machine (COLLECT 19K, manufactured by Kikusui Seisakusho, Ltd.) using a 6 mmφ punch to give plain tablets (core tablets, 100 mg per tablet).

TABLE 44

Composition of plain tablet (core tablet) containing compound C

| composition | amount (mg) |
|---|---|
| 1) compound C | 1.159 |
| 2) mannitol | 79.5743 |
| 3) crystalline cellulose | 30 |
| 4) hydroxypropylcellulose | 3 |
| 5) tartaric acid | 0.2667 |
| 6) croscarmellose sodium | 5 |
| 7) magnesium stearate | 1 |
| total | 100.0 |

Example 44

Sample 50

The plain tablets (core tablets) obtained in Example 43 (sample 49, 280.03 g) were placed in a film coating machine (Hicoater mini, manufactured by Freund Corporation), and film-coated tablets (about 104 mg per tablet) were obtained while spraying a film coating solution (115.4 g) having the composition ratio shown in Table 42. The obtained film-coated tablet was placed in a glass bottle, tightly sealed and preserved at 40° C., 75% RH for 1 month. The film-coated tablet was placed in a glass bottle, and preserved in an open bottle at 40° C., 75% RH for 1 month.

Experimental Example 1

Decomposed Product Measurement Method

The film-coated tablets of Comparative Example 2 and Examples 16-30 and the core tablets of Examples 1-3 were examined for production of decomposed product U-6 of compound A (relative retention time: about 0.70) and other decomposed products before preservation (initial) and after preservation. The decomposed product was measured by extracting the tablets with 0.05 mol/L phosphoric acid/MeCN mixture (19:1) or water/MeCN mixture (19:1) by HPLC. The HPLC test conditions are as follows.

detector: ultraviolet absorption spectrophotometer (measurement wavelength: 230 nm)

column: CAPCELL PAK C18 MGII, 3 μm, 4.6 mm i.d.× 150 mm (manufactured by Shiseido Co., Ltd.)

column temperature: fixed temperature around 25° C.

mobile phase A:0.05 mol/L sodium phosphate buffer (pH 6.0)/acetonitrile mixture (95:5)

mobile phase B:0.05 mol/L sodium phosphate buffer (pH 6.0)/acetonitrile mixture (40:60)

mobile phase delivery: density gradient was controlled by changing mixing ratio of mobile phase A and mobile phase B as follows.

TABLE 45

| time (min) after injection | mobile phase A (%) | mobile phase B (%) |
|---|---|---|
| 0 | 100 | 0 |
| 10 | 80 | 20 |
| 60 | 70 | 30 |
| 110 | 0 | 100 |
| 110.1 | 100 | 0 |
| 120 | 100 | 0 | measurement range of peak area: 110 min

Experiment Results 1

The decomposed products before preservation and after preservation at 60° C. for 2 weeks were measured, and the results of total decomposed product and U-6 that remarkably increased in the absence of organic acid are shown in Table 46.

TABLE 46 decomposed product after preservation at 60° C. for 2 weeks

| sample | core tablet or film-coated tablet | compound A concentration (%) | organic acid concentration (%) | preservation state | before preservation total decomposed product (%) | before preservation decomposed product U-6 (%) | after preservation total decomposed product (%) | after preservation decomposed product U-6 (%) |
|---|---|---|---|---|---|---|---|---|
| sample 2 (comparison control) | film-coated tablet | 0.4 | 0 | closed glass bottle | 0.68 | 0.31 | 2.00 | 1.48 |
| sample 3 | core tablet | 0.4 | 0.3 | closed glass bottle | 0.92 | 0.27 | 1.20 | 0.55 |
| sample 4 | core tablet | 0.4 | 10 | closed glass bottle | 0.90 | 0.26 | 1.12 | 0.48 |
| sample 5 | core tablet | 0.4 | 10 | closed glass bottle | 0.91 | 0.27 | 1.16 | 0.48 |
| sample 18 | film-coated tablet | 0.4 | 0.3 | closed glass bottle | 0.88 | 0.26 | 1.15 | 0.54 |
| sample 19 | film-coated tablet | 0.4 | 10 | closed glass bottle | 0.89 | 0.26 | 1.11 | 0.49 |
| sample 20 | film-coated tablet | 0.4 | 10 | closed glass bottle | 0.88 | 0.26 | 1.12 | 0.48 |
| sample 21 | film-coated tablet | 0.4 | 0.3 | closed glass bottle | 0.91 | 0.28 | 1.90 | 1.28 |
| sample 22 | film-coated tablet | 0.4 | 0.5 | closed glass bottle | 0.95 | 0.28 | 1.65 | 1.04 |
| sample 23 | film-coated tablet | 0.4 | 1.0 | closed glass bottle | 0.86 | 0.26 | 1.41 | 0.85 |
| sample 24 | film-coated tablet | 0.4 | 2.3 | closed glass bottle | 0.86 | 0.26 | 1.07 | 0.30 |
| sample 25 | film-coated tablet | 3.3 | 2.5 | closed glass bottle | 0.76 | 0.25 | 0.80 | 0.30 |
| sample 26 | film-coated tablet | 13.4 | 2.5 | closed glass bottle | 0.74 | 0.25 | 0.77 | 0.27 |
| sample 27 | film-coated tablet | 26.7 | 2.5 | closed glass bottle | 0.60 | 0.20 | 0.61 | 0.20 |
| sample 28 | film-coated tablet | 26.7 | 10 | closed glass bottle | 0.61 | 0.20 | 0.61 | 0.20 |

Experiment Results 2

The decomposed products before preservation and after preservation at 40° C., 75% RH for 2 months were measured, and the results of total decomposed product and U-6 that remarkably increased in the absence of organic acid are shown in Table 47.

TABLE 47 decomposed product after preservation at 40° C., 75% RH for 2 months

| sample | core tablet or film-coated tablet | compound A concentration (%) | organic acid concentration (%) | preservation state | before preservation total decomposed product (%) | before preservation decomposed product U-6 (%) | after preservation total decomposed product (%) | after preservation decomposed product U-6 (%) |
|---|---|---|---|---|---|---|---|---|
| sample 2 (comparison control) | film-coated tablet | 0.4 | 0 | closed glass bottle | 0.68 | 0.31 | 1.91 | 1.38 |
| sample 18 | film-coated tablet | 0.4 | 0.3 | closed glass bottle | 0.88 | 0.26 | 1.11 | 0.47 |
| | | | | open glass bottle | 0.88 | 0.26 | 0.99 | 0.39 |
| sample 19 | film-coated tablet | 0.4 | 10.0 | closed glass bottle | 0.89 | 0.26 | 1.03 | 0.44 |
| | | | | open glass bottle | 0.89 | 0.26 | 1.38 | 0.37 |
| sample 20 | film-coated tablet | 0.4 | 10.0 | closed glass bottle | 0.88 | 0.26 | 1.08 | 0.47 |
| | | | | open glass bottle | 0.88 | 0.26 | 1.09 | 0.37 |
| sample 21 | film-coated tablet | 0.4 | 0.3 | closed glass bottle | 0.91 | 0.28 | 1.90 | 1.08 |
| | | | | open glass bottle | 0.91 | 0.28 | 1.17 | 0.52 |
| sample 22 | film-coated tablet | 0.4 | 0.5 | closed glass bottle | 0.95 | 0.28 | 1.47 | 0.87 |
| | | | | open glass bottle | 0.95 | 0.28 | 1.00 | 0.46 |
| sample 23 | film-coated tablet | 0.4 | 1.0 | closed glass bottle | 0.86 | 0.26 | 1.45 | 0.74 |
| | | | | open glass bottle | 0.86 | 0.26 | 0.97 | 0.40 |
| sample 24 | film-coated tablet | 0.4 | 2.3 | closed glass bottle | 0.86 | 0.26 | 1.01 | 0.43 |
| | | | | open glass bottle | 0.86 | 0.26 | 1.08 | 0.35 |
| sample 25 | film-coated tablet | 3.3 | 2.5 | closed glass bottle | 0.76 | 0.25 | 0.95 | 0.32 |
| | | | | open glass bottle | 0.76 | 0.25 | 0.81 | 0.30 |
| sample 26 | film-coated tablet | 13.4 | 2.5 | closed glass bottle | 0.74 | 0.25 | 0.84 | 0.30 |
| | | | | open glass bottle | 0.74 | 0.25 | 0.80 | 0.28 |
| sample 27 | film-coated tablet | 26.7 | 2.5 | closed glass bottle | 0.60 | 0.20 | 0.78 | 0.30 |
| | | | | open glass bottle | 0.60 | 0.20 | 0.74 | 0.28 |
| sample 28 | film-coated tablet | 26.7 | 2.5 | closed glass bottle | 0.61 | 0.20 | 0.87 | 0.29 |
| | | | | open glass bottle | 0.61 | 0.20 | 1.23 | 0.39 |
| sample 29 | film-coated tablet | 1.5 | 2.5 | closed glass bottle | 0.74 | 0.31 | 0.98 | 0.45 |
| | | | | open glass bottle | 0.74 | 0.31 | 0.75 | 0.35 |
| sample 30 | film-coated tablet | 3.0 | 2.5 | closed glass bottle | 0.71 | 0.29 | 0.81 | 0.34 |
| | | | | open glass bottle | 0.71 | 0.29 | 0.70 | 0.30 |
| sample 31 | film-coated tablet | 6.1 | 2.5 | closed glass bottle | 0.79 | 0.29 | 0.83 | 0.32 |
| | | | | open glass bottle | 0.79 | 0.29 | 0.75 | 0.29 |
| sample 32 | film-coated tablet | 12.1 | 2.5 | closed glass bottle | 0.68 | 0.27 | 0.72 | 0.29 |
| | | | | open glass bottle | 0.68 | 0.27 | 0.74 | 0.27 |

Experiment Results 3

The decomposed products before preservation and after preservation at 40° C., 75% RH for 6 months were measured, and the results of total decomposed product and U-6 that remarkably increased in the absence of organic acid are shown in Table 48.

TABLE 48 decomposed product after preservation at 40° C., 75% RH for 6 months

| sample | core tablet or film-coated tablet | compound A concentration (%) | organic acid concentration (%) | preservation state | before preservation total decomposed product (%) | before preservation decomposed product U-6 (%) | after preservation total decomposed product (%) | after preservation decomposed product U-6 (%) |
|---|---|---|---|---|---|---|---|---|
| sample 2 (comparison control) | film-coated tablet | 0.4 | 0 | closed glass bottle | 0.68 | 0.31 | 2.80 | 2.07 |
| | | | | open glass bottle | 0.68 | 0.31 | 3.19 | 2.1 |
| sample 18 | film-coated tablet | 0.4 | 0.3 | closed glass bottle | 0.88 | 0.26 | 1.45 | 0.65 |
| | | | | open glass bottle | 0.88 | 0.26 | 1.18 | 0.50 |
| sample 19 | film-coated tablet | 0.4 | 10.0 | closed glass bottle | 0.89 | 0.26 | 1.03 | 0.54 |
| | | | | open glass bottle | 0.89 | 0.26 | 1.49 | 0.46 |
| sample 20 | film-coated tablet | 0.4 | 10.0 | closed glass bottle | 0.88 | 0.26 | 1.21 | 0.58 |
| | | | | open glass bottle | 0.88 | 0.26 | 1.77 | 0.48 |
| sample 21 | film-coated tablet | 0.4 | 0.3 | closed glass bottle | 0.91 | 0.28 | 2.66 | 1.77 |
| | | | | open glass bottle | 0.91 | 0.28 | 1.59 | 0.87 |

TABLE 48-continued decomposed product after preservation at 40° C., 75% RH for 6 months

| sample | core tablet or film-coated tablet | compound A concentration (%) | organic acid concentration (%) | preservation state | before preservation | | after preservation | |
|---|---|---|---|---|---|---|---|---|
| | | | | | total decomposed product (%) | decomposed product U-6 (%) | total decomposed product (%) | decomposed product U-6 (%) |
| sample 22 | film-coated tablet | 0.4 | 0.5 | closed glass bottle | 0.95 | 0.28 | 2.32 | 1.45 |
| | | | | open glass bottle | 0.95 | 0.28 | 1.50 | 0.66 |
| sample 23 | film-coated tablet | 0.4 | 1.0 | closed glass bottle | 0.86 | 0.26 | 1.92 | 1.12 |
| | | | | open glass bottle | 0.86 | 0.26 | 1.16 | 0.58 |
| sample 24 | film-coated tablet | 0.4 | 2.3 | closed glass bottle | 0.86 | 0.26 | 1.29 | 0.65 |
| | | | | open glass bottle | 0.86 | 0.26 | 1.15 | 0.49 |

By the addition of an organic acid, an increase in the decomposed product U-6 was suppressed irrespective of the preservation conditions and preservation state. Particularly, an increase in the decomposed product U-6, which strikingly increases in the absence of an organic acid, was remarkably suppressed.

U-6 was remarkably suppressed when fumaric acid was added during granulation by any of solution/dispersion addition including dissolving or dispersing fumaric acid in water and spraying the solution or dispersion, powder addition including addition of organic acid as a powder, and a combination of solution/dispersion addition and powder addition.

An increase in the decomposed product was suppressed as the concentration of the organic acid in the tablet became higher. When the organic acid concentration was 1% or above, an increase in U-6 was strikingly suppressed. When it was 2% or above, the suppressive effect was still more remarkable.

By the addition of an organic acid, a remarkable decomposed product suppressive effect was observed in both a plain tablet (core tablet) and a film-coated tablet, and the plain tablet (core tablet) and the film-coated tablet showed no difference in the amount of increase.

By the addition of an organic acid, a decomposed product suppressive effect was observed irrespective of the concentration of compound A.

Experimental Example 2

Measurement Method of Decomposed Product

The film-coated tablets of Comparative Example 4 were examined for the production of compound B decomposed product U-1 (relative retention time: about 0.75) and other decomposed products, before preservation (initial) and after preservation (sample 34). The decomposed product was measured by extracting the tablets with water/MeCN mixture (1:3) by HPLC. The HPLC test conditions are as follows.

detector: ultraviolet absorption spectrophotometer (measurement wavelength: 230 nm)

column: CAPCELL PAK C18 MGII, 3 μm, 4.6 mm i.d.× 100 mm (manufactured by Shiseido Co., Ltd.)

column temperature: fixed temperature around 40° C.

mobile phase A: 0.05 mol/L sodium phosphate buffer (pH 7.0)/acetonitrile mixture (9:1)

mobile phase B: 0.05 mol/L sodium phosphate buffer (pH 7.0)/acetonitrile mixture (2:3)

mobile phase delivery: density gradient was controlled by changing mixing ratio of mobile phase A and mobile phase B as follows.

TABLE 49

| time (min) after injection | mobile phase A (%) | mobile phase B (%) |
|---|---|---|
| 0 | 100 | 0 |
| 100 | 0 | 100 |
| 100.1 | 100 | 0 |
| 110 | 100 | 0 | measurement range of peak area: 100 min

Experimental Example 3

Measurement Method of Decomposed Product

The film-coated tablets of Examples 32, 34, 36, 38 and 40 were examined for the production of compound B decomposed product U-1 (relative retention time: about 0.75) and other decomposed products, before preservation (initial) and after preservation. The decomposed product was measured by extracting the tablets with water/MeCN mixture (1:3) by HPLC. The HPLC test conditions are as follows.

detector: ultraviolet absorption spectrophotometer (measurement wavelength: 230 nm)

column: CAPCELL PAK C18 MGII, 3 μm, 4.6 mm i.d.× 100 mm (manufactured by Shiseido Co., Ltd.)

column temperature: fixed temperature around 40° C.

mobile phase A: 0.03 mol/L sodium phosphate buffer (pH 7.0)/acetonitrile mixture (9:1)

mobile phase B: 0.03 mol/L sodium phosphate buffer (pH 7.0)/acetonitrile mixture (2:3)

mobile phase delivery: density gradient was controlled by changing mixing ratio of mobile phase A and mobile phase B in the same manner as in Table 49.

Experiment Results 4

The decomposed products before preservation and after preservation in closed bottle or open bottle at 40° C., 75% RH for 2 months were measured, and the results of total decomposed product and U-1 that remarkably increased in the absence of organic acid are shown in Table 50.

TABLE 50 decomposed product after preservation at 40° C., 75% RH for 2 months

| | | | | | before preservation | | after preservation | |
|---|---|---|---|---|---|---|---|---|
| sample | core tablet or film-coated tablet | compound B concentration (%) | organic acid concentration (%) | preservation state | total decomposed product (%) | decomposed product U-1 (%) | total decomposed product (%) | decomposed product U-1 (%) |
| sample 34 (comparison control) | film-coated tablet | 0.4 | 0 | closed glass bottle | 2.45 | 0.86 | 5.06 | 3.14 |
| | | | | open glass bottle | 2.45 | 0.86 | 5.93 | 3.51 |
| sample 36 | film-coated tablet | 0.4 | 2.3 | closed glass bottle | 2.25 | 0.79 | 4.56 | 2.01 |
| | | | | open glass bottle | 2.36 | 0.87 | 3.14 | 1.36 |
| sample 38 | film-coated tablet | 0.9 | 0.2 | closed glass bottle | 1.86 | 0.71 | 2.75 | 1.22 |
| | | | | open glass bottle | 1.86 | 0.71 | 2.37 | 1.10 |
| sample 40 | film-coated tablet | 0.4 | 2.3 | closed glass bottle | 2.33 | 0.81 | 5.18 | 2.11 |
| | | | | open glass bottle | 2.33 | 0.81 | 3.34 | 1.27 |
| sample 42 | film-coated tablet | 4.5 | 2.3 | closed glass bottle | 2.23 | 0.78 | 2.60 | 0.92 |
| | | | | open glass bottle | 2.23 | 0.78 | 2.18 | 0.81 |
| sample 44 | film-coated tablet | 17.9 | 2.3 | closed glass bottle | 2.25 | 0.80 | 2.40 | 0.90 |
| | | | | open glass bottle | 2.25 | 0.80 | 2.21 | 0.79 |

By the addition of an organic acid, irrespective of the preservation conditions and preservation state, an increase in the decomposed product U-1 was suppressed. Particularly, an increase in the decomposed product U-1, which strikingly increases in the absence of an organic acid, was remarkably suppressed.

U-1 was remarkably suppressed when fumaric acid was added during granulation by any of solution/dispersion addition including dissolving or dispersing fumaric acid in water and spraying the solution or dispersion, powder addition including addition of organic acid as a powder, and a combination of solution/dispersion addition and powder addition.

By the addition of an organic acid, a decomposed product suppressive effect was observed irrespective of the concentration of compound B.

Experimental Example 4

Measurement Method of Decomposed Product

The film-coated tablets of Comparative Example 6 and Examples 42 and 44 were examined for production of compound C decomposed product, before preservation (initial) and after preservation. The decomposed product U-2 (relative retention time: about 0.6), decomposed product U-3 (relative retention time: about 0.8) and other decomposed products were measured by extracting the tablets with 0.02 mol/L phosphate buffer (pH 7.0)/acetonitrile mixture (2:1) by HPLC. The HPLC test conditions are as follows.

detector: ultraviolet absorption spectrophotometer (measurement wavelength: 230 nm)

column: Zorbax Eclipse XDB-C18, 5 μm, 4.6 mm i.d.×150 mm (manufactured by Agilent)

column temperature: fixed temperature around 25° C.

mobile phase A: 0.02 mol/L phosphate buffer (pH 7.0)/acetonitrile mixture (19:1)

mobile phase B: acetonitrile/0.02 mol/L phosphate buffer (pH 7.0) mixture (3:2)

mobile phase delivery: density gradient was controlled by changing mixing ratio of mobile phase A and mobile phase B as follows.

TABLE 51

| time (min) after injection | mobile phase A (%) | mobile phase B (%) |
|---|---|---|
| 0 | 100 | 0 |
| 5 | 100 | 0 |
| 80 | 0 | 100 |
| 81 | 100 | 0 |
| 90 | 100 | 0 | measurement range of peak area: 80 min

Experiment Results 5

The decomposed products were measured before preservation and after preservation in a closed glass bottle at 40° C., 75% RH for 1 month, and the total decomposed product and the amounts of U-2 and U-3 that remarkably increased in the absence of organic acid are shown in Table 52.

TABLE 52 decomposed product after preservation at 40° C., 75% RH for 1 month

| sample | compound concentration (%) | organic acid concentration (%) | preservation state | before preservation | | | after preservation | | |
|---|---|---|---|---|---|---|---|---|---|
| | | | | total decomposed product (%) | decomposed product U-2 (%) | decomposed product U-3 (%) | total decomposed product (%) | decomposed product U-2 (%) | decomposed product U-3 (%) |
| sample 46 (comparison control) | 0.4 | 0 | closed glass bottle | 3.23 | 0.54 | 1.55 | 12.47 | 2.99 | 7.50 |
| | | | open glass bottle | 3.23 | 0.54 | 1.55 | 7.68 | 2.38 | 3.76 |
| sample 48 | 0.4 | 0.3 | closed glass bottle | 0.87 | 0.10 | 0.10 | 2.39 | 0.31 | 0.98 |
| sample 50 | 1.2 | 0.3 | closed glass bottle | 1.13 | 0.11 | 0.13 | 3.89 | 0.38 | 1.62 |
| | | | open glass bottle | 1.13 | 0.11 | 0.13 | 4.32 | 0.63 | 2.29 |

By the addition of an organic acid, an increase in the decomposed products U-2 and U-3 was suppressed irrespective of the preservation conditions and preservation state. Particularly, an increase in the decomposed products U-2 and U-3 that remarkably increase in the absence of organic acid was markedly suppressed.

By the addition of an organic acid, a decomposed product suppressive effect was observed irrespective of the concentration of compound C.

The solid preparation of the present invention containing a pharmaceutically active ingredient, titanium oxide, a plasticizer and a chain organic acid, which is the second invention of the present invention, was evaluated for the stability during light irradiation. The results are now explained by Examples 45-71 and Comparative Examples 7-9.

Example 45

Sample 51

A plain tablet (core tablet) containing 1-[5-(2-fluorophenyl)-1-(pyridin-3-ylsulfonyl)-1H-pyrrol-3-yl]-N-methyl-methanamine fumarate (hereinafter to be referred to as compound A) was produced as follows at the composition ratio shown in Table 53.

That is, compound A (24.340 g), mannitol (4350.2 g) and crystalline cellulose (540.1 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.1 g) to give a granulated powder. The obtained granulated powder (4568.1 g) was passed through a powermill (P-3, manufactured by Showa Kagaku Kikai Kosakusho) to give a sized powder (Batch 1).

Compound A (24.341 g), mannitol (4350.0 g) and crystalline cellulose (540.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.1 g) was passed through a powermill (P-3, manufactured by Showa Kagaku Kikai Kosakusho) to give a sized powder (Batch 2).

The sized powders (Batch 1 and Batch 2, 8460.0 g), croscarmellose sodium (450.0 g) and magnesium stearate (90.007 g) were placed in a tumbler mixer (TM-60S, manufactured by Showa Kagaku Kikai Kosakusho), and mixed to give a mixed powder. The mixed powder was tableted by a rotary tableting machine (AQUARIUS 08242L2JI, manufactured by Kikusui Seisakusho, Ltd.) using a 9 mmϕ punch to give plain tablets (core tablets, 300 mg per tablet).

TABLE 53 composition of plain tablet (core tablet) containing compound A (sample 51)

| composition | amount (mg) |
|---|---|
| 1) compound A* | 1.336 |
| 2) mannitol | 241.664 |
| 3) crystalline cellulose | 30 |
| 4) hydroxypropylcellulose | 9 |
| 5) croscarmellose sodium | 15 |
| 6) magnesium stearate | 3 |
| total | 300.0 |

*Where necessary, the content was amended using mannitol as an adjustment component.

Example 46

Sample 52

The plain tablets (core tablets) obtained in Example 45 (sample 51, 30.0 g) were placed in a film coating machine (DRC-200, manufactured by POWREX CORPORATION), and film-coated tablets (about 312 mg per tablet) were obtained while spraying a film coating solution (65.9 g) having the composition ratio shown in Table 54. The obtained film-coated tablets were arranged on a plastic petri dish (45 sample cup, manufactured by Shinwa Kagaku), and exposed to xenon light (1200000 Lux/hr) by a xenon fade meter (SX75, manufactured by Suga Test Instruments).

TABLE 54

Composition of aqueous film coating solution

| composition | amount (mg) |
|---|---|
| 1) hypromellose | 8.8 |
| 2) macrogol 6000 | 2 |
| 3) titanium oxide | 1 |
| 4) diiron trioxide | 0.2 |
| 5) purified water | 108 |
| total | 120.0 |

Example 47

Sample 53

The plain tablets (core tablets) obtained in Example 45 (sample 51, 30.0 g) were placed in a film coating machine (DRC-200, manufactured by POWREX CORPORATION), and film-coated tablets (about 312 mg per tablet) were obtained while spraying a film coating solution (66.2 g) having the composition ratio shown in Table 55. The obtained film-coated tablets were arranged on a plastic petri dish (45 sample cup, manufactured by Shinwa Kagaku), and samples shielded with aluminum foil and non-shielded samples were exposed to xenon light (1200000 Lux/hr).

TABLE 55

| Composition of aqueous film coating solution | |
|---|---|
| composition | amount (mg) |
| 1) hypromellose | 8.595 |
| 2) macrogol 6000 | 1.953 |
| 3) titanium oxide | 0.977 |
| 4) diiron trioxide | 0.195 |
| 5) fumaric acid | 0.28 |
| 6) purified water | 108 |
| total | 120.0 |

Example 48

Sample 54

The plain tablets (core tablets) obtained in Example 45 (sample 51, 30.0 g) were placed in a film coating machine (DRC-200, manufactured by POWREX CORPORATION), and film-coated tablets (about 312 mg per tablet) were obtained while spraying a film coating solution (75.1 g) having the composition ratio shown in Table 56. The obtained film-coated tablets were arranged on a plastic petri dish (45 sample cup, manufactured by Shinwa Kagaku), and exposed to xenon light (1200000 Lux/hr) by a xenon fade meter (SX75, manufactured by Suga Test Instruments).

TABLE 56

| Composition of aqueous film coating solution | |
|---|---|
| composition | amount (mg) |
| 1) hypromellose | 8.389 |
| 2) macrogol 6000 | 1.907 |
| 3) titanium oxide | 0.953 |
| 4) diiron trioxide | 0.191 |
| 5) fumaric acid | 0.56 |
| 6) purified water | 108 |
| total | 120.0 |

Example 49

Sample 55

A plain tablet (core tablet) containing compound A was produced as follows at the composition ratio shown in Table 57.

That is, compound A (2.4074 g), mannitol (432.3 g), crystalline cellulose (54.0 g) and fumaric acid (2.70 g) were placed in a fluidized bed dryer granulator (LAB-1, manufactured by POWREX CORPORATION), and the mixture was preheated and mixed. The mixture was granulated while spraying an aqueous solution (270.0 g) of hydroxypropylcellulose (16.2 g) to give a granulated powder. The obtained granulated powder was passed through a 16M (1000 μm) sieve to give a sized powder. Croscarmellose sodium (22.50 g) and magnesium stearate (4.5011 g) were added to the sized powder (423.0 g), and mixed to give a mixed powder. The mixed powder was tableted by a rotary tableting machine (COLLECT 19K, manufactured by Kikusui Seisakusho, Ltd.) using a 9 mmφ punch to give plain tablets (core tablets, 300 mg per tablet).

TABLE 57

| composition of plain tablet (core tablet) containing compound A (sample 55) | |
|---|---|
| composition | amount (mg) |
| 1) compound A* | 1.336 |
| 2) mannitol | 240.164 |
| 3) crystalline cellulose | 30 |
| 4) hydroxypropylcellulose | 9 |
| 5) fumaric acid | 1.5 |
| 6) croscarmellose sodium | 15 |
| 7) magnesium stearate | 3 |
| total | 300.0 |

*Where necessary, the content was amended using mannitol as an adjustment component.

Example 50

Sample 56

A plain tablet (core tablet) containing compound A was produced as follows at the composition ratio shown in Table 58.

That is, compound A (2.4080 g), mannitol (429.6 g), crystalline cellulose (54.0 g) and fumaric acid (5.40 g) were placed in a fluidized bed dryer granulator (LAB-1, manufactured by POWREX CORPORATION), and the mixture was preheated and mixed. The mixture was granulated while spraying an aqueous solution (270.0 g) of hydroxypropylcellulose (16.2 g) to give a granulated powder. The obtained granulated powder was passed through a 16M (1000 μm) sieve to give a sized powder. Croscarmellose sodium (22.50 g) and magnesium stearate (4.5012 g) were added to the sized powder (423.0 g), and mixed to give a mixed powder. The mixed powder was tableted by a rotary tableting machine (COLLECT 19K, manufactured by Kikusui Seisakusho, Ltd.) using a 9 mmφ punch to give plain tablets (core tablets, 300 mg per tablet).

TABLE 58

| composition of plain tablet (core tablet) containing compound A (sample 56) | |
|---|---|
| composition | amount (mg) |
| 1) compound A* | 1.336 |
| 2) mannitol | 238.664 |
| 3) crystalline cellulose | 30 |
| 4) hydroxypropylcellulose | 9 |
| 5) fumaric acid | 3 |
| 6) croscarmellose sodium | 15 |
| 7) magnesium stearate | 3 |
| total | 300.0 |

*Where necessary, the content was amended using mannitol as an adjustment component.

Example 51

Sample 57

A plain tablet (core tablet) containing compound A was produced as follows at the composition ratio shown in Table 59.

That is, compound A (2.4095 g), mannitol (422.4 g), crystalline cellulose (54.0 g) and fumaric acid (12.60 g) were placed in a fluidized bed dryer granulator (LAB-1, manufactured by POWREX CORPORATION), and the mixture was preheated and mixed. The mixture was granulated while spraying an aqueous solution (270.0 g) of hydroxypropylcellulose (16.2 g) to give a granulated powder. The obtained granulated powder was passed through a 16M (1000 μm) sieve to give a sized powder. Croscarmellose sodium (22.50 g) and magnesium stearate (4.5017 g) were added to the sized powder (423.0 g), and mixed to give a mixed powder. The mixed powder was tableted by a rotary tableting machine (COLLECT 19K, manufactured by Kikusui Seisakusho, Ltd.) using a 9 mmϕ punch to give plain tablets (core tablets, 300 mg per tablet).

TABLE 59 composition of plain tablet (core tablet) containing compound A (sample 57)

| composition | amount (mg) |
|---|---|
| 1) compound A* | 1.336 |
| 2) mannitol | 234.664 |
| 3) crystalline cellulose | 30 |
| 4) hydroxypropylcellulose | 9 |
| 5) fumaric acid | 7 |
| 6) croscarmellose sodium | 15 |
| 7) magnesium stearate | 3 |
| total | 300.0 |

*Where necessary, the content was amended using mannitol as an adjustment component.

Example 52

Sample 58

The plain tablets (core tablets) obtained in Example 49 (sample 55, 100.0 g) were placed in a film coating machine (DRC-200, manufactured by POWREX CORPORATION), and film-coated tablets (about 312 mg per tablet) were obtained while spraying a film coating solution (49.2 g) having the composition ratio shown in Table 60. The obtained film-coated tablets were arranged on a plastic petri dish (45 sample cup, manufactured by Shinwa Kagaku), and exposed to xenon light (1200000 Lux/hr) by a xenon fade meter (SX75, manufactured by Suga Test Instruments).

TABLE 60

Composition of aqueous film coating solution

| composition | amount (mg) |
|---|---|
| 1) hypromellose | 8.8 |
| 2) macrogol 6000 | 2 |
| 3) titanium oxide | 1 |
| 4) diiron trioxide | 0.2 |
| 5) purified water | 108 |
| total | 120.0 |

Example 53

Sample 59

The plain tablets (core tablets) obtained in Example 50 (sample 56, 100.0 g) were placed in a film coating machine (DRC-200, manufactured by POWREX CORPORATION), and film-coated tablets (about 312 mg per tablet) were obtained while spraying a film coating solution (61.4 g) having the composition ratio shown in Table 61. The obtained film-coated tablets were arranged on a plastic petri dish (45 sample cup, manufactured by Shinwa Kagaku), and exposed to xenon light (1200000 Lux/hr) by a xenon fade meter (SX75, manufactured by Suga Test Instruments).

TABLE 61

Composition of aqueous film coating solution

| composition | amount (mg) |
|---|---|
| 1) hypromellose | 8.8 |
| 2) macrogol 6000 | 2 |
| 3) titanium oxide | 1 |
| 4) diiron trioxide | 0.2 |
| 5) purified water | 108 |
| total | 120.0 |

Example 54

Sample 60

The plain tablets (core tablets) obtained in Example 51 (sample 57, 100.0 g) were placed in a film coating machine (DRC-200, manufactured by POWREX CORPORATION), and film-coated tablets (about 312 mg per tablet) were obtained while spraying a film coating solution (59.5 g) having the composition ratio shown in Table 62. The obtained film-coated tablets were arranged on a plastic petri dish (45 sample cup, manufactured by Shinwa Kagaku), and exposed to xenon light (1200000 Lux/hr) by a xenon fade meter (SX75, manufactured by Suga Test Instruments).

TABLE 62

Composition of aqueous film coating solution

| composition | amount (mg) |
|---|---|
| 1) hypromellose | 8.8 |
| 2) macrogol 6000 | 2 |
| 3) titanium oxide | 1 |
| 4) diiron trioxide | 0.2 |
| 5) purified water | 108 |
| total | 120.0 |

Comparative Example 7

Sample 61

A plain tablet (core tablet) containing compound A was produced as follows at the composition ratio shown in Table 63.

That is, compound A (24.491 g), mannitol (4350.0 g) and crystalline cellulose (540.0 g) were placed in a fluidized bed dryer granulator (FD-5S, manufactured by POWREX CORPORATION), and the mixture was preheated and mixed. The mixture was granulated while spraying an aqueous solution (2700.0 g) of hydroxypropylcellulose (162.0 g) to give a granulated powder. The obtained granulated powder (4568.0 g) was passed through a powermill (P-3, manufactured by Showa Kagaku Kikai Kosakusho) to give a sized powder. The sized powder (4230.0 g), croscarmellose sodium (225.0 g) and magnesium stearate (45.007 g) were placed in a tumbler mixer (TM-15S, manufactured by Showa Kagaku Kikai Kosakusho), and mixed to give a mixed powder. The mixed powder was tableted by a rotary tableting machine (COLLECT 12HUK, manufactured by Kikusui Seisakusho, Ltd.) using a 9 mmϕ punch to give plain tablets (core tablets, 300 mg per tablet).

TABLE 63 composition of plain tablet (core tablet) containing compound A (sample 61)

| composition | amount (mg) |
| --- | --- |
| 1) compound A* | 1.336 |
| 2) mannitol | 241.664 |
| 3) crystalline cellulose | 30 |
| 4) hydroxypropylcellulose | 9 |
| 5) croscarmellose sodium | 15 |
| 6) magnesium stearate | 3 |
| total | 300.0 |

*Where necessary, the content was amended using mannitol as an adjustment component.

Comparative Example 8

Sample 62

The plain tablets (core tablets) obtained in Comparative Example 7 (sample 61, 3300.0 g) were placed in a film coating machine (DRC-500, manufactured by POWREX CORPORATION), and film-coated tablets (about 312 mg per tablet) were obtained while spraying a film coating solution (1372.0 g) having the composition ratio shown in Table 64. The obtained film-coated tablets were arranged on a plastic petri dish (45 sample cup, manufactured by Shinwa Kagaku), and exposed to xenon light (1200000 Lux/hr) by a xenon fade meter (SX75, manufactured by Suga Test Instruments).

TABLE 64

Composition of aqueous film coating solution

| composition | amount (mg) |
| --- | --- |
| 1) hypromellose | 10.8 |
| 2) titanium oxide | 1 |
| 3) diiron trioxide | 0.2 |
| 4) purified water | 108 |
| total | 120.0 |

Example 55

Sample 63

A plain tablet (core tablet) containing compound A is produced as follows at the composition ratio shown in Table 65.
That is, compound A (641.28 g), mannitol (3503.52 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 6.5 mmϕ punch to give plain tablets (core tablets, 110 mg per tablet). The obtained plain tablets (core tablets, 3300.0 g) are placed in a film coating machine (DRC-500, manufactured by POWREX CORPORATION), and film-coated tablets (about 114.4 mg per tablet) are obtained while spraying a film coating solution (1380.0 g) having the composition ratio shown in Table 66.

TABLE 65 composition of plain tablet (core tablet) containing compound A

| composition | amount (mg) |
| --- | --- |
| 1) compound A | 13.36 |
| 2) mannitol | 72.99 |
| 3) crystalline cellulose | 11 |
| 4) hydroxypropylcellulose | 3.3 |
| 5) fumaric acid | 2.75 |
| 6) croscarmellose sodium | 5.5 |
| 7) magnesium stearate | 1.1 |
| total | 110.0 |

TABLE 66 composition of aqueous film coating solution.

| composition | amount (mg) |
| --- | --- |
| 1) hypromellose | 6.6 |
| 2) macrogol 6000 | 1.5 |
| 3) titanium oxide | 0.75 |
| 4) yellow ferric oxide | 0.075 |
| 5) diiron trioxide | 0.075 |
| 6) purified water | 81 |
| total | 90.0 |

Example 56

Sample 64

A plain tablet (core tablet) containing compound A is produced as follows at the composition ratio shown in Table 67.
That is, compound A (641.28 g), mannitol (3503.52 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 7 mmϕ punch to give plain tablets (core tablets, 165 mg per tablet). The obtained plain tablets (core tablets, 3300.0 g) are placed in a film coating machine (DRC-500, manufactured by POWREX CORPORATION), and film-coated tablets (about 171.6 mg per tablet) are obtained while spraying a film coating solution (1380.0 g) having the composition ratio shown in Table 66.

TABLE 67 composition of plain tablet (core tablet) containing compound A

| composition | amount (mg) |
|---|---|
| 1) compound A | 20.04 |
| 2) mannitol | 109.485 |
| 3) crystalline cellulose | 16.5 |
| 4) hydroxypropylcellulose | 4.95 |
| 5) fumaric acid | 4.125 |
| 6) croscarmellose sodium | 8.25 |
| 7) magnesium stearate | 1.65 |
| total | 165.0 |

Example 57

Sample 65

A plain tablet (core tablet) containing compound A is produced as follows at the composition ratio shown in Table 68.

That is, compound A (641.28 g), mannitol (3503.52 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 9.5 mmϕ punch to give plain tablets (core tablets, 330 mg per tablet). The obtained plain tablets (core tablets, 3300.0 g) is placed in a film coating machine (DRC-500, manufactured by POWREX CORPORATION), and film-coated tablets (about 343.2 mg per tablet) is obtained while spraying a film coating solution (1380.0 g) having the composition ratio shown in Table 66.

TABLE 68 composition of plain tablet (core tablet) containing compound A

| composition | amount (mg) |
|---|---|
| 1) compound A | 40.08 |
| 2) mannitol | 218.97 |
| 3) crystalline cellulose | 33 |
| 4) hydroxypropylcellulose | 9.9 |
| 5) fumaric acid | 8.25 |
| 6) croscarmellose sodium | 16.5 |
| 7) magnesium stearate | 3.3 |
| total | 330.0 |

Example 58

Sample 66

A plain tablet (core tablet) containing compound A is produced as follows at the composition ratio shown in Table 69.

That is, compound A (641.28 g), mannitol (3503.52 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 14×8 mmϕ punch to give plain tablets (core tablets, 440 mg per tablet). The obtained plain tablets (core tablets, 3300.0 g) are placed in a film coating machine (DRC-500, manufactured by POWREX CORPORATION), and film-coated tablets (about 457.6 mg per tablet) are obtained while spraying a film coating solution (1380.0 g) having the composition ratio shown in Table 66.

TABLE 69 composition of plain tablet (core tablet) containing compound A

| composition | amount (mg) |
|---|---|
| 1) compound A | 53.44 |
| 2) mannitol | 291.96 |
| 3) crystalline cellulose | 44 |
| 4) hydroxypropylcellulose | 13.2 |
| 5) fumaric acid | 11 |
| 6) croscarmellose sodium | 22 |
| 7) magnesium stearate | 4.4 |
| total | 440 |

Example 59

Sample 67

A plain tablet (core tablet) containing compound A is produced as follows at the composition ratio shown in Table 70.

That is, compound A (881.76 g), mannitol (3263.04 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 6.5 mmϕ punch to give plain tablets (core tablets, 120 mg per tablet). The obtained plain tablets (core tablets, 3300.0 g) are placed in a film coating machine (DRC-500, manufactured by POWREX CORPORATION), and film-coated tablets (about 124.8 mg per tablet) are obtained while spraying a film coating solution (1380 g) having the composition ratio shown in Table 66.

TABLE 70 composition of plain tablet (core tablet) containing compound A

| composition | amount (mg) |
| --- | --- |
| 1) compound A | 20.04 |
| 2) mannitol | 74.16 |
| 3) crystalline cellulose | 12 |
| 4) hydroxypropylcellulose | 3.6 |
| 5) fumaric acid | 3 |
| 6) croscarmellose sodium | 6 |
| 7) magnesium stearate | 1.2 |
| total | 120 |

Example 60

Sample 68

A plain tablet (core tablet) containing compound A is produced as follows at the composition ratio shown in Table 71.

That is, compound A (881.76 g), mannitol (3263.04 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 7 mmφ punch to give plain tablets (core tablets, 160 mg per tablet). The obtained plain tablets (core tablets, 3300.0 g) are placed in a film coating machine (DRC-500, manufactured by POWREX CORPORATION), and film-coated tablets (about 166.4 mg per tablet) are obtained while spraying a film coating solution (1380 g) having the composition ratio shown in Table 66.

TABLE 71 composition of plain tablet (core tablet) containing compound A

| composition | amount (mg) |
| --- | --- |
| 1) compound A | 26.72 |
| 2) mannitol | 98.88 |
| 3) crystalline cellulose | 16 |
| 4) hydroxypropylcellulose | 4.8 |
| 5) fumaric acid | 4 |
| 6) croscarmellose sodium | 8 |
| 7) magnesium stearate | 1.6 |
| total | 160 |

Example 61

Sample 69

A plain tablet (core tablet) containing compound A is produced as follows at the composition ratio shown in Table 72.

That is, compound A (881.76 g), mannitol (3263.04 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 8 mmφ punch to give plain tablets (core tablets, 240 mg per tablet). The obtained plain tablets (core tablets, 3300.0 g) are placed in a film coating machine (DRC-500, manufactured by POWREX CORPORATION), and film-coated tablets (about 249.6 mg per tablet) are obtained while spraying a film coating solution (1380 g) having the composition ratio shown in Table 66.

TABLE 72 composition of plain tablet (core tablet) containing compound A

| composition | amount (mg) |
| --- | --- |
| 1) compound A | 40.08 |
| 2) mannitol | 148.32 |
| 3) crystalline cellulose | 24 |
| 4) hydroxypropylcellulose | 7.2 |
| 5) fumaric acid | 6 |
| 6) croscarmellose sodium | 12 |
| 7) magnesium stearate | 2.4 |
| total | 240 |

Example 62

Sample 70

A plain tablet (core tablet) containing compound A is produced as follows at the composition ratio shown in Table 73.

That is, compound A (881.76 g), mannitol (3263.04 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 9.5 mmφ punch to give plain tablets (core tablets, 320 mg per tablet). The obtained plain tablets (core tablets, 3300.0 g) are placed in a film coating machine (DRC-500, manufactured by POWREX CORPORATION), and film-coated tablets (about 332.8 mg per tablet) are obtained while spraying a film coating solution (1380 g) having the composition ratio shown in Table 66.

TABLE 73 composition of plain tablet (core tablet) containing compound A

| composition | amount (mg) |
| --- | --- |
| 1) compound A | 53.44 |
| 2) mannitol | 197.76 |
| 3) crystalline cellulose | 32 |
| 4) hydroxypropylcellulose | 9.6 |
| 5) fumaric acid | 8 |
| 6) croscarmellose sodium | 16 |
| 7) magnesium stearate | 3.2 |
| total | 320 |

Example 63

Sample 71

A plain tablet (core tablet) containing compound A is produced as follows at the composition ratio shown in Table 74.

That is, compound A (961.92 g), mannitol (3182.88 g), fumaric acid (132.0 g) and crystalline cellulose (528.0 g) are placed in a fluidized bed dryer granulator (FD-5S, manufactured by POWREX CORPORATION), and the mixture is preheated and mixed. The mixture is granulated while spraying an aqueous solution (2640.0 g) of hydroxypropylcellulose (158.4 g) to give a granulated powder. The obtained granulated powder (4653.0 g) is passed through a powermill (P-3, manufactured by Showa Kagaku Kikai Kosakusho) to give a sized powder. The sized powder (4342.8 g), croscarmellose sodium (231.0 g) and magnesium stearate (46.2 g) are placed in a tumbler mixer (TM-15S, manufactured by Showa Kagaku Kikai Kosakusho), and mixed to give a mixed powder. The mixed powder is tableted by a rotary tableting machine (COLLECT 12HUK, manufactured by Kikusui Seisakusho, Ltd.) using a 8 mmϕ punch to give plain tablets (core tablets, 220 mg per tablet). The obtained plain tablets (core tablets, 3300.0 g) are placed in a film coating machine (DRC-500, manufactured by POWREX CORPORATION), and film-coated tablets (about 228.8 mg per tablet) are obtained while spraying a film coating solution (1380 g) having the composition ratio shown in Table 66.

TABLE 74 composition of plain tablet (core tablet) containing compound A

| composition | amount (mg) |
| --- | --- |
| 1) compound A | 40.08 |
| 2) mannitol | 132.62 |
| 3) crystalline cellulose | 22 |
| 4) hydroxypropylcellulose | 6.6 |
| 5) fumaric acid | 5.5 |
| 6) croscarmellose sodium | 11 |
| 7) magnesium stearate | 2.2 |
| total | 220 |

Example 64

Sample 72

The plain tablets (core tablets) obtained in Example 12 (sample 14, 3300.0 g) were placed in a film coating machine (DRC-500, manufactured by POWREX CORPORATION), and film-coated tablets (about 229 mg per tablet) were obtained while spraying a film coating solution (1480.9 g) having the composition ratio shown in Table 29. The obtained film-coated tablets were exposed to xenon light (1200000 Lux/hr) by a fade meter (SX75, manufactured by Suga Test Instruments).

Example 65

Sample 73

The plain tablets (core tablets) obtained in Example 13 (sample 15, 3300.0 g) were placed in a film coating machine (DRC-500, manufactured by POWREX CORPORATION), and film-coated tablets (about 229 mg per tablet) were obtained while spraying a film coating solution (1501.0 g) having the composition ratio shown in Table 30. The obtained film-coated tablets were exposed to xenon light (1200000 Lux/hr) by a fade meter (SX75, manufactured by Suga Test Instruments).

Example 66

Sample 74

The plain tablets (core tablets) obtained in Example 14 (sample 16, 3300.0 g) were placed in a film coating machine (DRC-500, manufactured by POWREX CORPORATION), and film-coated tablets (about 229 mg per tablet) were obtained while spraying a film coating solution (1514.0 g) having the composition ratio shown in Table 31. The obtained film-coated tablets were exposed to xenon light (1200000 Lux/hr) by a fade meter (SX75, manufactured by Suga Test Instruments).

Example 67

Sample 75

The plain tablets (core tablets) obtained in Example 15 (sample 17, 3300.0 g) were placed in a film coating machine (DRC-500, manufactured by POWREX CORPORATION), and film-coated tablets (about 229 mg per tablet) were obtained while spraying a film coating solution (1374.0 g) having the composition ratio shown in Table 32. The obtained film-coated tablets were exposed to xenon light (1200000 Lux/hr) by a fade meter (SX75, manufactured by Suga Test Instruments).

Comparative Example 9

Sample 76

The plain tablets (core tablets) obtained in Comparative Example 3 (sample 33, 200.0 g) were placed in a film coating machine (DRC-200, manufactured by POWREX CORPORATION), and film-coated tablets (about 312 mg per tablet) were obtained while spraying a film coating solution (96.8 g) having the composition ratio shown in Table 34. The obtained film-coated tablets were exposed to xenon light (1200000 Lux/hr) by a fade meter (SX75, manufactured by Suga Test Instruments).

Example 68

Sample 77

The plain tablets (core tablets) obtained in Example 31 (sample 35, 3300.0 g) were placed in a film coating machine (DRC-500, manufactured by POWREX CORPORATION), and film-coated tablets (about 312 mg per tablet) were obtained while spraying a film coating solution (1432.0 g) having the composition ratio shown in Table 34. The obtained film-coated tablets were exposed to xenon light (1200000 Lux/hr) by a fade meter (SX75, manufactured by Suga Test Instruments).

Example 69

Sample 78

The plain tablets (core tablets) obtained in Example 35 (sample 39, 3300.0 g) were placed in a film coating machine (DRC-500, manufactured by POWREX CORPORATION), and film-coated tablets (about 156 mg per tablet) were obtained while spraying a film coating solution (1470.0 g) having the composition ratio shown in Table 37. The obtained film-coated tablets were exposed to xenon light (1200000 Lux/hr) by a fade meter (SX75, manufactured by Suga Test Instruments).

Example 70

Sample 79

The plain tablets (core tablets) obtained in Example 37 (sample 41, 3300.0 g) were placed in a film coating machine (DRC-500, manufactured by POWREX CORPORATION), and film-coated tablets (about 312 mg per tablet) were obtained while spraying a film coating solution (1425.0 g) having the composition ratio shown in Table 37. The obtained film-coated tablets were exposed to xenon light (1200000 Lux/hr) by a fade meter (SX75, manufactured by Suga Test Instruments).

Example 71

Sample 80

The plain tablets (core tablets) obtained in Example 39 (sample 43, 3300.0 g) were placed in a film coating machine (DRC-500, manufactured by POWREX CORPORATION), and film-coated tablets (about 312 mg per tablet) were obtained while spraying a film coating solution (1417.2 g) having the composition ratio shown in Table 37. The obtained film-coated tablets were exposed to xenon light (1200000 Lux/hr) by a fade meter (SX75, manufactured by Suga Test Instruments).

Experimental Example 5

Measurement Method of Decomposed Product

The film-coated tablets of Examples 46-48, Examples 52-54, Examples 64-67 and Comparative Example 8 were examined for the production of compound A decomposed product, before xenon light irradiation and after xenon light irradiation. The decomposed product U-6 was measured by extracting the tablets with 0.05 mol/L phosphoric acid/MeCN mixture (19:1) or water/MeCN mixture (19:1) by HPLC. The HPLC test conditions are as follows.

detector: ultraviolet absorption spectrophotometer (measurement wavelength: 230 nm)

column: CAPCELL PAK C18 MGII, 3 μm, 4.6 mm i.d.× 150 mm (manufactured by Shiseido Co., Ltd.)

column temperature: fixed temperature around 25° C.

mobile phase A: 0.05 mol/L sodium phosphate buffer (pH 6.0)/acetonitrile mixture (95:5)

mobile phase B: 0.05 mol/L sodium phosphate buffer (pH 6.0)/acetonitrile mixture (40:60)

mobile phase delivery: density gradient was controlled by changing mixing ratio of mobile phase A and mobile phase B as follows.

TABLE 75

| time (min) after injection | mobile phase A (%) | mobile phase B (%) |
| --- | --- | --- |
| 0 | 100 | 0 |
| 10 | 80 | 20 |
| 60 | 70 | 30 |
| 110 | 0 | 100 |
| 110.1 | 100 | 0 |
| 120 | 100 | 0 | measurement range of peak area: 110 min

Experiment Results 6

The compound A decomposed product U-6 (relative retention time: about 0.7) and other decomposed products were measured before xenon light irradiation and after xenon light irradiation, and the results of the total decomposed products are shown in Table 76.

TABLE 76

| sample | PEG addition to film part | compound concentration (%) | organic acid concentration (%) | | total decomposed product (%) | |
| --- | --- | --- | --- | --- | --- | --- |
| | | | core tablet part | film part | before xenon light irradiation | after xenon light irradiation |
| sample 52 | added | 0.4 | 0 | 0 | 0.70 | 1.59 |
| sample 53 | added | 0.4 | 0 | 2.3 | 0.71 | 1.05 |
| sample 54 | added | 0.4 | 0 | 4.7 | 0.85 | 0.84 |
| sample 58 | added | 0.4 | 0.5 | 0 | 0.84 | 1.15 |
| sample 59 | added | 0.4 | 1.0 | 0 | 0.85 | 1.03 |
| sample 60 | added | 0.4 | 2.3 | 0 | 0.83 | 0.92 |
| sample 72 | added | 1.5 | 2.5 | 0 | 0.74 | 0.76 |

TABLE 76-continued

| sample | PEG addition to film part | compound concentration (%) | organic acid concentration (%) core tablet part | film part | total decomposed product (%) before xenon light irradiation | after xenon light irradiation |
|---|---|---|---|---|---|---|
| sample 73 | added | 3.0 | 2.5 | 0 | 0.71 | 0.73 |
| sample 74 | added | 6.1 | 2.5 | 0 | 0.79 | 0.74 |
| sample 75 | added | 12.1 | 2.5 | 0 | 0.68 | 0.70 |
| sample 62 Comparative Example | not added | 0.4 | 0 | 0 | 1.00 | 1.12 |

* organic acid concentration (%) of core tablet part = (organic acid mass contained in core tablet part/core tablet mass) × 100
* organic acid concentration (%) of film part = (organic acid mass contained in film part/film mass) × 100
* compound concentration (%) = (added compound weight/core tablet weight) × 100

Even when PEG was added to film coating component, production of a decomposed product after light irradiation was suppressed by the addition of an organic acid.

Even when organic acid was added to the core tablet part or the film part, a decomposed product suppressive effect was observed. When added to the core tablet part, a remarkable suppression was observed with 2.3% or above. When added to the film part, a remarkable suppression was observed with 4.7% or above.

Even when PEG was added to a film coating component, stabilization was achieved to a level equal to or higher than the absence of PEG by the addition of an organic acid.

Since the production of a decomposed product can be suppressed by the addition of an organic acid, suppression of change in the appearance after light irradiation is sufficiently predicted. Hence, a high quality pharmaceutical composition superior in light-stability can be provided.

Experimental Example 6

Measurement Method of Decomposed Product

The film-coated tablet (sample 76) obtained in Comparative Example 9 was examined for the production of compound B total decomposed product before xenon light irradiation and after xenon light irradiation. The decomposed product was measured by extracting the tablet with water/MeCN mixture (1:3) by HPLC. The HPLC test conditions are as follows.

detector: ultraviolet absorption spectrophotometer (measurement wavelength: 230 nm)
column: CAPCELL PAK C18 MGII, 3 μm, 4.6 mm i.d.× 100 mm (manufactured by Shiseido Co., Ltd.)
column temperature: fixed temperature around 40° C.
mobile phase A: 0.05 mol/L sodium phosphate buffer (pH 7.0)/acetonitrile mixture (9:1)
mobile phase B: 0.05 mol/L sodium phosphate buffer (pH 7.0)/acetonitrile mixture (2:3)
mobile phase delivery: density gradient was controlled by changing mixing ratio of mobile phase A and mobile phase B as follows.

TABLE 77

| time (min) after injection | mobile phase A (%) | mobile phase B (%) |
|---|---|---|
| 0 | 100 | 0 |
| 100 | 0 | 100 |
| 100.1 | 100 | 0 |
| 110 | 100 | 0 | measurement range of peak area: 100 min

Experimental Example 7

Measurement Method of Decomposed Product

The film-coated tablets obtained Examples 68-71 (samples 77, 78, 79 and 80) were examined for the production of compound B total decomposed product before xenon light irradiation and after xenon light irradiation. The decomposed products were measured by extracting the tablets with water/MeCN mixture (1:3) by HPLC. The HPLC test conditions are as follows.

detector: ultraviolet absorption spectrophotometer (measurement wavelength: 230 nm)
column: CAPCELL PAK C18 MGII, 3 μm, 4.6 mm i.d.× 100 mm (manufactured by Shiseido Co., Ltd.)
column temperature: fixed temperature around 40° C.
mobile phase A: 0.03 mol/L sodium phosphate buffer (pH 7.0)/acetonitrile mixture (9:1)
mobile phase B: 0.03 mol/L sodium phosphate buffer (pH 7.0)/acetonitrile mixture (2:3)
mobile phase delivery: density gradient was controlled by changing mixing ratio of mobile phase A and mobile phase B as follows.

TABLE 78

| time (min) after injection | mobile phase A (%) | mobile phase B (%) |
|---|---|---|
| 0 | 100 | 0 |
| 100 | 0 | 100 |
| 100.1 | 100 | 0 |
| 110 | 100 | 0 | measurement range of peak area: 100 min

Experiment Results 7

The decomposed products of film-coated tablets were measured before xenon light irradiation and after xenon light irradiation, and the results of the total decomposed products are shown in Table 79.

TABLE 79

| | | | before organic acid concentration (%) | | | |
|---|---|---|---|---|---|---|
| sample | core tablet or film-coated tablet | compound concentration (%) | core tablet part | film part | before preservation total decomposed product (%) | after preservation total decomposed product (%) |
| sample 76 (comparison control) | film-coated tablet | 0.4 | 0 | 0 | 2.45 | 2.87 |
| sample 77 | film-coated tablet | 0.4 | 2.3 | 0 | 2.36 | 2.65 |
| sample 78 | film-coated tablet | 0.4 | 2.3 | 0 | 2.33 | 2.55 |
| sample 79 | film-coated tablet | 4.5 | 2.3 | 0 | 2.23 | 2.24 |
| sample 80 | film-coated tablet | 17.9 | 2.3 | 0 | 2.25 | 2.29 |

Since the production of a decomposed product can be suppressed by the addition of an organic acid, suppression of change in the appearance after light irradiation is sufficiently predicted. Hence, a high quality pharmaceutical composition superior in light-stability can be provided.

INDUSTRIAL APPLICABILITY

According to the first invention of the present invention, a stabilized pharmaceutical composition comprising a nonpeptidic pharmaceutically active ingredient having a primary or secondary amino group is provided. To be specific, since development of a decomposed product of the pharmaceutically active ingredient (nonpeptidic one having a primary or secondary amino group) in the pharmaceutical composition is suppressed, a more stable pharmaceutical composition is provided. According to the present invention, moreover, since development of a decomposed product of the pharmaceutically active ingredient is suppressed regardless of being in a closed bottle/open bottle, a pharmaceutical composition also superior in the preservation stability can be provided. In addition, according to the second invention of the present invention, a solid preparation improved in the stability of a pharmaceutically active ingredient to light irradiation is provided. To be specific, a solid preparation stable to light irradiation can be provided by, when the pharmaceutically active ingredient contained in the solid preparation is exposed to light, shielding the light and suppressing an increase in a decomposed product.

This application is based on a patent application No. 2008-194219 filed in Japan, the contents of which are incorporated in full herein by this reference.

The invention claimed is:

1. A stabilized pharmaceutical composition comprising a nonpeptidic pharmaceutically active ingredient having a primary or secondary amino group, an excipient and an acidic compound, wherein the nonpeptidic pharmaceutically active ingredient is
1-{5-(2-fluorophenyl)-1-[pyridin-3-ylsulfonyl)-1H-pyrrol-3-yl]-N-methylmethanamine) or a salt thereof, (N-methyl-1-[5-(2-methylphenyl)-1-(pyridin-3-ylsulfonyl)-1H-pyrrol-3-yl]methanamine) or a salt thereof, or (1-[4-fluoro-5-(2-fluoropyridin-3-yl)-1-(pyridin-3-ylsulfonyl)-1H-pyrrol-3-yl]-N-methylmethanamine) or a slat thereof;

wherein the excipient has pH 4.5 or above when dissolved or dispersed in water; and wherein the acidic compound is a fumaric acid or a salt thereof.

2. The pharmaceutical composition of claim 1, wherein the nonpeptidic pharmaceutically active ingredient has a pKa value higher than that of the fumaric acid or a salt thereof.

3. The pharmaceutical composition of claim 1, wherein the nonpeptidic pharmaceutically active ingredient is an organic acid salt.

4. The pharmaceutical composition of claim 1, wherein the excipient is any one kind or more selected from the group consisting of mannitol, croscarmellose sodium, hydroxypropylcellulose, hydroxypropylmethylcellulose, polyethylene glycol, polyvinylpyrrolidone, crystalline cellulose, lactose, sucrose, starch, cornstarch, titanium oxide ($TiO_2$) and light anhydrous silicic acid.

5. The pharmaceutical composition of claim 1, wherein the nonpeptidic pharmaceutically active ingredient is a salt with an unsaturated carboxylic acid.

6. The pharmaceutical composition of claim 1, which is a solid preparation.

7. The pharmaceutical composition of claim 1, wherein the content (%) fumaric acid in the whole pharmaceutical composition is 0.01-50%.

* * * * *

UNITED STATES PATENT AND TRADEMARK OFFICE
CERTIFICATE OF CORRECTION

PATENT NO. : 9,186,411 B2
APPLICATION NO. : 13/056593
DATED : November 17, 2015
INVENTOR(S) : Yasuhiro Hiraishi et al.

It is certified that error appears in the above-identified patent and that said Letters Patent is hereby corrected as shown below:

In the Claims:

At column 124, claim number 1, line numbers 23-29, replace "1-{5-(2-fluorophenyl)-1-[pyridin-3-ylsulfonyl)-1H-pyrrol-3-yl]-N-methylmethanamine) or a salt thereof, (N-methyl-1-[5-(2-methylphenyl)-1-(pyridin-3-ylsulfonyl)-1H-pyrrol-3-yl]methanamine) or a salt thereof, or (1-[4-fluoro-5-(2-fluoropyridin-3-yl)-1-(pyridin-3-ylsulfonyl)-1H-pyrrol-3-yl]-N-methylmethanamine) or a salt thereof"

with

--1-[5-(2-fluorophenyl)-1-(pyridin-3-ylsulfonyl)-1H-pyrrol-3-yl]-N-methylmethanamine or a salt thereof, N-methyl-1-[5-(2-methylphenyl)-1-(pyridin-3-ylsulfonyl)-1H-pyrrol-3-yl]methanamine or a salt thereof, or 1-[4-fluoro-5-(2-fluoropyridin-3-yl)-1-(pyridin-3-ylsulfonyl)-1H-pyrrol-3-yl]-N-methylmethanamine or a salt thereof--

Signed and Sealed this
Tenth Day of May, 2016

Michelle K. Lee
*Director of the United States Patent and Trademark Office*